US009295983B2

(12) United States Patent
Katz et al.

(10) Patent No.: US 9,295,983 B2
(45) Date of Patent: Mar. 29, 2016

(54) CALIXARENE-BOUND IRIDIUM-CONTAINING METAL COLLOIDS

(71) Applicants: The Regents of the University of California, Oakland, CA (US); Chevron U.S.A. Inc., San Ramon, CA (US)

(72) Inventors: Alexander Katz, El Sobrante, CA (US); Namal De Silva, Berkeley, CA (US); Andrew Solovyov, Berkeley, CA (US); Alexander Kuperman, Orinda, CA (US); Cong-Yan Chen, Kensington, CA (US); Partha Nandi, Berkeley, CA (US); Alexander Okrut, San Francisco, CA (US); Igor Busygin, Berkeley, CA (US)

(73) Assignees: THE REGENTS OF THE UNIVERSITY OF CALIFORNIA, Oakland, CA (US); CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 14/582,019

(22) Filed: Dec. 23, 2014

(65) Prior Publication Data

US 2015/0238949 A1 Aug. 27, 2015

Related U.S. Application Data

(63) Continuation of application No. 13/502,590, filed as application No. PCT/US2010/053818 on Oct. 22, 2010, now Pat. No. 8,969,607.

(60) Provisional application No. 61/254,163, filed on Oct. 22, 2009.

(51) Int. Cl.
| | |
|---|---|
| *B01J 31/24* | (2006.01) |
| *C07F 15/00* | (2006.01) |
| *C07C 5/03* | (2006.01) |
| *B01J 23/46* | (2006.01) |
| *B01J 31/16* | (2006.01) |
| *B01J 31/06* | (2006.01) |
| *B01J 35/00* | (2006.01) |

(52) U.S. Cl.
CPC *B01J 31/24* (2013.01); *B01J 23/46* (2013.01); *B01J 31/066* (2013.01); *B01J 31/16* (2013.01); *B01J 31/2404* (2013.01); *B01J 35/0013* (2013.01); *C07C 5/03* (2013.01); *C07F 15/0033* (2013.01); *B01J 2231/641* (2013.01); *B01J 2231/645* (2013.01); *B01J 2231/70* (2013.01); *B01J 2531/0211* (2013.01); *B01J 2531/827* (2013.01); *B01J 2540/50* (2013.01); *C07C 2531/24* (2013.01)

(58) Field of Classification Search
CPC ......... B01J 31/24; C07F 15/0033; C07C 5/03
USPC ........................................... 556/16; 585/277
See application file for complete search history.

(56) References Cited

U.S. PATENT DOCUMENTS

| | | | |
|---|---|---|---|
| 5,763,731 A | 6/1998 | McVicker et al. | |
| 6,380,266 B1 | 4/2002 | Katz et al. | |
| 8,969,607 B2 * | 3/2015 | Katz et al. | 556/16 |
| 2005/0255332 A1 | 11/2005 | Katz et al. | |
| 2013/0018199 A1 | 1/2013 | Katz et al. | |

FOREIGN PATENT DOCUMENTS

JP 2013-508145 3/2013

OTHER PUBLICATIONS

Alexeev, O. et al., "Iridium Clusters Supported on γ-Al2O3: Structural Characterization and Catalysis of Toluene Hydrogenation", *Journal of Catalysis*, 176(2) 310-320 (1998).
Alexeev, O. et al., "Partially Decarbonylated Tetrairidium Clusters on MgO: Structural Characterization and Catalysis of Toluene Hydrogenation", *J. Mol. Catal.*, 162, 67-82 (2000).
Argo, A.M. et al., "Observation of ligand effects during alkene hydrogenation catalysed by supported metal clusters", *Nature*, 415, 623-626 (2002).
Astuc, D. (Ed.), "Gold Nanoparticles-catalyzed Oxidations in Organic Chemistry", *Nanoparticles and Catalysis*, Chapter 13, pp. 438-439 (2008).
Bagatin, I. and Matt, D., "Calix[4] arene Ligands with Phosphorus-Containing Groups Tethered at the Upper Rim" *Inorg. Chem.*, vol. 38, pp. 1585-1591 (1999).
Bäumer, M. et al., "On the role of oxygen in stabilizing low-coordinated Au atoms", *Chem. Phys. Chem.*, 7, 1906-1908 (2006).
Becerril, H.A. et al., "DNA-templated nanofabrication", *Chem. Soc. Rev.*, 38, 329-337 (2009).
Bjørnholm, T. et al., "Directed Assembly of Gold Nanoparticles", *Current Opinion in Colloids and Interface Science*, 14, 126-134 (2009).
Böhmer, V., "Calixarenes, Macrocycles with (Almost) Unlimited Possibilities", *Angew. Chem. Int. Ed. Engl.* 34:713 (1995).
Bond, G.C. et al., "Hydrogenation over supported gold catalysts", *J. Chem. Soc. Chem. Commun.*, 44-45 (1973).
Byrne, M., "Electrocatalytic reduction of ethylene on gold and other substrates", *J. Chem. Soc. Faraday Transactions I*, 68, 1898 (1972).
Chen, M. et al., "Phase transition of silver nanoparticles from aqueous solution to chloroform with the help of inclusion complexes of p-sulfonated calix[4]arene and alkanethiol molecules and its application in the sie sorting of nanoparticles", Nanotechnology, 18, 1-7 (2007).
Chini, P. et al., "New Tetrahedral Cluster Compounds of Iridium. Synthesis of the Anions [Ir$_4$(CO)$_{11}$X]$^-$(X=Cl, Br, I, CN, SCN) and X-Ray Structure of [PPh$_4$][IR$_4$(CO)$_{11}$ Br]", *Journal of Organometallic Chemistry*, 152, C35-C38 (1978).

(Continued)

*Primary Examiner* — Porfirio Nazario Gonzalez
(74) *Attorney, Agent, or Firm* — Morgan, Lewis & Bockius LLP; Jeffry S. Mann

(57) ABSTRACT

The invention provides complexes in which a calixarene-related compound is coordinated to an iridium-containing metal colloid. The complexes can be immobilized on a substrate. The complexes of the invention are useful as tunable and highly robust isolated metal colloids that find use in binding of molecules and catalysis of chemical reactions.

4 Claims, 41 Drawing Sheets

(56) References Cited

OTHER PUBLICATIONS

Corma, A., et al., "Gold Nanoparticles in Organic Capsules: A Supramolecular Assembly of Gold Nanoparticles and Cucurbituril", *Chemistry—A European Journal*, 13 (22), 6359-6364 (2007).
Chetcuti, M. J. et al., "Synthesis of mono-, di- and tetra-alkyne functionalized calix[4]arenes: Reactions of these multipodal ligands with dicobalt octacarbonyl to give complexes which contain up to eight cobalt atoms", *Dalton Transactions*, Issue 16, pp. 2999-3008 (2009).
Choudhary, T.V. et al., "Oxidation catalysis by supported gold nanoclusters", *Top. Catal.*, 21, 25-34 (2002).
Crooks et al., "Dendrimer-Encapsulated Metal Nanoparticles: Synthesis, Characterization, and Applications to Catalysis", *Accounts of Chemical Research*, 34(3) 181-190 (2001).
Csok, Z. et al., "Carobonylation (hydroformylation and hydrocarbalkoxylation) reactions in the presence of transition metal: p-tert-butyl-calix[4]arene-based phosphine and phophinite systems", *Journal of Organometallic Chemistry*, 570: 23-29 (1998).
Danil de Namor, A. et al., Reaction of tetrakis[(3-pyridylmethyl)oxy] p-tert-butycalix(4)arene with $KAuCl_4$ and $K_2PtCl_6$. New pyridinocalix(4)arene adducts of gold(III) and platinum(IV) *Polyhedron*, vol. 16, No. 11, pp. 1885-1888 (1997).
De Silva, N. et al., "A bioinspired approach for controlling accessibility in calix[4]arene-bound metal cluster catalysts", Nature Chemisty, 2, 1062-1068 (2010).
De Silva et al., "Patterned Metal Polygedra Using Calixarenes as Organizational Scaffolds: $Ir_4$-based Cluster Assmblies", *Dalton Transactions* 39(9), pp. 2194-2197 (2010).
Denicourt-Nowicki, A. et al., "Methylated cyclodextrins: an efficient protective agent in water for zerovalent ruthenium nanoparticles and a supramolecular shuttle in alkene and rene hydrogenation reactions", *Dalton Transactions*, 48, 5714-5719 (2007).
Denicourt-Nowicki, A. et al., "Carbon-Supported Ruthenium Nanoparticles Stabilized by Methylated Cyclodextrins: A New Family of Heterogeneous Catalysts for the Gas-Phase Hydrogenation of Arenes", *Chemistry—A European Journal*, 14: 8090-8093 (2008).
Deutsch, S.E. et al., "Near Absence of Support Effects in Toluene Hydrogenation Catalyzed by MgO-Supported Iridium Clusters", *Journal of Catalysis*, 170(1) 161-167 (1997).
Dieleman, C.B. et al., Facile Synthetic Route to Cone-shaped Phosphorylated [$CH_2P(O)Ph_2$] Calix[4]arenes, *Journal of the Chemical Society, Dalton Transactions: Inorganic Chemistry*, 18, 3097-3100 (1995).
Dieleman, C.B. et al., "Arranging phosphoryl ligands on a calixarene platform", *Journal of Organometallic Chemistry*, vols. 545-546, pp. 461-473 (1997).
Dijkstra, P.J. et al., "Kinetically stable complexes of alkali cations with rigidified calix[4]arenes: synthesis, x-ray structures, and complexation of calixcrowns and calixspherands", *J. Am. Chem. Soc.*, 111: 7567-7575 (1989).
Fahlbusch, T. et al., "N-Heterocyclic Carbene Complexes of Mercury, Silver, Iridium, Platinum, Ruthenium, and Palladium Based on the Calix[4]arene Skeleton" *Organometallics*, vol. 28, pp. 6183-6193 (2009).
Fischer, R. et al., "Pd@MOF-5: limitations of gas-phase infiltration and solution impregnation of [$Zn_4O(bdc)_3$] (MOF-5) with metalorganic palladium precursors for loading with Pd nanoparticles", *J. Materials Chem.*, 19: 1314-1319 (2009).
Friend, C.M. et al., "Effects of chlorine and oxygen coverage on the structure of the Au(111) surface", The Journal of Chemical Physics, 130, 3232-3238 (2009).
Gates, B.C. et al., "Faujasite-Supported $Ir_4$ Clusters: A Density Functional Model Study of Metal-Zeolite Interactions", *J. Phys. Chem. B*, 103: 5311-5319 (1999).
Gates, B.C. et al., "Xe NMR Spectroscopy of Metal Carbonyl Clusters and Metal Clusters in Zeolite NaY", *J. Am. Chem. Soc.*, 121: 7674-7681 (1999).
Gates, B.C. et al., "Metal Carbonyl Cluster Synthesis in Nanocages: Spectroscopic Evidence of Intermediates in the Formation of $Ir_4(CO)_{12}$ in Zeolite NaY", *J. Phys. Chem. B*, 108: 11259-11264 (2004).
Gates, B.C. et al., "Size-Dependent Catalytic Activity of Zeolite-Supported Iridium Clusters", *J. Phys. Chem. C*, 111, 262-267 (2007).
Gates, "Supported Metal Clusters: Synthesis, Structure, and Catalysis", *Chemical Reviews*, vol. 95, No. 3, pp. 51-522 (1995).
Giannini, L. et al., "Organometallic Reactivity on a Calix[4]arene Oxo Surface. Synthesis and Rearrangement of Zr-C Functionalities Anchored to a Calix[4]arene Moiety", *J. Am. Chem. Soc.*, 119, 9198 (1997).
Giannini, L. et al., "Olefin Rearrangements Assisted by a Molecular Metal-Oxo Surface: The Chemistry of Calix[4]arene Tungsten(IV)", *J. Am. Chem. Soc.*, 121: 2797-2807 (1999).
Goodman, W. et al., "Catalytically active gold: From colloids to ultrathin films", *Acc. Chem. Res.*, 39, 739-746 (2006).
Gopidas, K.R. et al., "Nanoparticle-Cored Dendrimers: Synthesis and Characterization", *J. Am. Chem. Soc.*, 125, 6491-6502 (2003).
Gutsche, C.D. et al., "Calixarenes 9: Conformational isomers of the eters and esters of calix[4]arenes", *Tetrahedron*, 39(3), 409-426 (1983).
Ha, J-M. et al., "Accessibility in Calix[8]arene-Bound Gold Nanoparticles: Crucial Role of Induced-Fit Binding", J. Phys. Chem., 114, 16060-16070 (2010).
Ha et al., "Postsynthetic Modification of Gold Nanoparticles with Calix[4]arene Enantiomers: Origin of Chiral Surface Plasmon Resonance", *Langmiur* 25(1), pp. 153-158 (2009).
He, X. et al., "Design and Syntheis of Calixarene-Based Bis-alkynyl-Bridged Au Isonitrile Complexes as Luminescent Ion Probes by the Modulation of Au—Au Interactions" *Chem. Eur. J.*, vol. 15, pp. 8842-8851 (2009).
Ha, J.M. et al., "Mercaptocalixarene-Capped Gold Nanoparticles via Postsynthetic Modification and Direct Synthesis: Effect of Calixarene Cavity-Metal Interactions", *J. Phys. Chem. C.*, vol. 113, No. 4, pp. 1337-1142 (2009).
Ha, J.M. et al., "Synthesis and Characterization of Accessible Metal Surfaces in Calixarene-Bound Gold Nanoparticles", *Langmuir*, 25(18), pp. 10548-10553 (2009).
Haratua, A. et al., "When gold is not noble: Catalysis by nanoparticles", *Chemical Record*, 3, 75-87 (2003).
Hughes, M.D. et al., Tunable gold catalysts for selective hydrocarbon oxidation under mild conditions, *Nature*, 437, 1132-1135 (2005).
Ishii, Y. et al., "Site-selective and stepwise complexation of two M(cod)+(M=Rh, Ir) frag,emts with calix[4]arene" *ChemComm*, pp. 1150-1151 (2002).
Iwamoto, K. et al., "Remarkable metal template effects on selective synthesis of p-t-butylcalix[4]arene conformers", Tetrahedron Letters, 31: 7169-7172 (1990).
Katz, A. et al., "Grafted Metallocalixarenes as Single-Site Surface Organometallic Catalysts", *J. Am. Chem. Soc.*, 126:16478-16486 (2004).
Katz, A. et al., "Energetics of Small Molecule and Water Complexation in Hydrophobic Calixarene Cavities", 22:4004-4014 (2006).
Katz, A. et al., "The Role of Outer-Sphere Surface Acidity in Alkene Epoxidation Catalyzed by Calixarene-Ti(IV) Complexes", *J. Am. Chem. Soc.*, 129: 15585-15595 (2007).
Katz, A. et al.., "Structural Assessment and Catalytic Consequences of the Oxygen Coordination Environment in Grated Ti-Calixarenes", *J. Am. Chem. Soc.*, 129: 1122-1131 (2007).
Katz, A. et al., "Vanadocalixarenes on Silica: Requirements for Permanent Anchoring and Electronic Communication", *Chemistry of Materials*, 21: 1852-1860 (2009).
Lee, S. et al., "Selective Propene Epoxidation on Immobilized Au6-10 Clusters: The Effect of Hydrogen and Water on Activity and Selectivity", *Agnew. Chem. Int. Ed.*, 48, 1467-1471 (2009).
Li H.Y. et al., "Nanofabrication by DNA self-assembly", *Mater. Today*, 12, 24-32 (2009).
Liu, W. et al., "Size-controlled gold nanocolloids on polymer microsphere-stabilizer via interaction between functional groups and gold nanocolloids", Journal of Colloid and Interface Science, 313, 494-502 (2007).

(56) References Cited

OTHER PUBLICATIONS

Mallouk, T. et al., "Chemistry at the Nano-Bio Interface", *Journal of Org. Chem.*, 131, 7937-7939 (2009).
Maloney, S.B. et al., "A Well-Defined Supported Metal Catalysts: $Ir_4$/MgO", *Catal. Lett.*, 5, 161-168 (1990).
Marmor, R. et al., "Synthesis of hydroxymethyl(diphenyl)phosphine oxide and substituted .alpa.-hydroxybenzyl(diphenyl)phosphine oxides", *The Journal of Organic Chemistry*, 34(3), 748-749 (1969).
Naito, S. et al., "Mechanism of deuterium addition and exchange of propene over silica-supported gold and silver catalysts", *J. Chem. Soc. Faraday Transactions I*, 84, 4115-4124 (1988).
Neri et al., "Study on the Alkylation of p-tert-Butycalix[8]arene, Partially O-Alkylated Calix[8]arenes", *The Journal of Organic Chemistry*, 59: 3880-3889 (1994).
Nowicki, A. et al., "Supramolecular shuttle and protective agent: a multiple role of methylated cyclodextrins in the chemoselective hydrogenation of benzene derivatives with ruthenium nanoparticles", *Chem. Commun.*, 296-298 (2006).
Ozerov, O. et al., "Highly Regioselective [2+2+2] Cycloaddition of Terminal Alkynes Catalyzed by $\eta^6$-Arene Complexes of Titanium Supported by Dimethylsilyl-Bridged *p-tert*-Butyl Calix[4]arene Ligand", *J. Am. Chem. Soc.*, 122:6423-6431 (2000).
Patra, C.R., et al., "Application of gold colloids for targeted therapy in cancer", *Journsl of Biomedical Nanotechnology.*, 4, 99-132 (2008).
Plourde, F. et al., "Syntheses and Characterization of Upper Rim 1,2- and 1,3- Diphosphinated Calix[4]arenes and Their Corresponding 1,5-Cycloctadienylrhodium(I) Complexes: Comparison of the Catalytic Hydroformylation Properties of Terminal Alkenes" *Organometallics*, vol. 22, pp. 2862-2875 (2003).
Riviere, C. et al., "Nanosystems for medical applications: Biological detection, drug delivery, diagnosis and therapy", *Annales de Chimie-science des Materiaux*, 31, 351-367 (2006).
Roldán, A. et al., "Critical Size for O-2 Dissociation by Au Colloids", *Chem. Phys. Chem.*, 10, 348 (2009).
Sameni, S. et al., "Calix[4]arene-Phosphine Dimers: Precursors of Flexible Metallo-Capsules and Self-Compacting Molecules" *Chem. Eur. J.*, vol. 15, pp. 10446-10456 (2009).
Scodeller, P., et al., "Wired-Enzyme Core-Shell Au Colloid Biosensor", *J. Am. Chem. Soc.*, 12690-12697 (2008).
Sermon, P.A. et al., "Hydrogenation of alkenes over supported gold", *J. Chem. Soc. Faraday Transactions I*, 75, 385-394 (1979).
Somorjai, G. et al., "Lithographic Fabrication of Model Systems in Heterogeneous Catalysis and Surface Science Studies", *Langmuir*, 14(6), 1458-1464 (1998).
Staffilani, M. et al., "Anion Binding within the Cavity of π-Metalated Calixarenes" *J. Am. Chem. Soc.*, vol. 119, pp. 6324-6335 (1997).
Sylvestre, J. et al., "Stabilization and Size Control of Gold Nanoparticles during Laser Ablation in Aqueous Cyclodextrins", Journal of the American Chemical Society, 126, 7176-7177 (2004).
Triantafillou, N.D. et al., "Magnesia-Supported Tetrairidium Clusters Derived from [$Ir_4(CO)_{12}$]", *J. Phys. Chem.*, 98, 8431-8441 (1994).
Turner, M. et al., "Selective oxidation with dioxygen by gold colloid catalysts derived from 55-atom clusters", *Nature*, 454, 981-U31 (2008).
Van Son, F.B.M. et al., "Structure and nature of the metal-support interface: characterization of iridium clusters on magnesium oxide by extended x-ray absorption fine structure spectroscopy", *Journal of the American Chemical Society*, 115, 10317-10326 (1993).
Vicens J. et al., "Synthesis of mono-, di- and tetra-alkyne functionalized calix[4]arenes: reactions of these multipodal ligands with dicobalt octacarbonyl to give complexes which contain up to eight cobalt atoms", *Dalton Transactions*, 2999-3008 (2009).
Vuori, H. et al., "Beta Zeolite-Supported Iridium Catalysts by Gas Phase Deposition", *Catalysis Letters*, 131:7-15 (2009).
Wang, G.L. et al., "DNA binding of an ethidium intercalcator attached to a monolayer-protected gold cluster", *Anal. Chem.*, 17, 4320-4327 (2002).
Wang, L.H. et al., "Gold colloid-based optical probes for target-responsive DNA structures", *Gold. Bull.*, 41, 37-41 (2008).
Watson et al., "Diphosphine ligand chelation and bridging and regiospecific ortho metalation in the reaction of 4,5-bis(diphenylphosphino)-4-cyclopenten-1,3-dione (bpcd) with $Ir_4(CO)_{12}$: X-ray diffraction structures of $Ir_4(CO)_7(\mu\text{-}CO)_3$(bpcd), $Ir_4(CO)_5(\mu\text{-}CO)_3$(bpcd)($\mu$-bpcd), and $HIr_4(CO)_4(\mu\text{-}CO)_3$(bpcd)[$\mu$-PhP($C_6H_4$)C=C(PPh_2(O)CH_2C(O)$)]", *Journal of Organometallic Chemistry*, 693, 1439-1448 (2008).
Wei, A. et al., "Prenucleation and coalescence of cobalt nanoclusters mediated by multivalent calixarene complexes", *Chemical Communications*, 4254-4256 (2009).
Wei et al., "Calixerene-Encapsulated Nanoparticles: Self-Assembly Into Functional Nanomaterials", *Chemical Communications*, Issue 15, pp. 1581-1591 (2006).
Wegener, W., "Zur Darstellung der Sulfonsäureester von Hydroxymethylphosphorylverbindungen", *Zeitschrift für Chemie*, 11: 262 (1971).
Wieser-Jeunesse, C. et al., "Directed Positioning of Organometallic Fragments Inside a Calix[4]arene Cavity" Angew. Chem. Int. Ed., vol. 37, No. 20, pp. 2861-2864 (1998).
Xu, W. et al., "Propargyl calix[4]arenes and their complexes and with silver(I) and gold(I)" *Can. J. Chem.*,vol. 74, No. 5, pp. 766-774 (1996).
Xu,Z . et al., "Size-dependent catalytic activity of supported metal clusters", *Nature*, 372: 346-348 (1994).
Young, K. et al, "Experimental realization of catalytic $CH_4$ hydroxylation predicted for an iridium NNC pincer complex, demonstrating thermal, protic, and oxidant stability", *Chem. Commun.*, 3270-3272 (2009).
Zhao, W., et al., "DNA Aptamer Folding on Gold Colloids: From Colloid Chemistry to Biosensors", *J. Am. Chem. Soc.*, 130, 3610-3618 (2008).
Zhang, Q. et al., "Effect of Ph on the Interaction of Gold Nanoparticles with DNA and Application in the Detection of Human p53 Gene Mutation", *Nanoscale Research Letters*, 4: 216-220 (2009).

\* cited by examiner (a)

(b)

(a)

(b)

CALIXARENE-BOUND IRIDIUM-CONTAINING METAL COLLOIDS

CROSS-REFERENCE TO RELATED APPLICATIONS

This application is a Continuation of U.S. application Ser. No. 13/502,590, now U.S. Pat. No. 8,969,607, which is a 371 National Stage entry of PCT/US2010/053818 filed Oct. 22, 2010 which claims under 35 USC 119(e)(1) the benefit of U.S. Application No. 61/254,163, filed Oct. 22, 2009, all of which are incorporated by reference in their entireties for all purposes.

TECHNICAL FIELD

This invention relates to calixarenes and related compounds. More specifically, the invention relates to calixarenes and related compounds coordinated to an iridium-containing metal colloid through a linker component of the calixarene-related compound, which includes a coordinating atom coordinated to at least one iridium atom on the colloid. The resulting calixarene-bound colloids can be immobilized on the surface of a substrate, and used as catalysts.

BACKGROUND

Calixarenes are a well-known class of cyclic oligomers that are usually made by condensing formaldehyde with p-alkylphenols under alkaline conditions. V. Bohmer summarized the chemistry of calixarenes in an excellent review article (*Angew. Chem., Int. Ed. Engl.* 34: 713 (1995). Early transition metal complexes in which the four oxygen atoms of calix[4] arenes or O-methylated calix[4]arenes chelate to the metal are now known (see, e.g., *J. Am. Chem. Soc.* 119: 9198 (1997)).

Metal colloids constitute a group of compounds which have favorable properties as catalysts and catalyst precursors. In U.S. Pat. No. 4,144,191, a bimetallic carbonyl cluster compound catalyst for producing alcohols by hydroformylation is disclosed; either $Rh_2Co_2(CO)_{12}$ or $Rh_3Co(CO)_{12}$ is used, bound to an organic polymer containing amine groups. The catalyst operates at low temperature and produces almost exclusively alcohols.

In the Finnish patent application No. 844634 the observation is made that a mixture of the monometal cluster compounds $Rh_4(CO)_{12}$ and $Co_4(CO)_{12}$ bound to an amine resin carrier serves as the extremely selective catalyst in producing alcohols. An advantage of the cluster mixture catalyst is that it is simpler to prepare and its activity can be optimized as a function of the mole proportion of the metals. When supported on inorganic oxide surfaces, iridium metal colloids in the form of clusters such as $Ir_4$ and nanoparticles are active catalysts for olefin hydrogenation (*Nature* 415: 623 (2002)) and toluene hydrogenation (*Journal of Catalysis* 170: 161 (1997) and *Journal of Catalysis* 176: 310 (1998)). Besides olefin hydrogenation, iridium is in general used for a variety of catalytic processes that include propane hydrogenolysis, CO hydrogenation, toluene hydrogenation, decalin ring opening and related conversion of methlcyclohexane to dimethylpentanes (See Catalysis Letters 131: 7 (2009)), methanation, intramolecular hydroamination, asymmetric isomerization of primary allylic alcohols, allylic amination, hydroamination, hydrothiolation, C—H bond arylation of heteroarenes using iodoarenes, [2+2+2] cycloadditions, carbonylation of methanol, methane hydroxylation (See Chemical Communications 3270-3272 (2009)), and selective naphthenic ring opening without significant dealkylation of pendant substituents on the right (See U.S. Pat. No. 5,763, 731).

It is known that the chemical properties of metal clusters such as catalytic activity or electronic properties such as electron binding energy vary depending on the size of cluster (aggregate of atoms) and the nature and number of ligands. It is further known that a critical limitation that prevents industrial application of metal clusters and, in general, metal colloid catalysts is lack of stability against aggregation (Gates et al., *Nature* 372: 346 (1994)). One method of dealing with lack of stability of metal clusters is to deposit them on a support such as a planar surface of an inorganic oxide or the interior microporosity of a zeolite. These surfaces can impart additional stability to metal clusters, and this has been demonstrated previously for $Ir_4$ metal colloid species inside of zeolites even when decarbonylated (Gates et al., J. Phys. Chem. B 103: 5311 (1999), Gates et al., J. Am. Chem. Soc. 1999 121: 7674 (1999), Gates et al., J. Phys. Chem. B 108: 11259 (2004), and Gates et al., J. Phys. Chem. C 111: 262 (2007)). However, as ligands, zeolitic and inorganic oxide surfaces lack the ability to widely tune the catalytic and electronic properties of the cluster in large part because of the lack of available functional groups for interacting with the cluster (limited to be O, Si, and Al for zeolite), when compared with an organic ligand. In addition, it would be highly desirable to pattern discrete numbers of clusters in an organized spatial fashion relative to one another, because such organization can in principle also be used to affect catalysis. This is not possible to accomplish using the planar surface of an inorganic oxide or the interior microporosity of a zeolite as a template because more or less random deposition of cluster results throughout. The same is true when using the interior microporosity of a metal-organic framework material (See J. Materials Chem. 19: 1314 (2009)). Lithographic fabrication methods that have been used in the semiconductor industry have been used to prepare arrays of metal particles that are uniform in size, but these particles are typically larger than 100 nm in diameter (See Somorjai et al., *Langmuir* 14: 1458 (1998)). Recently, calixarenes have been successfully used as ligands to pattern up to eight cobalt colloids using the calixarene molecule as an organizational scaffold (See Vicens, et al., *Dalton Transactions* 2999-3008 (2009) and Wei et al., *Chem Comm* 4254-4256 (2009)). These colloids were synthesized via direct reaction of either $Co_2(CO)_8$ or $Co_4(CO)_{12}$ with alkyne-containing resorcinarene, under conditions that are identical to those used for non-calixarene ligands consisting of a single alkyne group. However, this type of direct reaction approach failed to synthesize a well-defined, characterizable set of products when reacting with the metal polyhedron, when using $Co_4(CO)_{12}$, and also fails at synthesizing calixarene-bound iridium colloids, as detailed in Example 4 herein. To-date, there have been no reports of calixarene complexes of iridium-containing metal colloids. An additional advantage when using a calixarene as ligand for a metal colloid is that the calixarene can be used to confine the nucleation and growth of the colloid during synthesis to be a small size via geometric restrictions and/or multivalency (See Wei et al., *ChemComm* 4254-4256 (2009)). This type of confinement during metal colloid nucleation and growth has also been demonstrated previously using dendrimers as ligands for metal colloids (See Crooks et al., Accounts of Chemical Research 34: 181 (2001)); however, dendrimers do not allow control of patterning discrete numbers of less than eight colloids. The current invention offers the ability to pattern colloids in an organized assembly while also offering tunability of environment.

Some catalytic effects of transition metals complexed with calixarenes have been shown for olefin rearrangements [Giannini et al., *J. Am. Chem. Soc.* 121: 2797 (1999)], cycloaddition of terminal alkanes [Ozerov et al., *J. Am. Chem. Soc.* 122: 6423 (2000)] and hydroformylation [Csok et al., *J. Organometallic Chem.* 570: 23 (1998)]. The calixarenes in those investigations were coordinated with one or more metal cations that do not contain interactions between reduced metals as in a metal colloid. Calixarenes coordinated to metal cations that are grafted on oxide surfaces enforce isolation of the grafted metal cation by preventing aggregation into extended oxide structures [Katz et al., *J. Am. Chem. Soc.* 126: 16478 (2004)], [Katz et al., *J. Am. Chem. Soc.* 129: 15585 (2007)], and [Katz et al., *Chem. Mater.* 21: 1852 (2009)], and also afford the ability to tune catalysis of the grafted cation by virtue of the nature of coordinating groups as substituents on the calixarene skeleton [Katz et al, *J. Am. Chem. Soc.* 129: 1122 (2007)].

Coordinating a calixarene ligand to metal clusters offers numerous advantages including, but not limited to, more resiliency against aggregation due to the role of the calixarene as a sterically bulky barrier and, perhaps more importantly, opens the synthesis of new classes of highly tailorable functional materials, in which the calixarene serves as a nanoscale organizational scaffold for the assembly of complex active sites. The calixarene can also affect electron density on the metal colloid core by virtue of coordinating functional groups and substituents on the calixarene skeleton. In addition, metal colloids bound with calixarene contain void spaces either in between calixarenes on the surface or directly below the calixarene cavity, which can be used for binding and catalysis of molecules. All of the effects above have been previously demonstrated for calixarene-bound gold colloids [Katz et al., *Langmuir* 25: 10548 (2009)].

Quite surprisingly, the inventors have discovered a rich coordination chemistry between iridium metal colloids and calixarene-related compounds. The unobvious aspect of the present invention is further substantiated by Example 4 below that failed to produce an exemplary embodiment of the invention using methods established and known in the prior art.

SUMMARY OF INVENTION

The present invention provides, for the first time, coordination complexes formed between calixarene-related ligands (or "calixarene-related compounds", used interchangeably) and iridium-containing metal colloids. The use of calixarenes as ligands offers several non-obvious advantages, such as (i) protection against aggregation and sintering with the calixarene-related ligand acting as a sterically bulky ligand on the surface, (ii) accessibility to the metal surface (e.g., by void formation) by virtue of exposed metal located either directly below the calixarene-related ligand cavity or in areas between calixarenes, (iii) the capacity for tuning the electronic and steric properties of the metal colloid core by virtue of substituent functional groups on the calixarene-related ligand, thus enabling tuning of capped cluster catalytic properties and (iv) permitting selective placement of small clusters on the external surface of a microporous material, which may be critical in bifunctional catalysis. Also provided are calixarene-related compounds that act as easily variable ligands, tunable to achieve a particular desired property in a metal colloid coordinated to the ligand. Methods of making these ligands and coordinating them with metal colloids are also provided. Moreover, methods for making the compounds and methods for their use are also provided—in both their free and immobilized states. Calixarene-related metal colloids of this invention can be used to catalyze processes including those known in the art to be catalyzed by metal-mediated processes.

In an exemplary embodiment, the present invention includes a unique composition of matter consisting of a calixarene-related moiety bound to an iridium-containing metal moiety, which maintains protection of the metal moiety against aggregation/decomposition while also simultaneously providing for accessibility to molecules that can bind and/or react at the surface of the metal moiety. In an exemplary embodiment of the invention, the calixarene can be used to tune the electronic environment, steric access, patterning, and, ultimately, catalytic activity of the iridium-containing metal colloid core. In exemplary embodiments, the invention also provides a method of controlling aspects of the reactivity of iridium-containing metal colloids by coordination with calixarene-related moieties.

With the ability to tune the electron density as well as the stability of, for example, an $Ir_4$ cluster core by changing the number of attached calixarene phosphine ligands, L, a powerful "construction kit for catalysis" has been developed. The steric protection provided by the calixarene ligand shell is hypothesized to increase with increasing numbers of calixarene phosphines bound in the series $Ir_4(CO)_{12-x}(L)_x$. This should lead to an observation of greater cluster stability for clusters consisting of larger x values, decreasing the likelihood of agglomeration during catalysis as well as thermal (heating) processes. Furthermore, upon increasing the number of ligands bound to the metal core, the electron density within the cluster core is expected to increase. This in turn is also expected to influence catalytic activity.

DESCRIPTION OF EMBODIMENTS

Definitions

Figure 1:
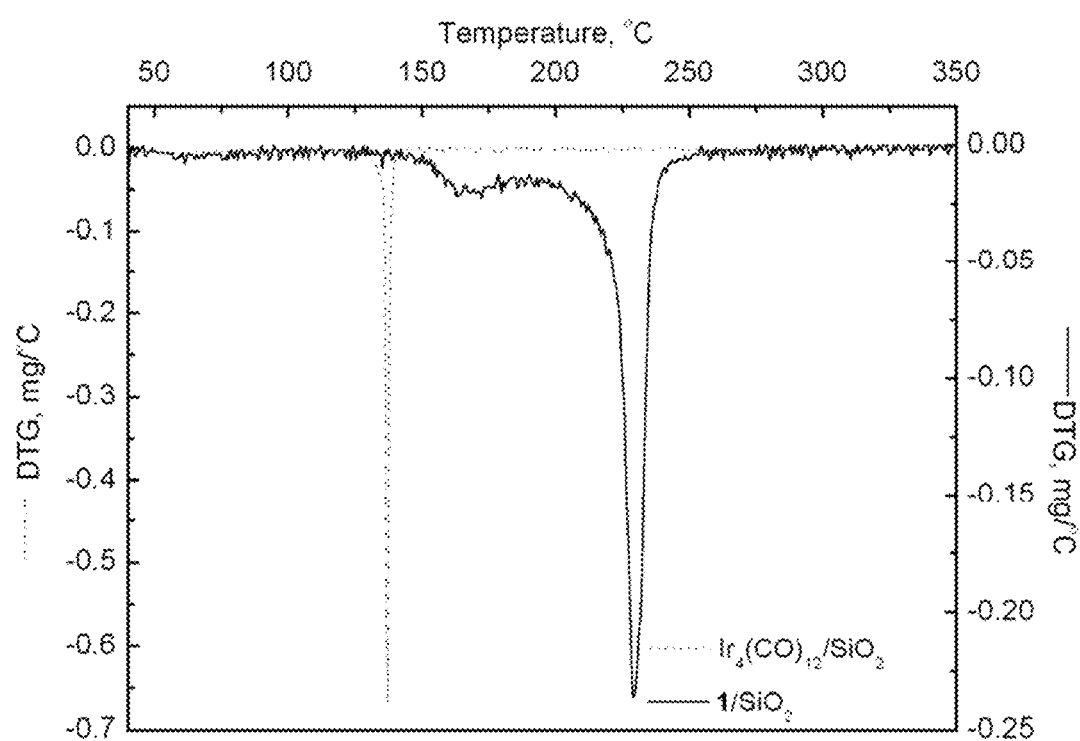
FIG. 1 shows a plot of derivative of weight with respect to temperature for 1 mixed with silica and $Ir_4(CO)_{12}$ mixed with silica during temperature programmed oxidative decomposition.
Figure 2:
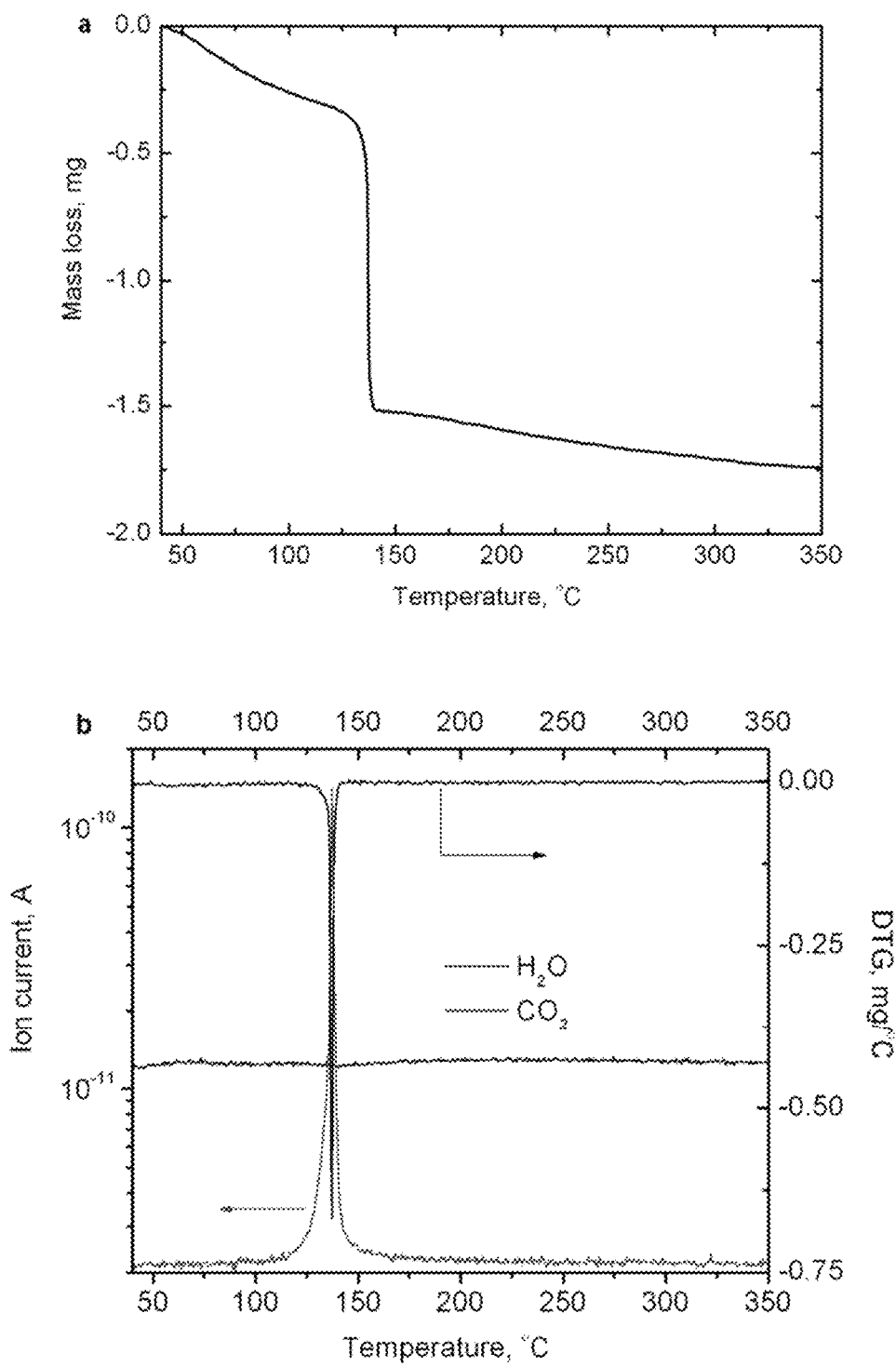
FIG. 2 shows the results of (a) thermogravimetric analysis of $Ir_4(CO)_{12}$ under oxidative conditions, (b) derivative of mass loss with respect to temperature (DTG) and mass spectrometer signals corresponding to water, phenyl, and $CO_2$ during same experiment as in (a).
Figure 3:
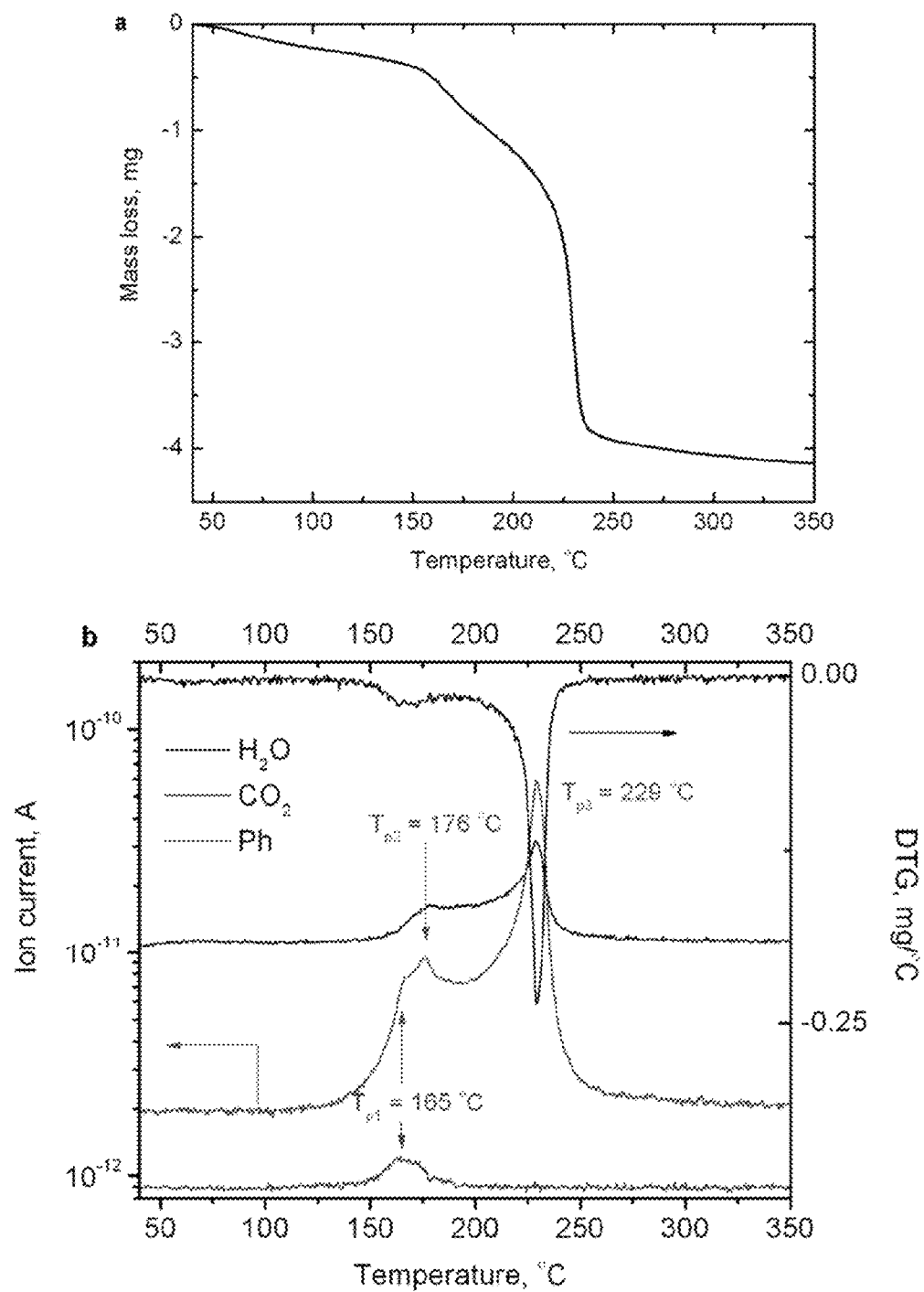
FIG. 3 shows the results of (a) thermogravimetric analysis of 1 under oxidative conditions, (b) derivative of mass loss with respect to temperature (DTG) and mass spectrometer signals corresponding to water, phenyl, and $CO_2$ during same experiment as in (a).
Figure 4:
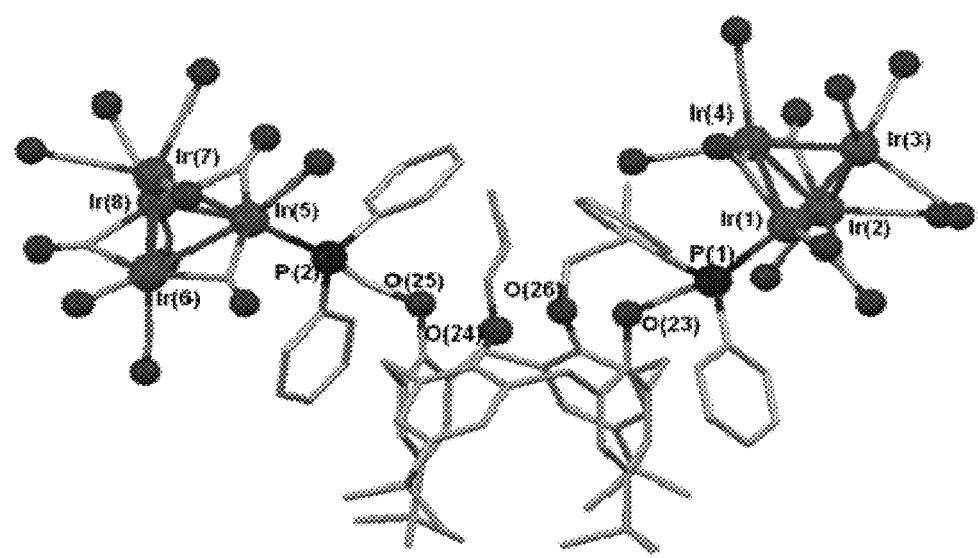
FIG. 4 shows the structure of calix[4]arene(OPr)$_2$(OCH$_2$PPh$_2$)$_2$(Ir$_4$(CO)$_{11}$)$_2$ derived from single-crystal X-ray diffraction. The Ir$_4$ metal core on the left is disordered and the positions of Ir(5), Ir(6), Ir(7) and Ir(8) atoms are shown in 68% occupancy
Figure 5:
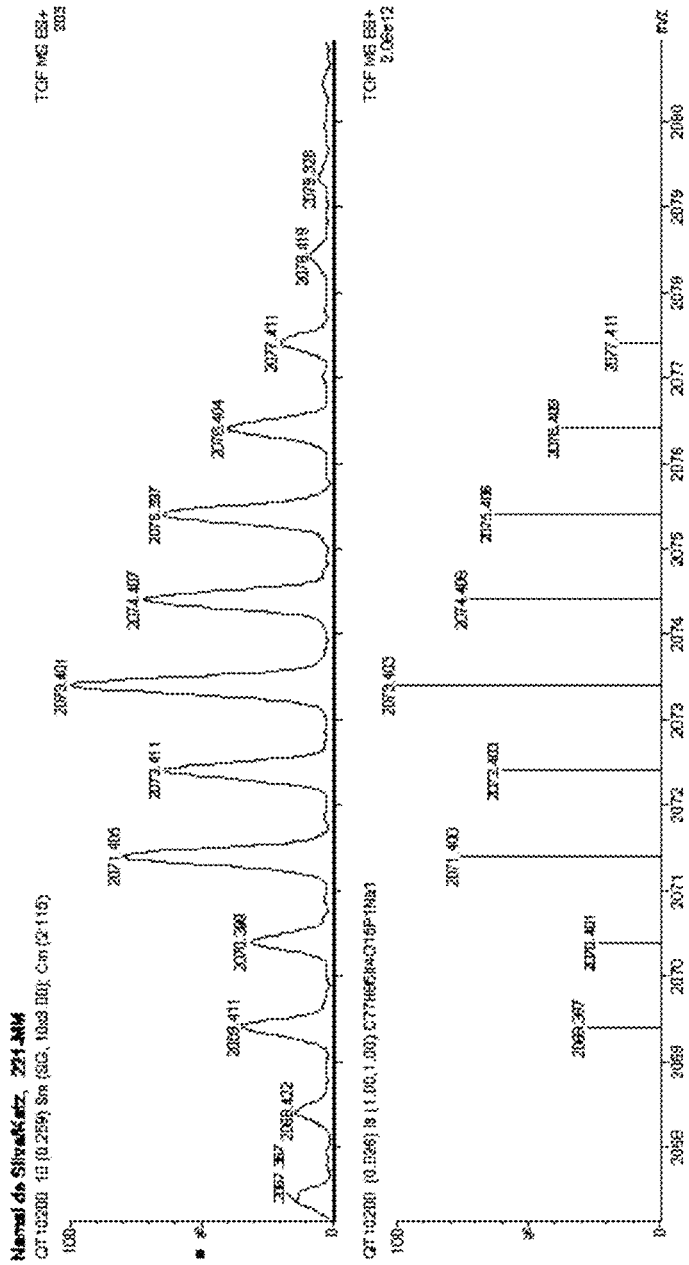
FIG. 5 shows the ESI mass spectrum showing molecular ion of [1Na]+; experimental (top), theoretical simulation (bottom)
Figure 6:
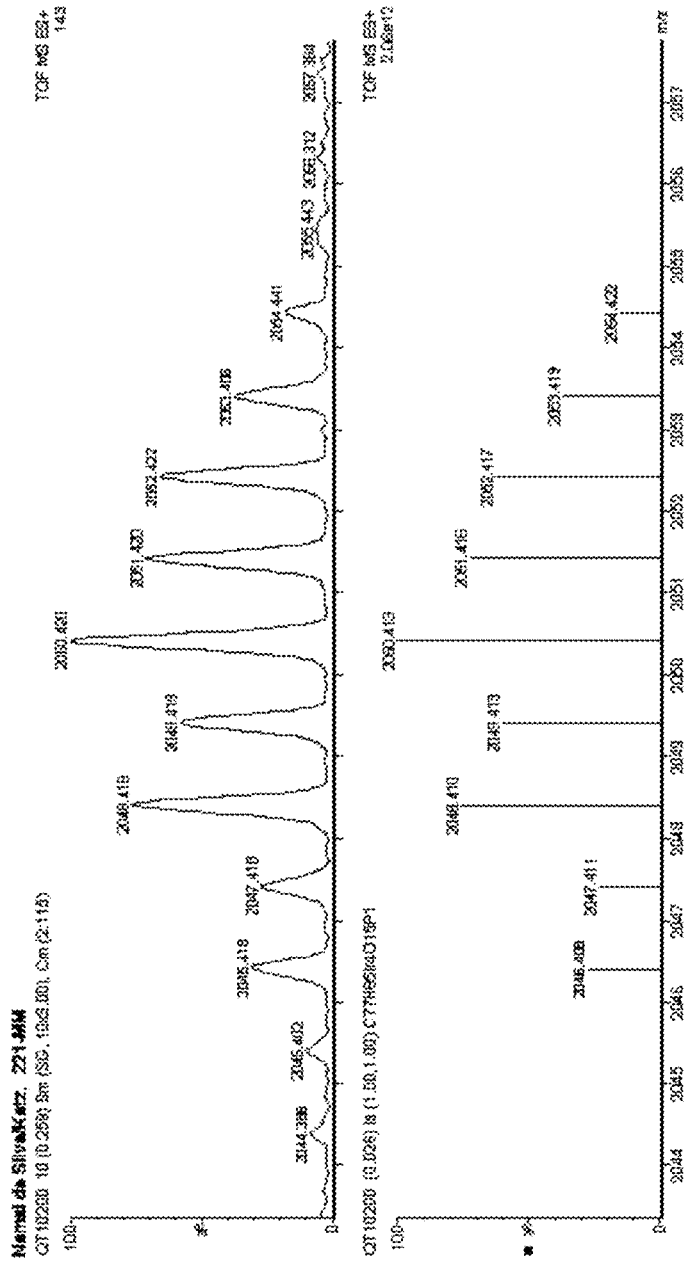
FIG. 6 shows the ESI mass spectrum showing molecular ion of [1]+; experimental (top), theoretical simulation (bottom)
Figure 7:
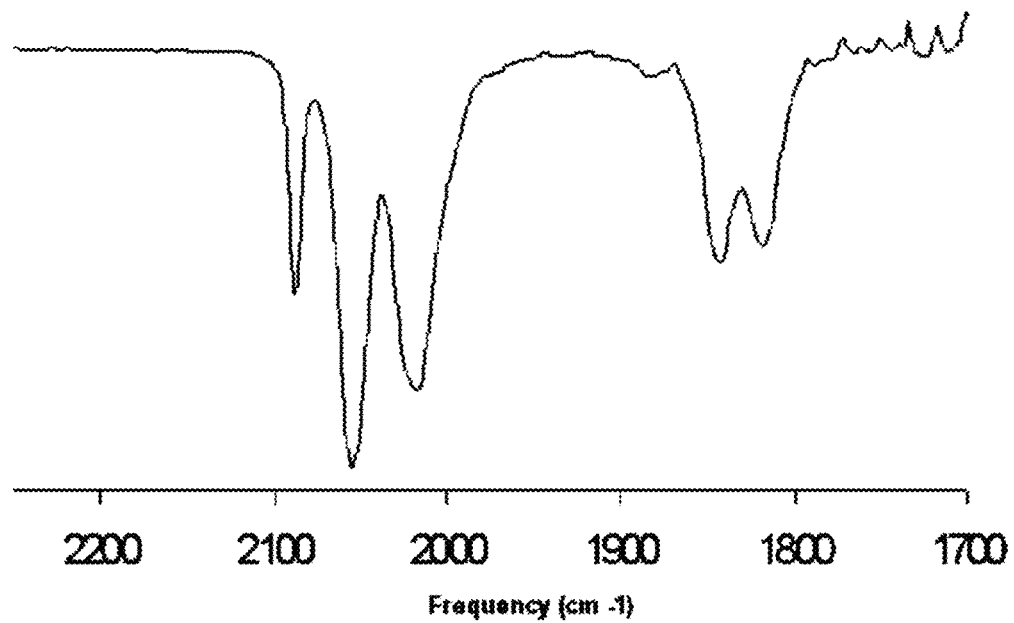
FIG. 7 shows the IR spectrum of 1 (in $CH_2Cl_2$)
Figure 8:
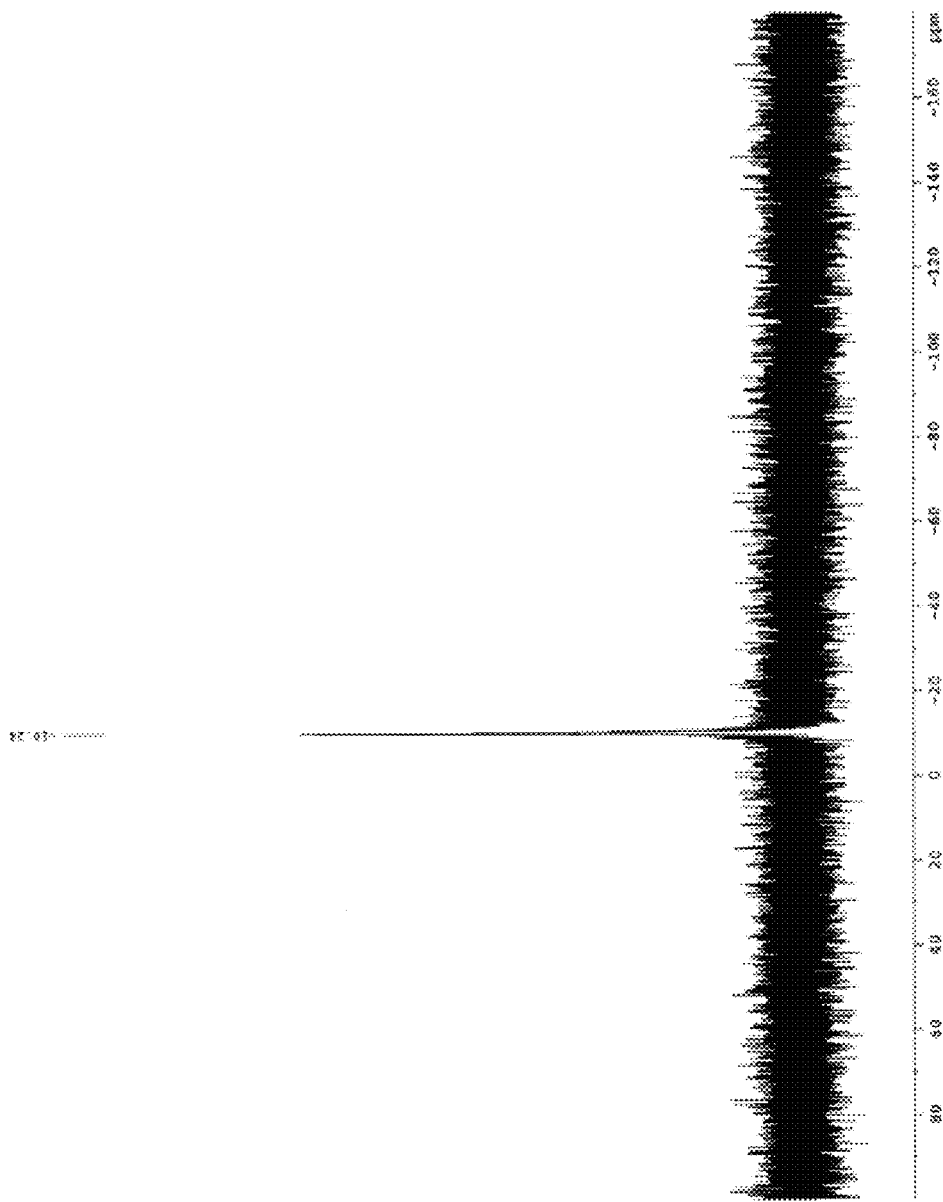
FIG. 8 shows the $^{31}$P NMR of 1 at room temperature
Figure 9:
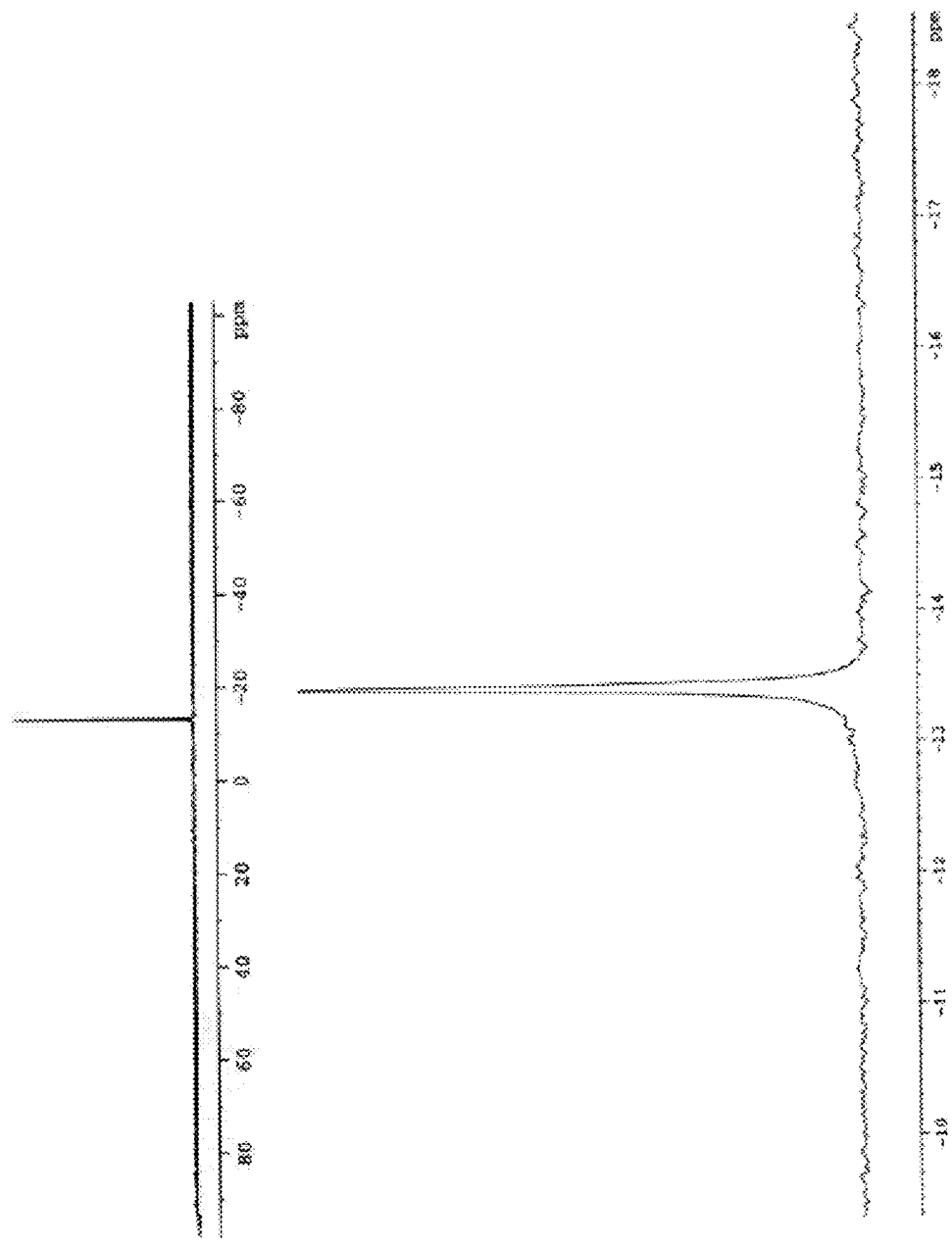
FIG. 9 shows the $^{31}$P NMR of 1 at −58° C.
Figure 10:
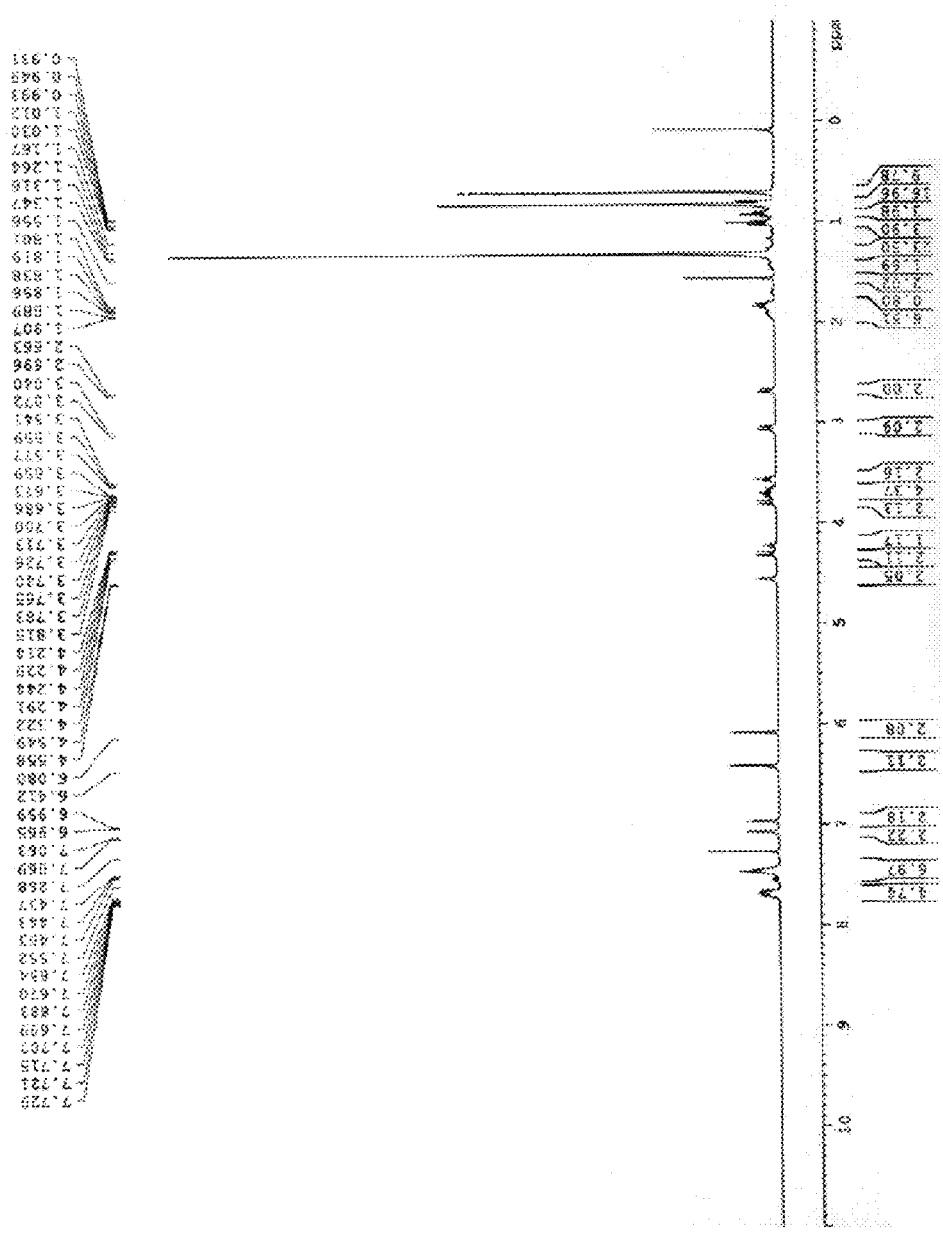
FIG. 10 shows the $^1$H NMR of 1 at room temperature
Figure 11:
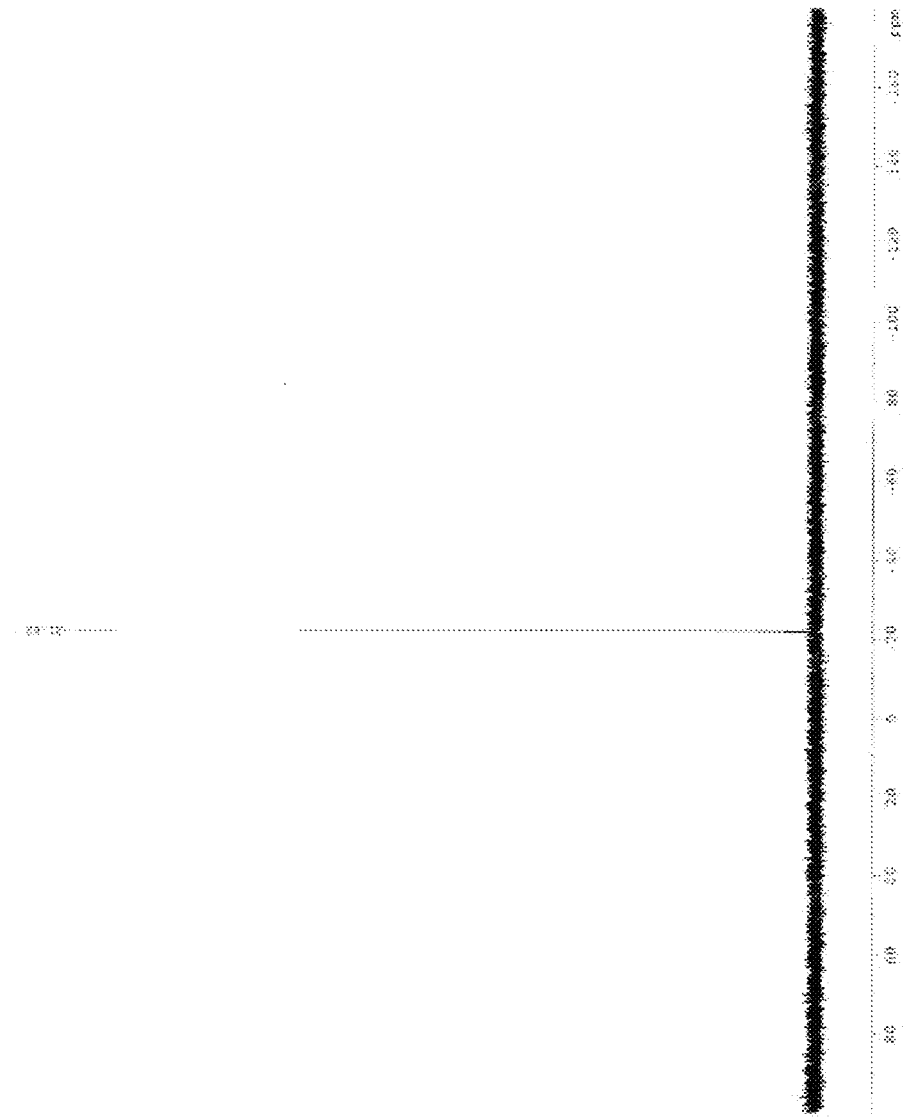
FIG. 11 shows the $^{31}$P NMR of 2.
Figure 12:
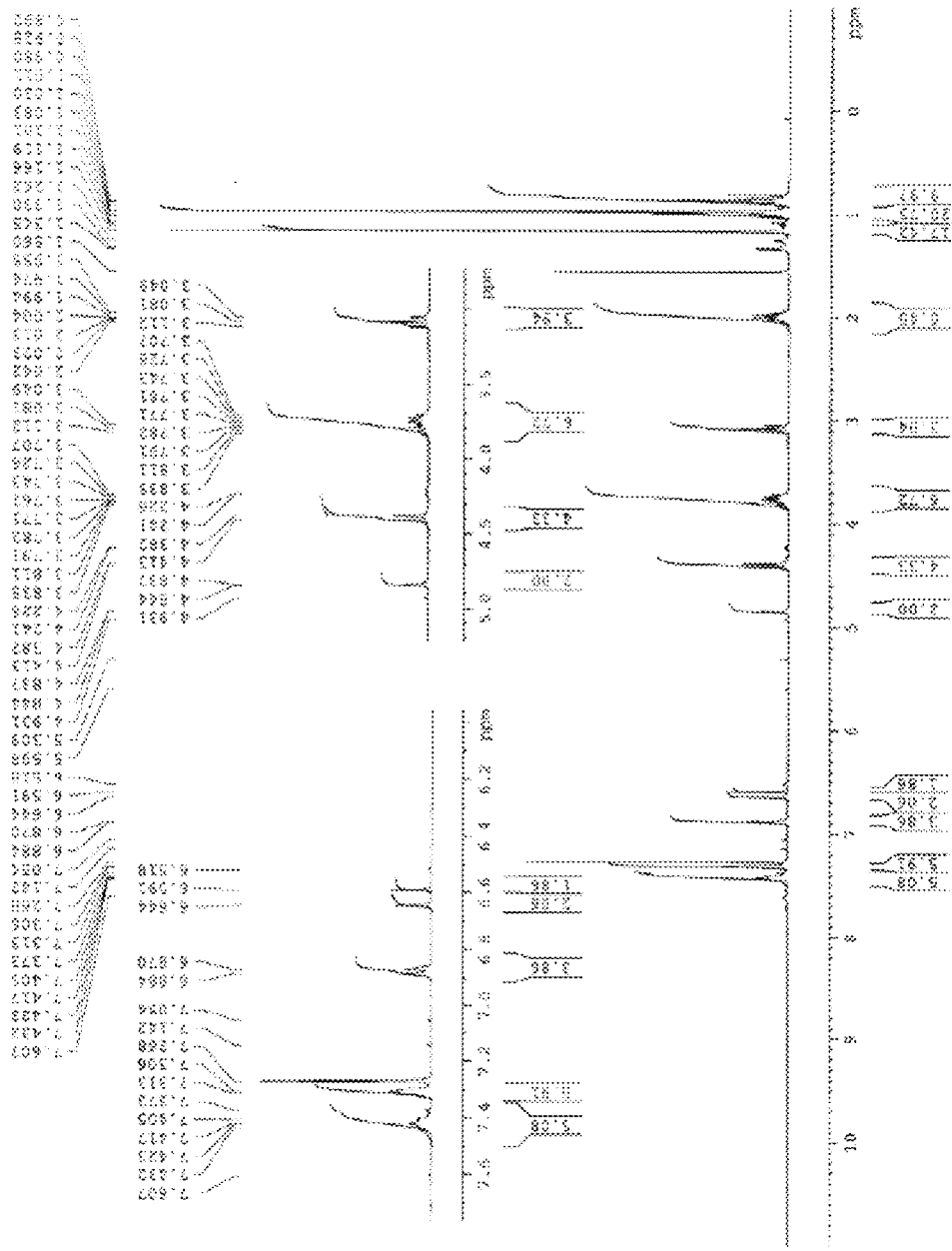
FIG. 12 shows the $^{31}$H NMR of 2.
Figure 13:
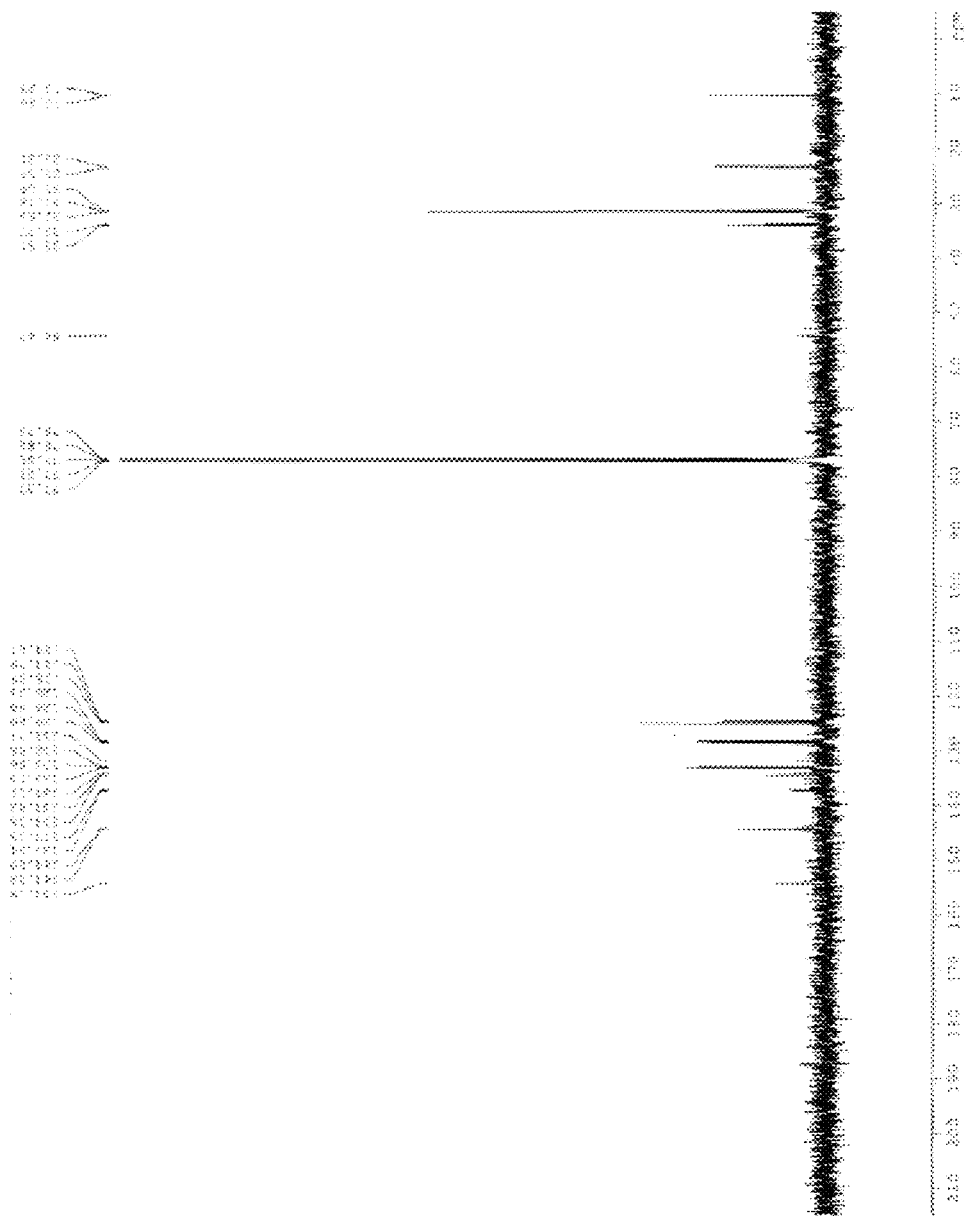
FIG. 13 shows the $^{13}$C NMR of 2.
Figure 14:
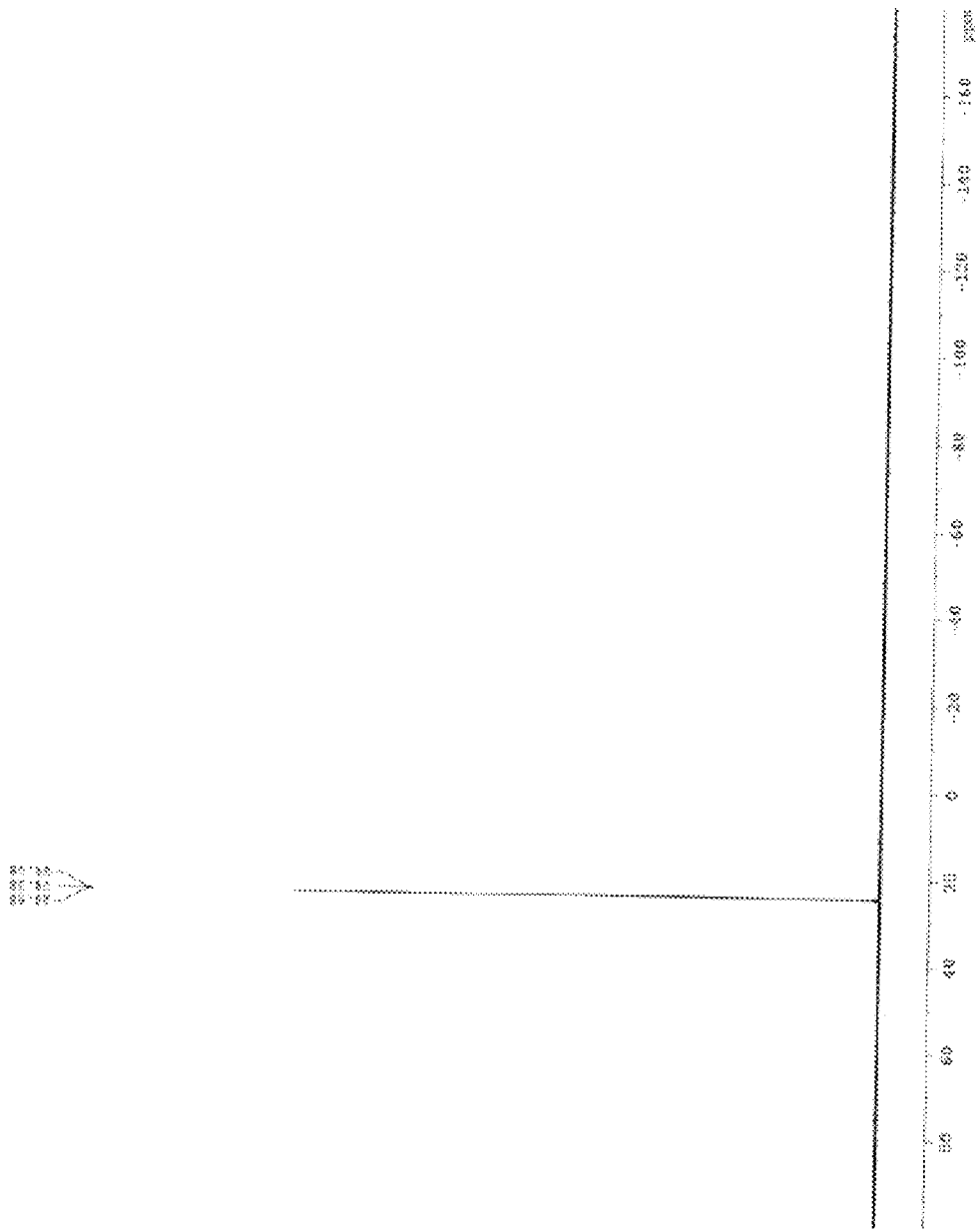
FIG. 14 shows the $^{31}$P NMR of 3.
Figure 15:
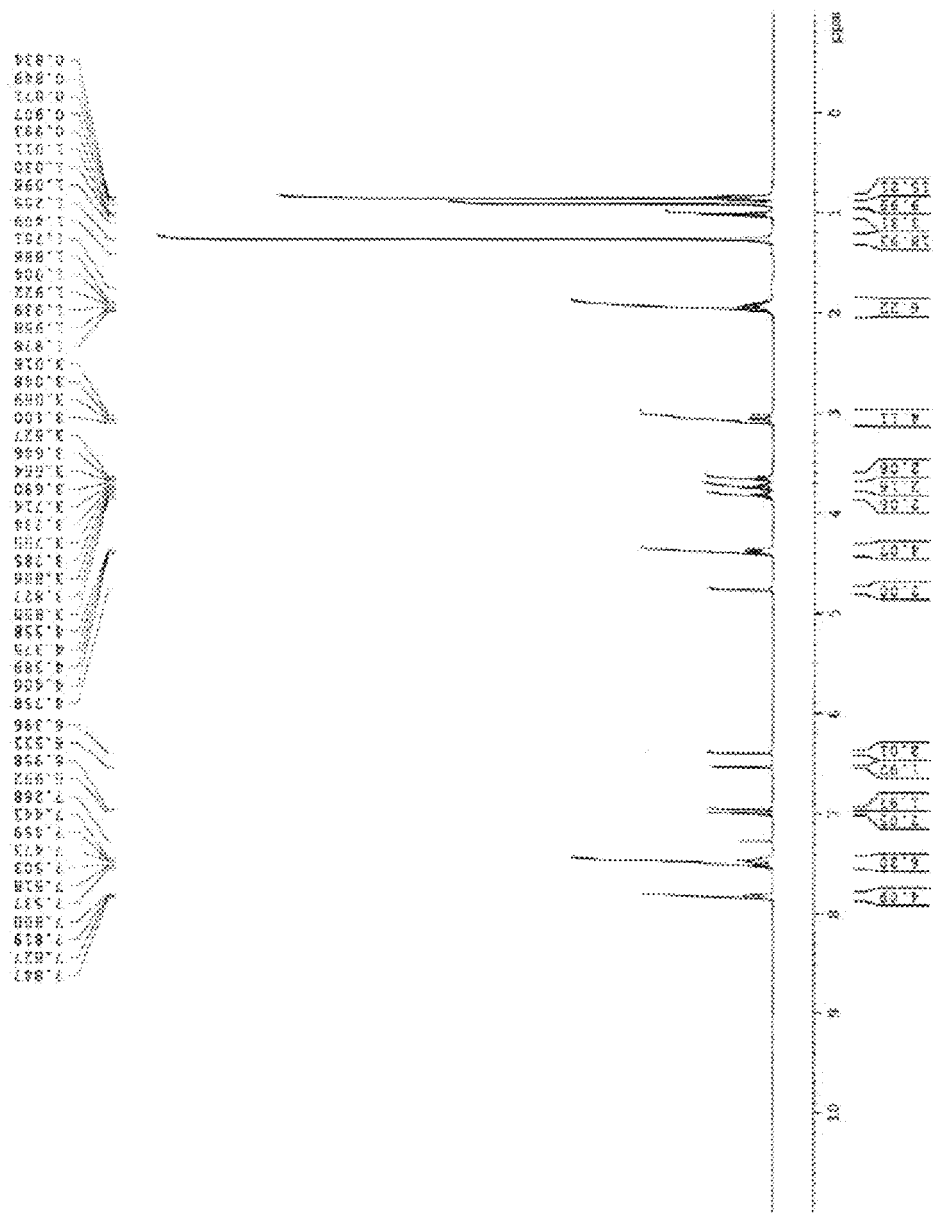
FIG. 15 shows the $^{31}$H NMR of 3.
Figure 16:
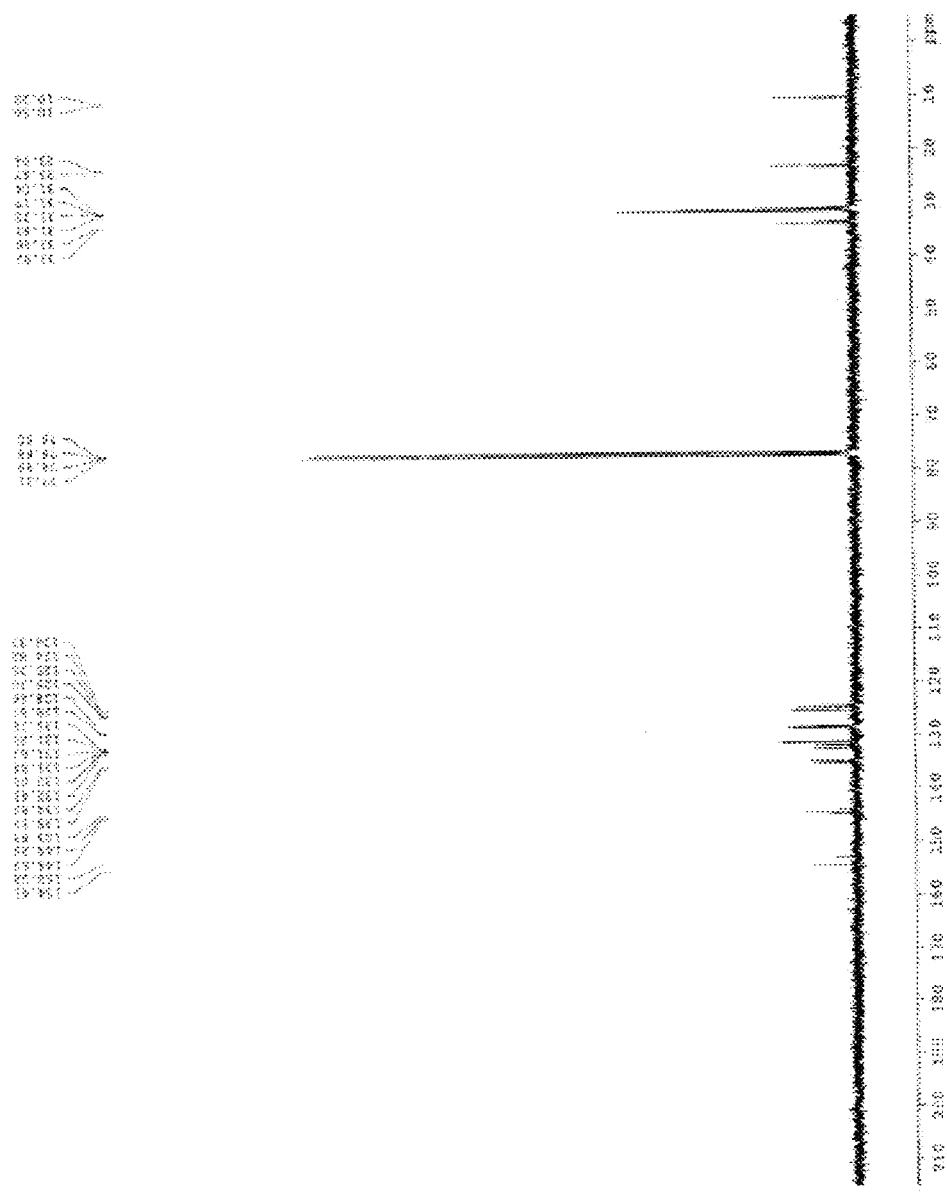
FIG. 16 shows the $^{13}C$ NMR of 3.
Figure 17:
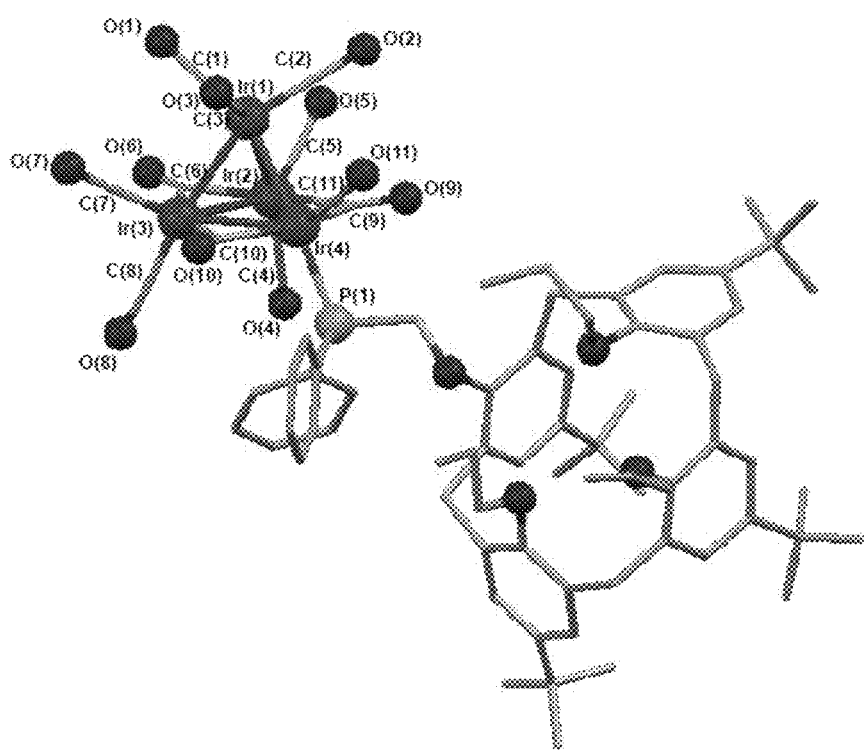
FIG. 17 shows the single crystal X-ray crystallographic structure of 1 (selected bond lengths and bond angles are depicted in Tables 1 and 2).
Figure 18:
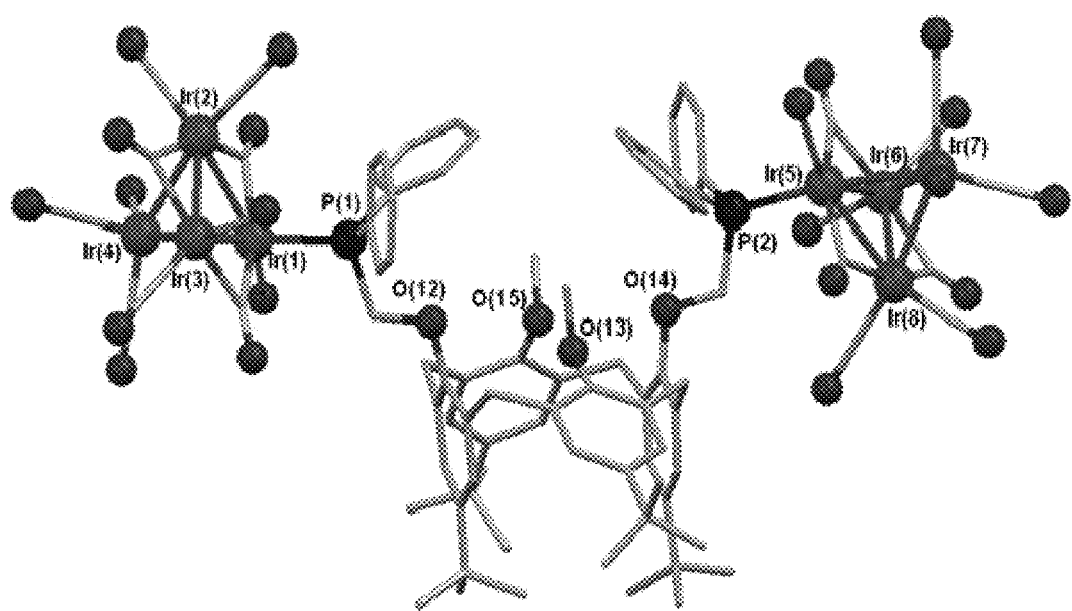
FIG. 18 shows the structure of calix[4]arene(OMe)$_2$(OCH$_2$PPh$_2$)$_2$(Ir$_4$(CO)$_{11}$)$_2$ derived from single-crystal X-ray diffraction. The Ir$_4$ metal core on the left is disordered and the positions of Ir(5), Ir(6), Ir(7) and Ir(8) atoms are shown in 90% occupancy.
Figure 19:
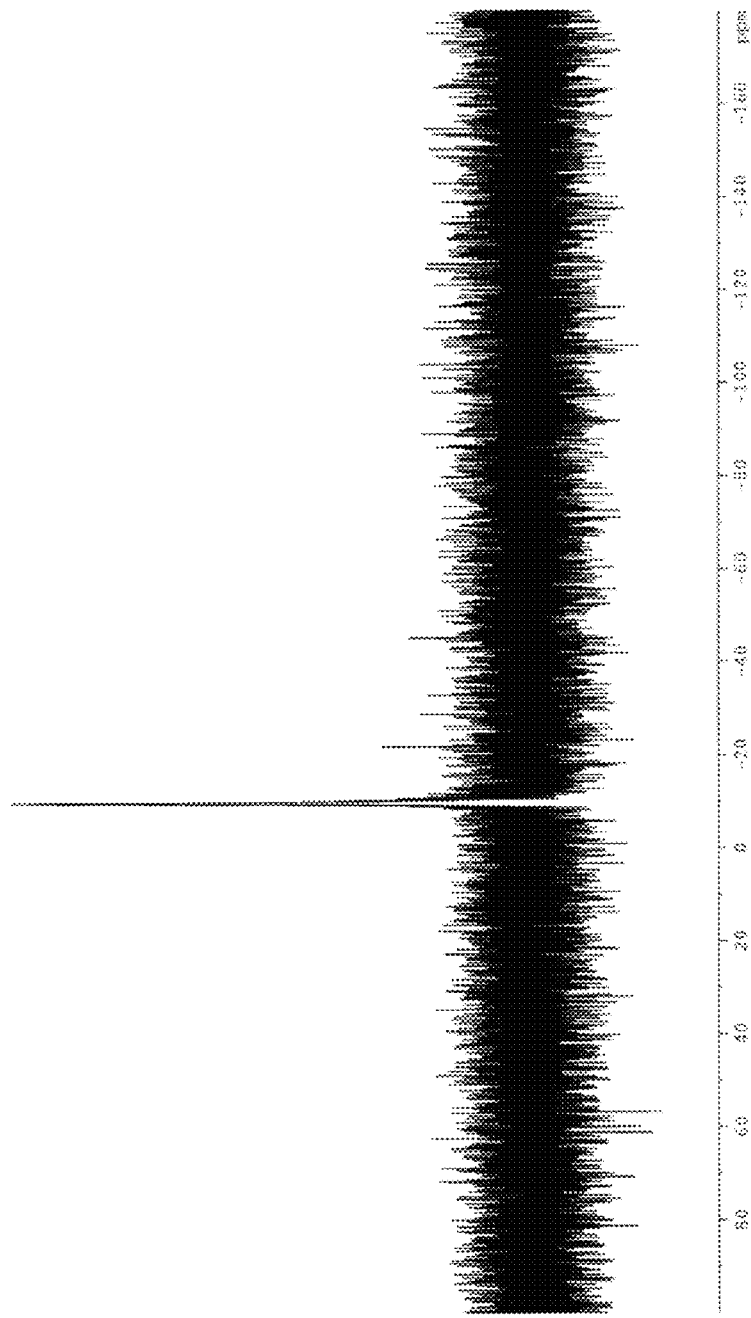
FIG. 19 shows the $^{31}P$ NMR of tert-butyl-calix[4]arene-(OPr)$_2$(OCH$_2$PPh$_2$)$_2$(Ir$_4$(CO)$_{11}$)$_2$
Figure 20:
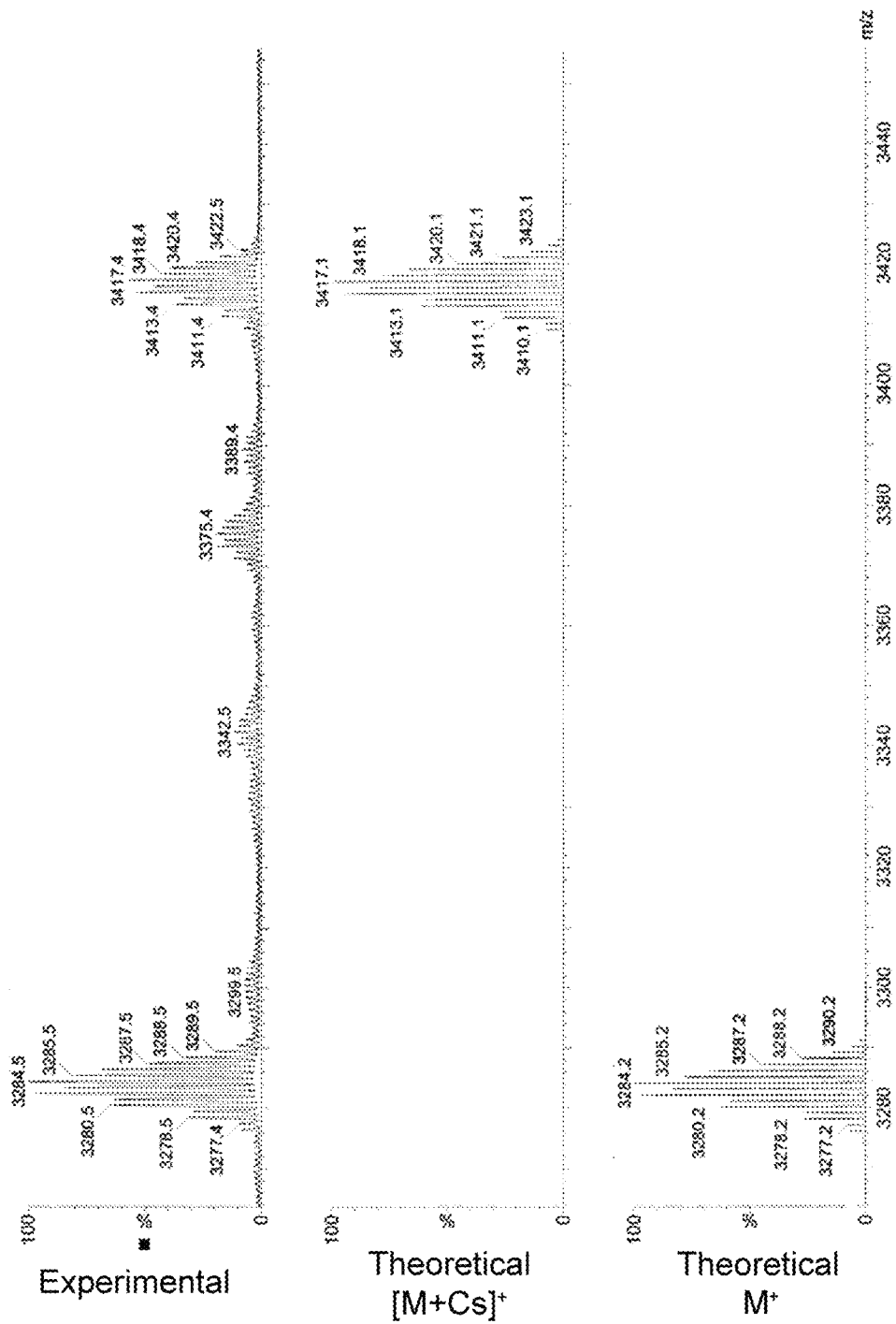
FIG. 20 shows the ESI mass spectrum of tert-butyl-calix[4]arene-(OPr)$_2$(OCH$_2$PPh$_2$)$_2$(Ir$_4$(CO)$_{11}$)$_2$
Figure 21:
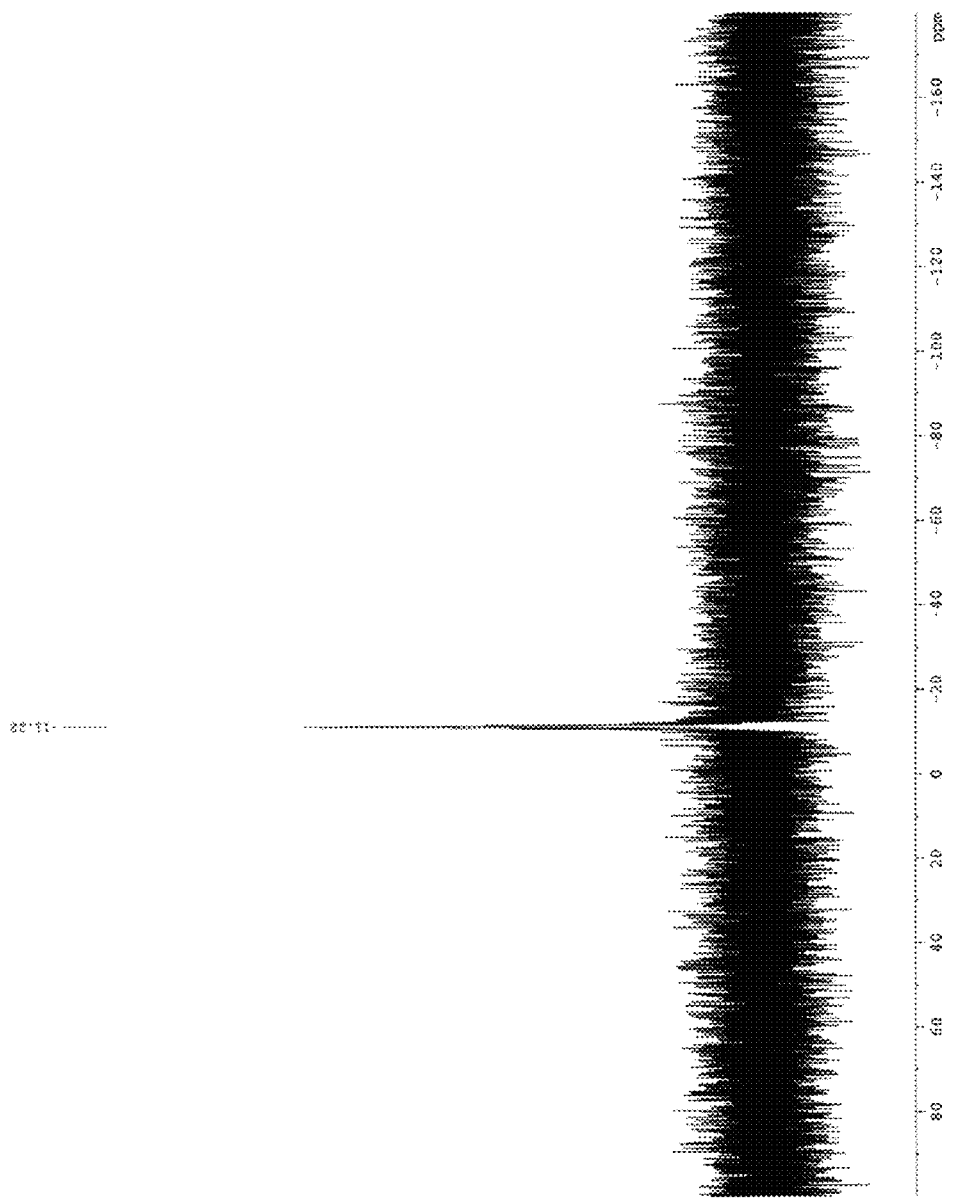
FIG. 21 shows the $^{31}P$ NMR of tert-butyl-calix[4]arene-(OMe)2(OCH$_2$PPh$_2$)$_2$(Ir$_4$(CO)$_{11}$)$_2$
Figure 22:
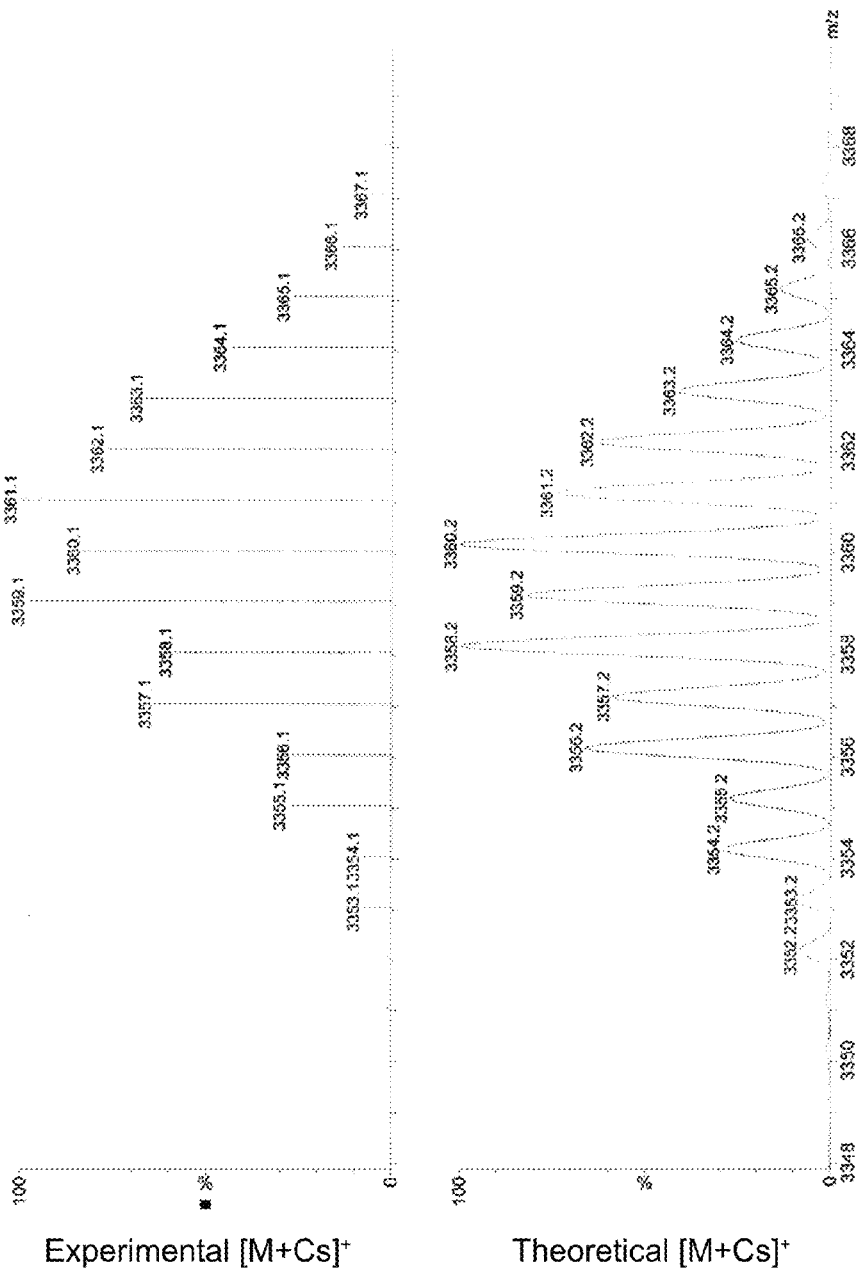
FIG. 22 shows the ESI mass spectrum of tert-butyl-calix[4]arene-(OMe)$_2$(OCH$_2$PPh$_2$)$_2$(Ir$_4$(CO)$_{11}$)$_2$
Figure 23:
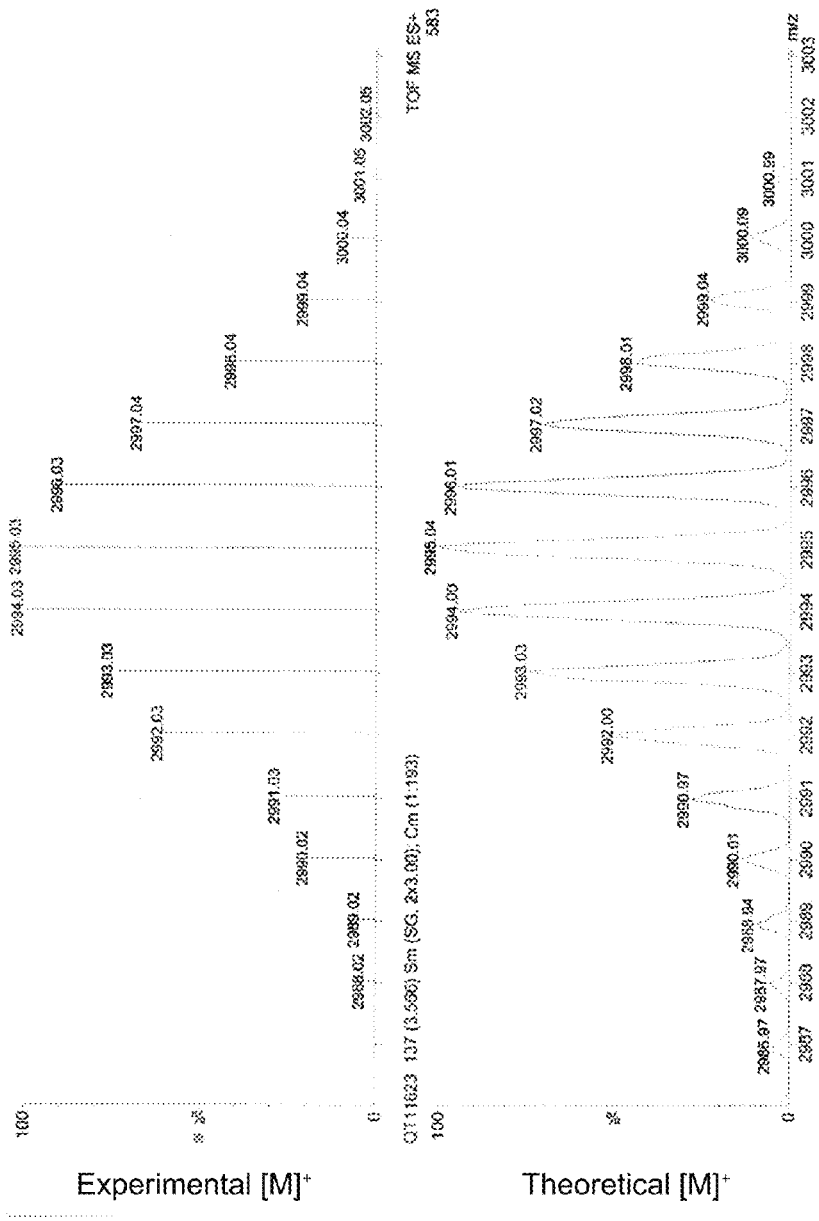
FIG. 23 shows the ESI mass spectrum of [tert-butyl-calix[4]arene-(OPr)$_3$(OCH$_2$PPh$_2$)]$_2$Ir$_4$(CO)$_{10}$.
Figure 24:
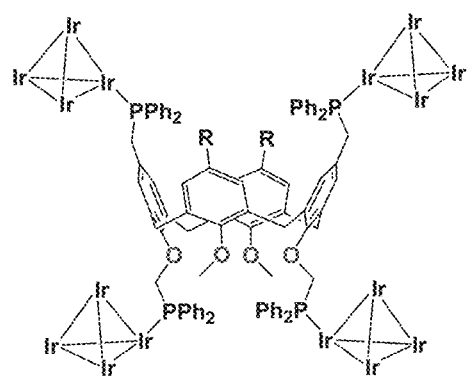
FIG. 24 shows a selection of Ir$_f$-based calixarene-bound clusters that build on the successful synthesis of the first calixarene-bound metal clusters shown above. The synthesis of structure (a) incorporates four Ir$_4$ metal cores within a molecule. Synthesis of structure (b) represents a one-dimensional polymer of repeating Ir$_4$ and calixarene units, and is an important milestone towards synthesis of metal cluster organic frameworks.
Figure 24:
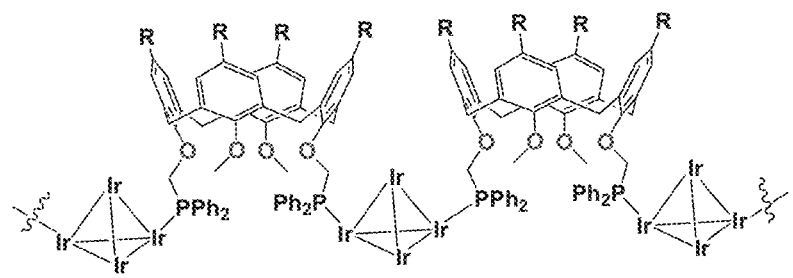
Figure 25:
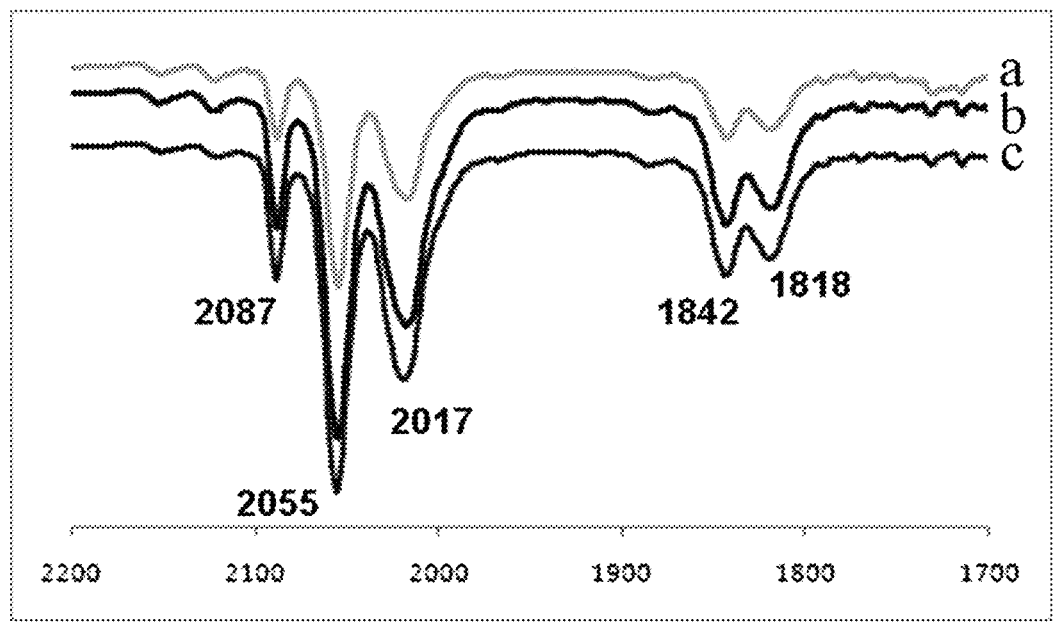
FIG. 25 shows the FTIR spectra of (a) 1, (b) tert-butyl-calix[4]arene-(OPr)$_2$(OCH$_2$PPh$_2$)$_2$(Ir$_4$(CO)$_{11}$)$_2$, and (c) tert-butyl-calix[4]arene-(OMe)$_2$(OCH$_2$PPh$_2$)$_2$(Ir$_4$(CO)$_{11}$)$_2$.
Figure 26:
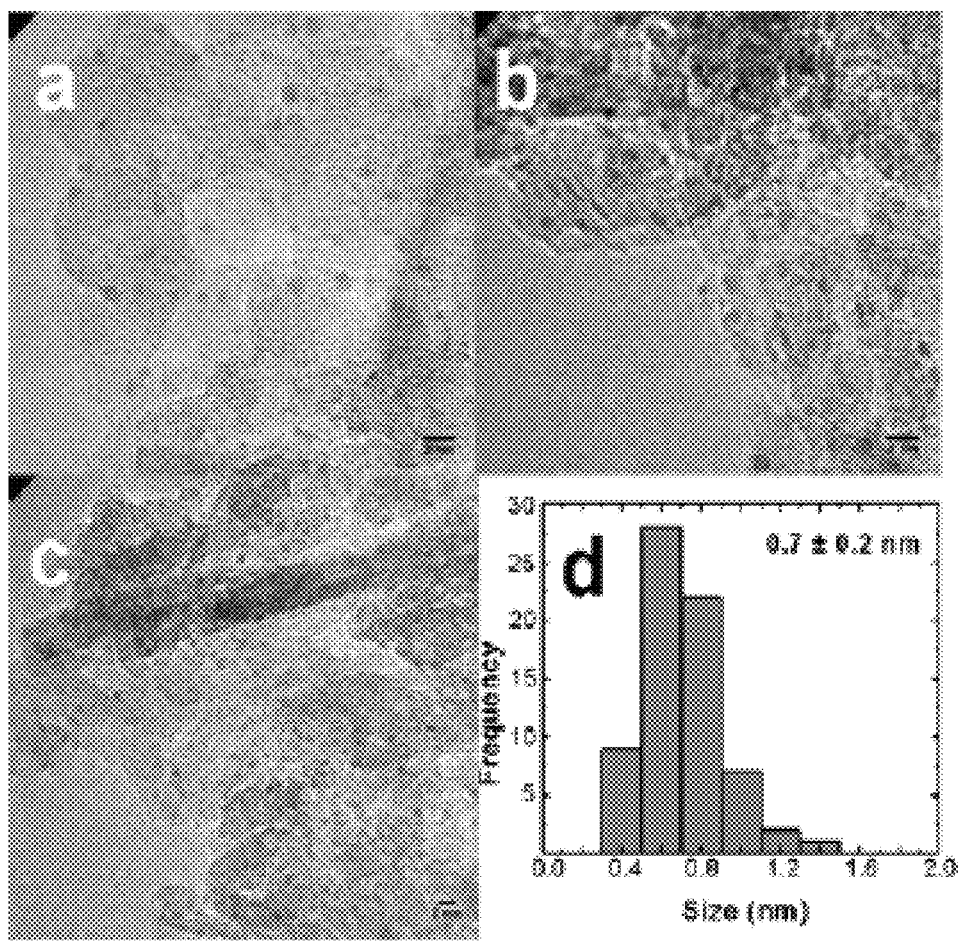
FIG. 26 shows TEM images (a, b, and c) and corresponding size distribution histograms (d) of 5 wt % Ir loaded Ir/γ-Al$_2$O$_3$ (where the alumina was purchased from Strem).
Figure 27:
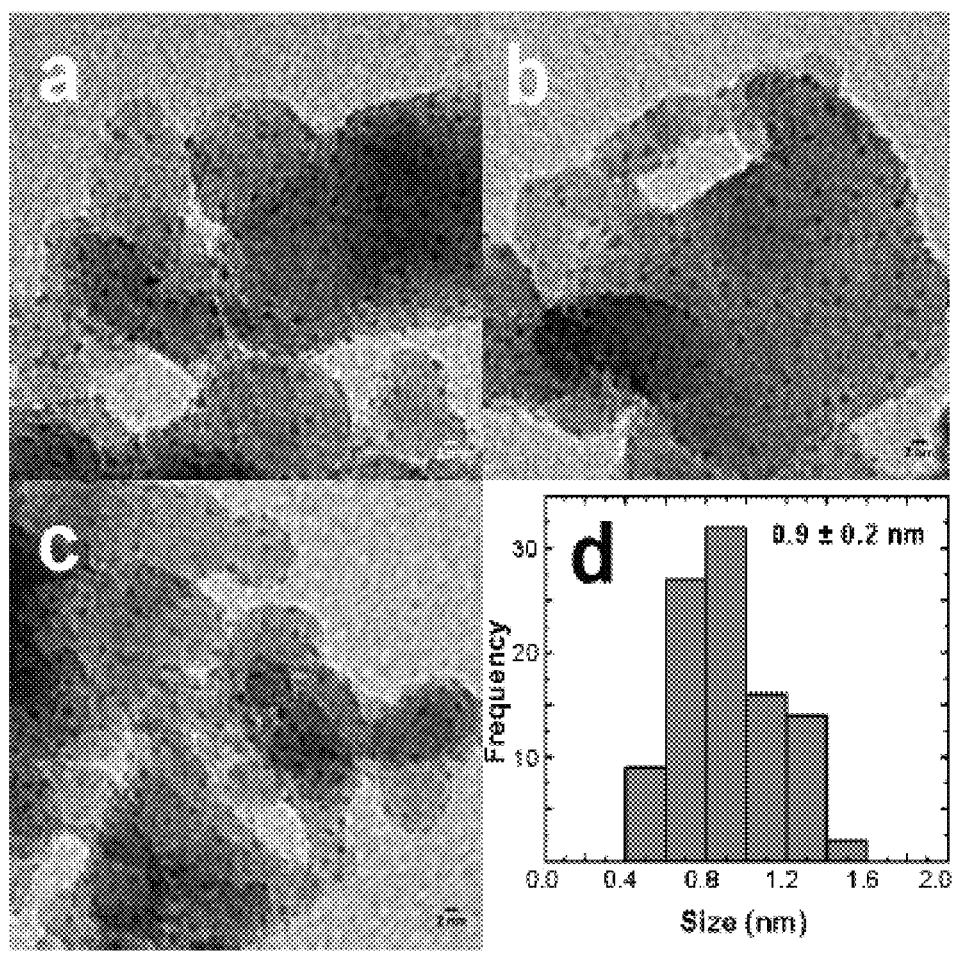
FIG. 27 shows TEM images (a, b, and c) (low resolution) and corresponding size distribution histograms (d) of 5 wt % Ir loaded Ir/γ-Al$_2$O$_3$ (where the alumina was purchased from Degussa). The Ir colloid size is slightly increased compared to the size of Ir/γ-Al$_2$O$_3$ (0.7±0.2 nm) prepared with γ-Al$_2$O$_3$ (Strem) but in error range.
Figure 28:
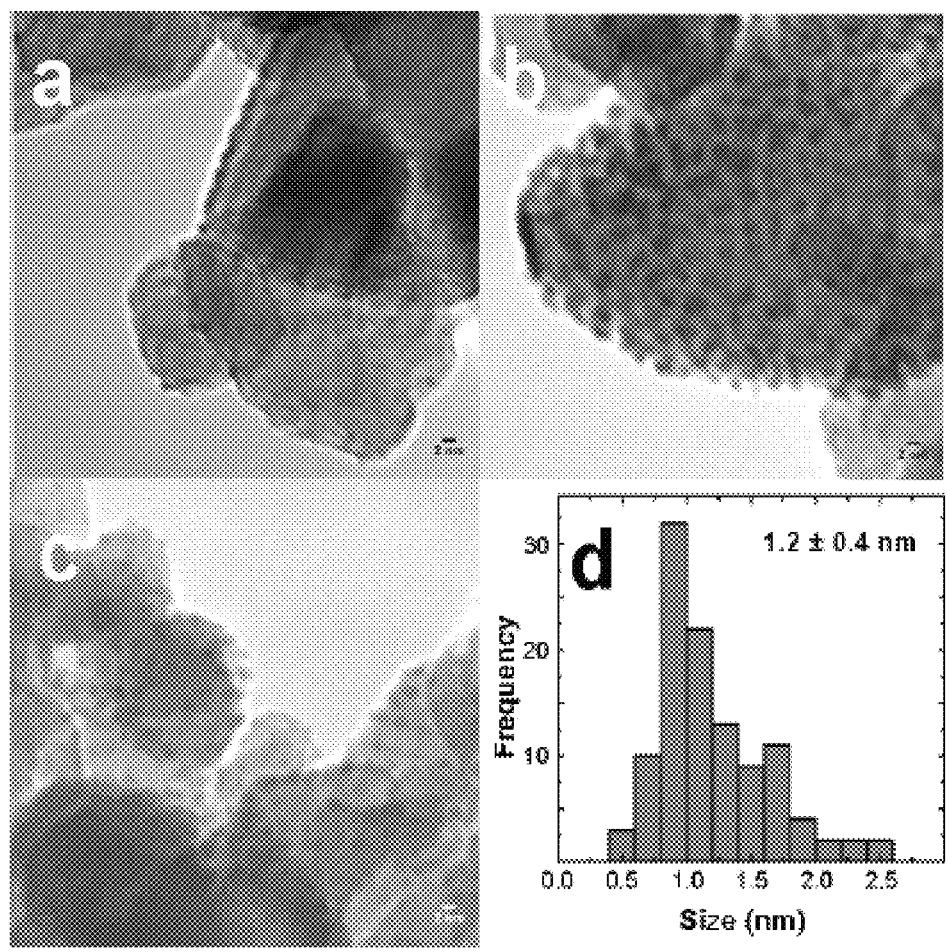
FIG. 28 shows TEM images (a, b, and c) (low resolution) and corresponding size distribution histograms (d) of 2 wt % Ir loaded Ir/TiO$_2$.
Figure 29:
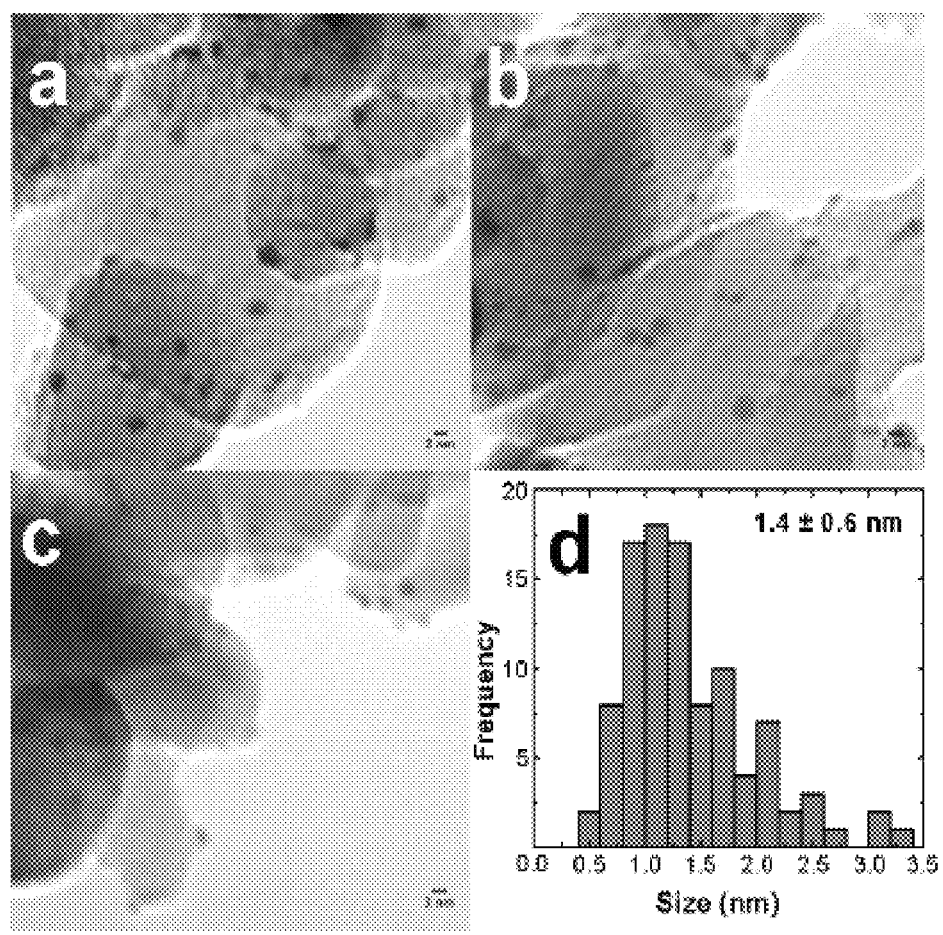
FIG. 29 shows TEM images (a, b, and c) (low resolution) and corresponding size distribution histograms (d) of 2 wt % Ir loaded Ir/MgO.

The term "alkyl," by itself or as part of another substituent, means a straight or branched chain, or cyclic hydrocarbon radical, or combination thereof, which may be fully saturated, mono- or polyunsaturated and includes mono-, di- and multivalent radicals, having the number of carbon atoms optionally designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups that are limited to hydrocarbon groups are termed "homoalkyl". The term "alkyl" can refer to "alkylene", which by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being sometimes preferred. A "lower alkyl" or "lower alkylene" is a shorter chain alkyl or alkylene group, generally having eight or fewer carbon atoms. In some embodiments, alkyl refers to any combination (including singles) selected from $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$ and $C_{30}$ alkyl. In some embodiments, alkyl refers to $C_1$-$C_{20}$ alkyl. In some embodiments, alkyl refers to $C_1$-$C_{10}$ alkyl. In some embodiments, alkyl refers to $C_1$-$C_6$ alkyl.

The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The term "heteroalkyl," by itself or in combination with another term, means, unless otherwise stated, a stable straight or branched chain, or cyclic alkyl moiety, or combinations thereof, consisting of one or more carbon atoms and at least one heteroatom selected from the group consisting of O, N, Si, B and S, and wherein the nitrogen and sulfur atoms may optionally be oxidized and the nitrogen heteroatom may optionally be quaternized. The heteroatoms O, N, S, B and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" or "heteroaryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

In some embodiments, any of alkyl, heteroalkyl, cycloalkyl, heterocycloalkyl, aryl and heteroaryl may be substituted. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents". In some embodiments, an alkyl group substituent is selected from —OR', =O, =NR', =N—OR', —NR'R', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$ in a number ranging from zero to (2m'+1), where m' is the total number of carbon atoms in such radical. In one embodiment, R', R'', R''' and R'''' each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R'', R''' and R'''' are each independently selected from hydrogen, unsubstituted alkyl, unsubstituted heteroalkyl, unsubstituted cycloalkyl, unsubstituted heterocycloalkyl, unsubstituted aryl, unsubstituted heteroaryl, alkoxy, thioalkoxy groups, and arylalkyl. In one embodiment, R', R'', R''' and R'''' are each independently selected from hydrogen and unsubstituted alkyl. When a compound of the invention includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 5-, 6-, or 7-membered ring. For example, —NR'R" can include 1-pyrrolidinyl and 4-morpholinyl. In some embodiments, an alkyl group substituent is selected from substituted or unsubstituted aryl, substituted or unsubstituted heteroaryl and substituted or unsubstituted heterocycloalkyl.

Similar to the substituents described for the alkyl radical, substituents for the aryl and heteroaryl groups are generically referred to as "aryl group substituents." In some embodiments, an aryl group substituent is selected from —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are in some embodiments independently selected from hydrogen, substituted or unsubstituted alkyl, substituted or unsubstituted heteroalkyl, substituted or unsubstituted aryl and substituted or unsubstituted heteroaryl. In some embodiments, R', R", R''' and R'''' are independently selected from hydrogen, unsubstituted alkyl, unsubstituted heteroalkyl, unsubstituted aryl and unsubstituted heteroaryl. In some embodiments, R', R", R''' and R'''' are independently selected from hydrogen and unsubstituted alkyl. When a compound of the invention includes more than one R group, for example, each of the R groups is independently selected as are each R', R", R' and R'''' groups when more than one of these groups is present. In some embodiments, an aryl group substituent is selected from substituted or unsubstituted alkyl, substituted or unsubstituted heteroalkyl, substituted or unsubstituted heterocycloalkyl, substituted or unsubstituted aryl and substituted or unsubstituted heteroaryl.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

The term "heteroatom" includes oxygen (O), nitrogen (N), sulfur (S), silicon (Si) and boron (B).

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers and d and l isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are included.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

EMBODIMENTS

In one aspect, the invention provides metal colloids, calixarene-related compounds and complexes thereof. In one aspect, a complex comprises: (a) a metal colloid comprising a plurality of metal atoms; and (b) a calixarene-related compound comprising a linker, wherein the linker comprises a coordinating atom coordinated to one of the plurality of metal atoms. Useful metal atoms for the metal colloid include those selected from Ir, Pt, Pd, Ni, Mo, W, and Co, and an exemplary metal atom is Ir.

The term "calixarene-related compound" is meant to include calixarenes and compounds similar to calixarene in that they contain aryl or heteroaryl groups linked by bridging moieties to form a "basket", as well as "basket"-type compounds formed by similarly linking other cyclic groups. The text "Calixarenes Revisited" (C. David Gutsche, Royal Society of Chemistry, 1998) describes some of these compounds, for instance on pp. 23-28, and this text is hereby incorporated by reference herein. "Calixarene-related compounds" is meant to include the types of compounds mentioned in that text. It thus includes compounds referred to as "homocalixarenes", in which one or more bridges between the phenolic groups contain two or more carbon atoms. One example given in Gutsche is no. 62, which includes cyclobutyl bridges.

"Calixarene-related compounds" also includes, for example, oxacalixarenes, azacalixarenes, silicacalixarenes and thiacalixarenes, which contain one or more oxygen, nitrogen, silicon or sulfur bridges, respectively, between phenolic groups, as well as calixarene compounds having one or more platinum bridges. This term also includes compounds such as those termed "calixarene-related cyclooligomers" in Gutsche (1998), for instance similar structures formed from furan or thiophene rather than phenolic residues. Other calixarene-related compounds include, for example, calix[n]pyrroles, calix[m]pyridino[n]pyrroles or calix[m]pyridine. A "calix[n]pyrrole," is a macrocycle having "n" pyrrole rings linked in the α-positions. "Calix[m]pyridino[n]pyrroles" are macrocycles having "m" pyridine rings and "n" pyrrole rings linked in the α-positions. A "calix[m]pyridine" is a macrocycle having "m" pyridine rings linked in the α-positions.

The framework of the calixarene ligand can be substituted with other atoms that do not interfere with the ability of the ligand to form complexes with transition metals. For example, the framework of the calixarene ligand can be substituted with alkyl, aryl, halide, alkoxy, thioether, alkylsilyl, or other groups.

Exemplary calixarene-related compounds have four, six, or eight phenolic moieties; thus preferred calixarenes are calix[4]arenes, calix[6]arenes, and calix[8]arenes. Calix[4]arenes are more preferred. In some preferred catalyst systems, the calixarene ligand is a p-alkylcalixarene, more preferably a p-t-butylcalixarene. The synthetic procedures for making these materials have been finely honed and optimized, and the starting materials, e.g., p-t-butylphenol, are readily available.

Exemplary calixarene-related compounds are calixarenes, which are cyclic oligomers of phenol and substituted phenols condensed with formaldehyde, and are characterized by the general structure:

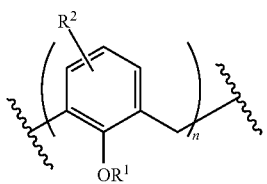

in which n is 3, 4, 5, 6, 7, 8, 9, 10, 11, 12, 13, 14, 15 or 16 in various embodiments. In exemplary embodiments, n is 4. The wavy lines represent the attachment of a plurality of these monomeric units to form a closed ring. General information about such molecules can be found, for example in Bauer et al., *JACS* 107, 6053 (1985) and the texts "Calixarenes" by C. David Gutsche, which is part of the Monographs in Supramolecular Chemistry (J. Fraser Stoddart, ed.; Royal Society of Chemistry, 1989) and "Calixarenes Revisited" (1998) by the same author. Calixarenes are in the form of a cyclical oligomer having a "basket" shape, where the cavity can serve as a binding site for numerous guest species, including ions and molecules.

In some embodiments, the group $R^2$ may be hydrogen, or may be any of a number of aryl substituent groups including, but not limited to, alkyl, alkenyl, alkynyl, allyl, aryl, heteroaryl, alcohol, sulfonic acid, phosphine, phosphine oxide, phosphonate, phosphonic acid, thiol, ketone, aldehyde, ester, ether, amine, quaternary ammonium, imine, amide, imide, imido, nitro, carboxylic acid, disulfide, carbonate, isocyanate, carbodiimide, carboalkoxy, carbene, sulfoxide, phosphonium, carbamate, acetal, ketal, boronate, cyanohydrin, hydrazone, oxime, oxazole, oxazoline, oxalane, hydrazide, enamine, sulfone, sulfide, sulfenyl and halogen. In exemplary calixarenes, $R^2$ typically represents a single substituent at the position para to the $OR^1$ group. However, calixarenes of use in the present invention can include one or more $R^2$ substituent. When more than one substituent is present, the substituents can be the same or different. An exemplary class of calixarene compounds with two substituents is known in the art as the calix[n]resorcinarenes, which comprise resorcinol moieties that are joined to each other, and typically possess phenoxy groups in a different arrangement around the ring.

Exemplary $R^1$ substituents include substituted or unsubstituted alkyl, substituted or unsubstituted heteroalkyl, substituted or unsubstituted aryl and substituted or unsubstituted heteroaryl moieties. $R^1$ can also be H.

In exemplary embodiments, at least one $R^1$ comprises one or more coordinating atoms. A "coordinating atom" is a component that is capable of coordinating (or forming a coordinate bond) with a metal atom, especially a metal atom of a metal colloid. Exemplary "coordinating atoms" include nitrogen, oxygen, sulfur, phosphorus and carbon (for example, as in carbene). The coordinating atom can be neutral or charged, e.g., a component of a salt or derived therefrom.

A "calixarene-related moiety" is a structure derived from a "calixarene-related compound or molecule" by its coordination to a metal colloid through a linker comprising a coordinating atom.

The term "metal colloid" refers to a species of metal particle composed of at least two metal atoms, which can be the same or different metal. A metal colloid typically includes at least one other organic ligand (e.g., CO). Multiple ligands on a metal colloid can be the same or different. The colloid can include two or more calixarene-related moieties, and these moieties can be the same or different.

Thus, in a further exemplary aspect, the invention provides a complex comprising a metal colloid complexed to a calixarene-related moiety. An exemplary compound of the invention has the structure:

$$M\text{-}L\text{-}C$$

in which M is a metal colloid and L is a zero- or higher-order linker joining the metal colloid to C, the calixarene-related moiety.

In exemplary embodiments, a complex comprises: (a) a metal colloid comprising a plurality of iridium atoms; and (b) a calixarene-related compound comprising a linker, wherein the linker comprises a coordinating atom coordinated to one of the plurality of iridium atoms.

In any embodiment described herein, the calixarene-related compound has the formula:

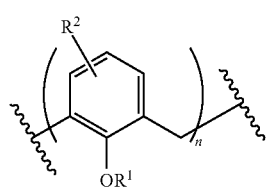

wherein n is an integer selected from 3, 4, 5, 6, 7, 8, 9, 10, 11, 12, 13, 14, 15 and 16. In some embodiments, n is an integer selected from 4, 5, 6, 7 and 8. In exemplary embodiments, n is 4.

In some embodiments, R¹ is a moiety selected from substituted or unsubstituted alkyl, substituted or unsubstituted heteroalkyl, substituted or unsubstituted aryl, substituted or unsubstituted heteroaryl, and a linker. In exemplary embodiments, at least one R¹ comprises a coordinating atom. In some embodiments, R¹ is substituted or unsubstituted alkyl. In some embodiments, R¹ is selected from $C_1$, $C_2$, $C_3$, $C_4$, $C_5$ or $C_6$ alkyl. In some embodiments, R¹ is propyl. In some embodiments, R¹ is methyl. In some embodiments, R¹ is H.

In some embodiments, R² is a moiety selected from hydrogen, substituted or unsubstituted alkyl, substituted or unsubstituted aryl, substituted or unsubstituted heteroaryl, alcohol, sulfonic acid, phosphine, carbene, phosphonate, phosphonic acid, phosphine oxide, thiol, sulfoxide, ketone, aldehyde, ester, ether, amine, quaternary ammonium, phosphonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, halogen and a combination thereof. In some embodiments, R² is substituted or unsubstituted alkyl. In some embodiments, R² is selected from $C_1$, $C_2$, $C_3$, $C_4$, $C_5$ and $C_6$ alkyl. In some embodiments, R² is tert-butyl. In some embodiments, R² is in the para position relative to —OR¹.

In exemplary embodiments, at least one R¹ is the linker. The term "linker" as used herein refers to a single covalent bond ("zero-order") or a series of stable covalent bonds incorporating 1-30 nonhydrogen atoms selected from the group consisting of C, N, O, S, Si, B and P that covalently link together the components of the invention disclosed herein, e.g., linking a solid support to a calixarene-related compound, or linking a calixarene-related compound to a metal colloid. Exemplary linkers include 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 non-hydrogen atoms. Unless otherwise specified, "linking," "linked," "linkage," "conjugating," "conjugated" and analogous terms relating to attachment refer to techniques utilizing and species incorporating linkers. A calixarene-related compound can comprise multiple linkers, thus conferring higher levels of denticity.

In some embodiments, a linker is a moiety selected from phosphine, substituted or unsubstituted alkyl, substituted or unsubstituted heteroalkyl, substituted or unsubstituted aryl and substituted or unsubstituted heteroaryl.

In exemplary embodiments, a linker comprises a coordinating atom. In exemplary embodiments, the coordinating atom is selected from phosphorus, carbon, nitrogen and oxygen. Coordinating atoms can be provided through a large number of various moieties known in the art. For convenience, these moieties can be referred to as P-, C-, N- and O-containing moieties.

In exemplary embodiments, a linker is a P-containing moiety. One particularly useful P-containing moiety is phosphine. In various exemplary embodiments, the coordinating atom on the linker is the phosphorus atom of a phosphine moiety. In some embodiments, the term "phosphine" generically refers to —Y¹P(Y²)(Y³), wherein Y¹ is selected from a bond, substituted or unsubstituted alkyl, substituted or unsubstituted heteroalkyl, substituted or unsubstituted aryl and substituted or unsubstituted heteroaryl; and Y² and Y³ are independently selected from substituted or unsubstituted alkyl, substituted or unsubstituted heteroalkyl, substituted or unsubstituted aryl and substituted or unsubstituted heteroaryl. In some embodiments, Y² and Y³ are each substituted or unsubstituted aryl. In exemplary embodiments, Y² and Y³ are each phenyl. In some embodiments, Y¹ is substituted or unsubstituted alkyl. In some embodiments, Y¹ is $C_1$, $C_2$, $C_3$, $C_4$, $C_5$ or $C_6$ alkyl. In some embodiments, Y¹ is methyl. In some embodiments, Y¹ is a bond.

Similar to phosphine ligands, phosphinite, phosphonite and phosphites have recently emerged as versatile ligands in transition metal catalyzed reactions. Positioning of adjacent electronegative heteroatoms such as N and O (but not limited thereto) allow subtle modulation of electronic properties of these ligands that are often beneficial to catalytic reactions. The presence of adjacent O and N provides additional oxidative stabilities to these ligands compared to their phosphine analogues. These ligands are easy to make in high yield due to availability of large natural and synthetic chiral pool derived amino alcohols and chiral diols (for a modular approach, see Velder, J.; Robert, T.; Weidner, I.; Neudorfl, J.-M.; Lex, J.; Schmalz, H-G. *Adv. Synth. Catal.* 2008, 350, 1309-1315; for a review on synthesis of phosphites, see Montserrat Diéguez, Oscar Pámies, Aurora Ruiz, and Carmen Claver, *Methodologies in Asymmetric Catalysis*, Chapter 11, 2004, pp 161-173 *ACS Symposium Series*, Volume 880 for synthesis of phosphites. See Adriaan J. Minnaard, Ben L. Feringa, Laurent Lefort and Johannes G. de Vries *Acc. Chem. Res.*, 2007, 40 (12), pp 1267-1277 for the synthesis of phosphoramidites)

Examples where phosphinite ligands have been used are Rh catalyzed asymmetric hydrogenation of olefin (Blankenstein, J.; Pflatz, A. *Angew Chem. Int. Ed.*, 2001, 40, 4445-47) and Pd catalyzed Suzuki cross coupling reaction (Punji, B.; Mague, J. T.; Balakrishna, M. S. *Dalton Trans.*, 2006, 1322-1330).

Pflatz and coworkers used an oxazoline based phosphonite ligand for Ru catalyzed asymmetric cyclopropanation of styrene using ethyl diazoacetate as carbene source. The same catalyst was also capable of transfer hydrogenation reaction in the presence of 2-propanol and corresponding sodium alkoxide (Braunstein, P.; Naud, F.; Pflatz, A.; Rettig, S. *Organometallics*, 2000, 19, 2676-2683). Pringle, Ferringa and coworkers have shown enantioselective conjugate addition of diethyzinc to enones with Cu(I)-phosphonite based catalyst (Martorell, A.; Naasz, R.; Ferringa, B. L.; Pringle, P. G. *Tetrahedron Asymmetry*, 2001, 12, 2497-2499). Ding and coworkers have used ferrocene based bidentate phosphonite ligands for enantioselective hydroformylation reactions. (Peng, X.; Wang, Z.; Xia, C.; Ding, K. *Tetrahedron Lett.*, 2008, 49, 4862-4864)

Rajanbabu and coworkers have used nickel phosphinite, phosphite and phosphoramidite ligands for asymmetric hydrovinylation reaction (Park, H.; Kumareswaran, R.; Rajanbabu, T. V. R. *Tetrahedron*, 2005, 61, 6352-67). Sandoval et al., have used Rh(I) diphosphite ligands for asymmetric hydrogenation of dehydroamino acid derivatives (Sandoval, C. A.; Liu, S. *J. Molecular. Catalysis. A*, 2010, 325, 65-72). Pd phosphite catalyzed dehalogenation of arenes was reported by Lee et al., (Moon, J.; Lee, S. *J. Organometal. Chem.*, 2009, 694, 473-77). Pd-triphenyl phosphite was shown to catalyze dehydrative allylation using allyl alcohol (Kayaki, Y.; Koda, T.; Ikariya, T. *J. Org. Chem.*, 2004, 69, 2595-97). Pd-based biaryl phosphite catalyst is known to be effective in asymmetric allylic substitution reactions of allyl acetate, carbonate and halides (Dieguez, M.; Pamies, O. *Acc. Chem. Res.*, 2010, 43, 312-22). Calixarene phosphites have been used as hemispherical chelator ligands for obtaining high linear to branched ratio of olefin in Rh(0) catalyzed hydroformylation reaction (Monnereau, L.; Semeril, D.; Matt, D.; Toupet, L. *Adv. Synth. Catal.* 2009, 351, 1629-36)

Phosphoramidite ligands have been used in catalytic asymmetric hydrogenations (Minnaard, A. J.; Feringa, B. L.; Lefort, L.; de Vries, J. G. *Acc. Chem. Res.*, 2007, 40, 1267-77), conjugate addition to enones (Jagt, R. B. C.; de Vries, J.

G.; Ferringa, B. L.; Minnaard, A. *J. Org. Lett.*, 2005, 7, 2433-35), and allylic alkylation with diethyl zinc (Malda, H.; van Zijl, A. W.; Arnold, L. A.; Feringa, B. L. *Org. Lett.*, 2001, 3, 1169-1171).

Accordingly, in some embodiments, a linker is selected from phosphinite, phosphonite, phosphite and phosphoramidite. In some embodiments, a linker comprises any of these moieties. For example, a linker can be an alkyl (e.g., $C_1$, $C_2$, $C_3$, $C_4$, $C_5$ or $C_6$ alkyl), heteroalkyl, aryl or a heteroaryl that is substituted by any of these moieties.

In some embodiments, a linker is a C-containing moiety. In some embodiments, a linker is a carbene. Particularly useful carbenes include Arduengo carbenes. One example is a diaminocarbene with the general formula: C(R'N)(R''N), where R' and R'' are various functional groups (such as R generically described above) that are optionally bridged to form a heterocycle, such as imidazole or triazole. In exemplary embodiments, a carbene is an alkyl (e.g., $C_1$, $C_2$, $C_3$, $C_4$, $C_5$ or $C_6$ alkyl) substituted by an imidazolium moiety. In some embodiments, the carbene is methyl substituted by an imidazolium moiety. In some embodiments, a linker comprises any of these moieties. For example, a linker can be an alkyl (e.g., $C_1$, $C_2$, $C_3$, $C_4$, $C_5$ or $C_6$ alkyl), heteroalkyl, aryl or a heteroaryl that is substituted by any of these moieties.

In exemplary embodiments, a linker is an N-containing moiety. Various useful N-containing moieties include amine (Inorganica Chimica Acta, 2005, 358, 2327-2331), isonitrile (Organometallics, 1994, 13: 760-762), bis(pyrazol-1-yl)methane (Dalton Trans., 2004, 929-932, for example of a complex with Pd—similar complexes are possible with Ir), pyridine (Dalton Trans., 2003, 2680-2685 describing example of pyridine-gold complex—another noble metal like Ir), bipyridine (Inorganic Chemistry, 2008, 47(12): 5099-5106, describing calixarene-based bipyridine complexes involving platinum—another noble metal like Ir as well as Inorganica Chimica Acta, 1989, 165: 51-64 describing bipyridine complex involving gold—another noble metal like Ir), terpyridine (see J. Am. Chem. Soc. 1999, 121: 5009-5016 for example of iridium terpyridine complex), tetramethylethylinediamine (TMEDA) (Inorganic Chemistry, 2003, 42(11): 3650-61 for Pd complex with TMEDA—similar complexes are anticipated for iridium metal), and 1-10-phenanthroline (see Inorganic Chemistry, 2003, 42(11): 3650-61 for Pd complex with 1-10-phenanthroline—similar complexes are anticipated for iridium metal). Other N-containing moieties include amide, amine, amine oxide, nitroso, nitro, carbamate and pyrazole. In some embodiments, a linker comprises any of these moieties. For example, a linker can be an alkyl (e.g., $C_1$, $C_2$, $C_3$, $C_4$, $C_5$ or $C_6$ alkyl), heteroalkyl, aryl or a heteroaryl that is substituted by any of these moieties.

In exemplary embodiments, a linker is an O-containing moiety. Various useful O-containing moieties include alkoxide (Dalton Trans., 2004, 929-932 for example of a complex with Pd—similar complexes are possible with Ir), hydroxide (Inorganic Chemistry, 2003, 42(11): 3650-61 for example of hydroxide complex of Pd—similar complexes are possible for Ir), phenoxide (phenoxy would be native to all calixarene lower-rim ROH groups as a ligand), acetylacetonate (acac) (Polyhedron, 2000, 19: 1097-1103), carboxylate (Inorg. Chem. 1993, 32: 5201-5205 for carboxylate-Ir complex and Dalton Trans. 2003, 2680-2685 and Verlag der Zeitschrift fur Naturforschung, 2002, 57b: 605-609 describing example of carboxylate-gold complex—another noble metal like Ir), carbon dioxide and carbonate (J. Am. Chem. Soc. 1989, 111: 6459-6461). Other O-containing moieties include peroxo, ester and ether. In some embodiments, a linker comprises any of these moieties. For example, a linker can be an alkyl (e.g., $C_1$, $C_2$, $C_3$, $C_4$, $C_5$ or $C_6$ alkyl), heteroalkyl, aryl or a heteroaryl that is substituted by any of these moieties.

In some embodiments, the linker is a moiety selected from alkyl and heteroalkyl, which is optionally substituted with one or more alkyl group substituents, as described herein, in addition to the coordinating atom. In some embodiments, the linker is substituted with a moiety selected from alcohol, sulfonic acid, phosphine, phenyl, imidazolium, carbene, phosphonate, phosphonic acid, phosphine oxide, thiol, sulfoxide, ketone, aldehyde, ester, ether, amine, quaternary ammonium, phosphonium, imine, amide, imide, imido, nitro, carboxylic acid, disulfide, carbonate, isocyanate, carbodiimide, carboalkoxy, carbamate, acetal, ketal, boronate, cyanohydrin, hydrazone, oxime, oxazole, oxazoline, oxalane, hydrazide, enamine, sulfone, sulfide, sulfenyl, halogen and a combination thereof.

In some embodiments, calixarene-related compounds are functionalized with one or more linker. In various embodiments, the linkers include one or more coordinating atom that is capable of coordinating to at least one metal atom. The linker-functionalized calixarene-related compounds can be prepared by art-recognized methods. For example, in various embodiments, the calixarene-related compound includes at least one phenol subunit. The phenol hydroxyl is deprotonated and the phenoxide ion is reacted with a linker precursor having a reactive functional group with reactivity complementary to that of the phenoxide ion, thereby functionalizing the phenol oxygen atom of the calixarene-related compound. As those of skill in the art will appreciate, reactive functional groups other than phenols can function as substituents on calixarene-related compounds and can serve as attachment points for linkers.

Exemplary reactive functional groups of use in forming linker-functionalized calixarene-related compounds of the invention are set forth below.

In some embodiments, the core of the calixarene-related compound and the linker are joined by reaction of a first reactive functional group on the calixarene-related core and a second reactive functional group on a precursor of the linker. The reactive functional groups are of complementary reactivity, and they react to form a covalent link between two components compound.

Exemplary reactive functional groups can be located at any position on these precursors, e.g., an alkyl or heteroalkyl an aryl or heteroaryl nucleus or a substituent on an aryl or heteroaryl nucleus. Similarly, a reactive functional group is located at any position of an alkyl or heteroalkyl chain. In various embodiments, when the reactive group is attached to an alkyl (or heteroalkyl), or substituted alkyl (or heteroalkyl) chain, the reactive group is preferably located at a terminal position of the chain.

Reactive groups and classes of reactions useful in practicing the present invention are generally those that are well known in the art of bioconjugate chemistry. Currently favored classes of reactions available with reactive precursors of the oligomers of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS;

Advances in Chemistry Series, Vol. 198, American Chemical Society, Washington, D.C., 1982.

By way of example, reactive functional groups of use in the present invention include, but are not limited to olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Useful reactive functional group conversions include, for example:

(a) carboxyl groups which are readily converted to various derivatives including, but not limited to, active esters (e.g., N-hydroxysuccinimide esters, N-hydroxybenztriazole esters, thioesters, p-nitrophenyl esters), acid halides, acyl imidazoles, alkyl, alkenyl, alkynyl and aromatic esters;

(b) hydroxyl groups, which can be converted to esters, ethers, halides, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

and (k) phosphoramidites and other standard functional groups useful in nucleic acid synthesis.

The reactive functional groups can be chosen such that they do not participate in, or interfere with, the reactions necessary to assemble the oligomer of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

In some embodiments, a complex has the formula $Ir_4(CO)_{12-x}(L)_x$, where L=tert-butylcalix[4]arene$(OPr)_3$ $(OCH_2PPh_2)$ and x=2, 3, 4 or 5. Thus, the present invention provides phosphine-containing calixarene ligands, e.g., monodentate tert-butyl-Calix$(OPr)_3$(O—$CH_2$—$PPh_2$) and bidentate tert-butyl-Calix$(OMe)_2$(O—$CH_2$—$PPh_2)_2$ calixarene ligands.

One or more calixarene-related compound can be coordinated to one or more metal colloids. Particularly useful metal colloids comprise a plurality of metal atoms selected from Ir, Pt and Pd. An iridium-containing colloid composed of one or more noble metals and/or in conjunction with one or more non-noble metals can be used. In exemplary embodiments, a metal colloid comprises a plurality of iridium atoms, for example in the form of $Ir_x$, wherein x is selected from 2, 3, 4, 5, 6, 7, 8, 9, 10, 11, 12, 13, 14, 15, 16, 17 and 18. The metal colloid can be further substituted with an organic ligand, for example, with —CO.

In some embodiments, a plurality of the calixarene-related compound is coordinated to the metal colloid. In some embodiments, 2, 3, 4 or 5 of the calixarene-related compound are coordinated to the metal colloid. In some embodiments, a plurality of the metal colloid is coordinated to one or a plurality of the calixarene-related compound.

The complexes described herein can be subjected to further conditions to provide for additional compounds. For example, a metal colloid can be formed by a process comprising performing a reaction on a complexed described herein, wherein the reaction is selected from pyrolysis, thermal decomposition, oxidative decomposition and a combination thereof. Such metal colloids can have properties that make them suitable for the various reactions described herein, in particular catalysis.

Immobilization on a Substrate

The invention provides, as described herein, calixarene-related compounds, metal colloids and complexes that can be immobilized on a substrate. The calixarene-related compound can be bound to the substrate through a linker or directly, i.e., without the need for derivatization of the calixarene compound with a flexible tether. The iridium-containing metal colloid can be bound first to a substrate and subsequently complexed to a calixarene or it can be bound to a calixarene-related compound and subsequently bound to a substrate either through the calixarene-related moiety or through the metal colloid. Alternatively, the iridium-containing metal colloid can be contacted with a substrate to which a calixarene-related moiety is bound, thereby forming the immobilized complex. Methods of tethering calixarenes to surfaces are generally known in the art. See, for example, US Publication 2005/0255332 A1 and U.S. Pat. No. 6,380,266 B1.

Exemplary substrate components include, but are not limited to metals, metallic or non-metallic oxides, glasses and polymers. A non-limiting list of useful substrates includes, silicon, tungsten, niobium, titanium, zirconium, manganese, vanadium, chromium, tantalum, aluminum, phosphorus, boron, rhodium, molybdenum, germanium, copper, platinum or iron. A preferred substrate is silica, most preferably silica possessing free hydroxyl groups. However, other inorganic oxide substrates may be used, preferably oxides of titanium, zirconium, germanium, tungsten, niobium, manganese, vanadium, chromium, tantalum, aluminum, phosphorus, boron rhodium, molybdenum, copper, platinum or iron, or another element that forms a stable aryloxide with the substrate. The substrate may be in any convenient physical form, such as gels, the interior or exterior pores of particles of various types, or planar surfaces such as wafers, chips, plates and the like, and surfaces or devices whose surfaces may be overlaid with a silica or other film. For silica substrates at least, due in part to the rigidity of the linkage between the calixarene or related compound and the substrate, this new method results in the highest reported site densities on a per gram of material basis for anchored calixarenes and/or related compounds. Metal oxides and zeolites (intact and delaminated) are exemplary substrates of use in conjunction with the compounds of the invention.

In an exemplary embodiment, the substrate is an inorganic oxide. Inorganic oxides of use in the present invention include, for example, $Cs_2O$, $Mg(OH)_2$, $TiO_2$, $ZrO_2$, $CeO_2$, $Y_2O_3$, $Cr_2O_3$, $Fe_2O_3$, NiO, ZnO, $Al_2O_3$, $SiO_2$ (glass), quartz, $Ir_2O_3$, $SnO_2$, $PbO_2$ and the like. The inorganic oxides can be utilized in a variety of physical forms such as films, supported powders, glasses, crystals and the like. A substrate can consist of a single inorganic oxide or a composite of more than one inorganic oxide. For example, a composite of inorganic oxides can have a layered structure (i.e., a second oxide deposited on a first oxide) or two or more oxides can be arranged in a contiguous non-layered structure. In addition, one or more oxides can be admixed as particles of various sizes and deposited on a support such as a glass or metal sheet. Further, a layer of one or more inorganic oxides can be intercalated between two other substrate layers (e.g., metal-oxide-metal, metal-oxide-crystal).

In these embodiments, an exemplary immobilization process includes contacting the calixarene-related compound with a substrate that has been surface-modified by reaction with one or more polyhalides and/or polyalkoxides of an element capable of forming a stable aryloxide species with the substrate, or reacting the substrate with a calixarene or calixarene-related compound that has been previously modified or derivatized by reaction with said one or more polyhalides and/or polyalkoxides. In an alternate embodiment, the immobilization process includes reacting a polyhalide or polyalkoxide of one or more elements selected from silicon, tungsten, niobium, titanium, zirconium, manganese, vanadium, chromium, tantalum, aluminum, phosphorus, boron, rhodium, molybdenum, germanium, copper, platinum or iron, or another element that forms a stable aryloxide with the substrate, forming a modified substrate; and contacting the modified substrate with a calixarene-related compound so as to immobilize the calixarene-related compound to the substrate through at least one phenolic oxygen linkage.

Inorganic crystals and inorganic glasses appropriate for substrate materials include, for example, LiF, NaF, NaCl, KBr, KI, $CaF_2$, $MgF_2$, $HgF_2$, BN, $AsS_3$, ZnS, $Si_3N_4$ and the like. The crystals and glasses can be prepared by art standard techniques. See, for example, Goodman, C. H. L., Crystal Growth Theory and Techniques, Plenum Press, New York 1974. Alternatively, the crystals can be purchased commercially (e.g., Fischer Scientific). The crystals can be the sole component of the substrate or they can be coated with one or more additional substrate components. Thus, it is within the scope of the present invention to utilize crystals coated with, for example one or more metal films or a metal film and an organic polymer. Additionally, a crystal can constitute a portion of a substrate which contacts another portion of the substrate made of a different material, or a different physical form (e.g., a glass) of the same material. Other useful substrate configurations utilizing inorganic crystals and/or glasses will be apparent to those of salt in the art.

Metals are also of use as substrates in the present invention. Exemplary metals of use in the present invention as substrates include, but are not limited to, gold, silver, platinum, palladium, nickel and copper. In one embodiment, more than one metal is used. The more than one metal can be present as an alloy or they can be formed into a layered "sandwich" structure, or they can be laterally adjacent to one another.

Organic polymers are a useful class of substrate materials. Organic polymers useful as substrates in the present invention include polymers which are permeable to gases, liquids and molecules in solution. Other useful polymers are those which are impermeable to one or more of these same classes of compounds.

Organic polymers that form useful substrates include, for example, polyalkenes (e.g., polyethylene, polyisobutene, polybutadiene), polyacrylics (e.g., polyacrylate, polymethyl methacrylate, polycyanoacrylate), polyvinyls (e.g., polyvinyl alcohol, polyvinyl acetate, polyvinyl butyral, polyvinyl chloride), polystyrenes, polycarbonates, polyesters, polyurethanes, polyamides, polyimides, polysulfone, polysiloxanes, polyheterocycles, cellulose derivative (e.g., methyl cellulose, cellulose acetate, nitrocellulose), polysilanes, fluorinated polymers, epoxies, polyetters and phenolic resins. See, Cognard, J. ALIGNMENT OF NEMATIC LIQUID CRYSTALS AND THEIR MIXTURES, in *Mol. Cryst. Liq. Cryst.* 1:1-74 (1982). Presently preferred organic polymers include polydimethylsiloxane, polyethylene, polyacrylonitrile, cellulosic materials, polycarbonates and polyvinyl pyridinium.

The surface of a substrate of use in practicing the present invention can be smooth, rough and/or patterned. The surface can be engineered by the use of mechanical and/or chemical techniques. For example, the surface can be roughened or patterned by rubbing, etching, grooving, stretching, and the oblique deposition of metal films. The substrate can be patterned using techniques such as photolithography (Kleinfield et al., *J. Neurosci.* 8: 4098-120 (1998)), photoetching, chemical etching and microcontact printing (Kumar et al., *Langmuir* 10: 1498-511 (1994)). Other techniques for forming patterns on a substrate will be readily apparent to those of skill in the art.

The size and complexity of the pattern on the substrate is controlled by the resolution of the technique utilized and the purpose for which the pattern is intended. For example, using microcontact printing, features as small as 200 nm have been layered onto a substrate. See, Xia et al., *J. Am. Chem. Soc.* 117: 3274-75 (1995). Similarly, using photolithography, patterns with features as small as 1 μm have been produced. See, Hickman et al., *J. Vac. Sci. Technol.* 12: 607-16 (1994). Patterns that are useful in the present invention include those which comprise features such as wells, enclosures, partitions, recesses, inlets, outlets, channels, troughs, diffraction gratings and the like.

Using recognized techniques, substrates with patterns having regions of different chemical characteristics can be produced. Thus, for example, an array of adjacent, isolated features is created by varying the hydrophobicity/hydrophilicity, charge or other chemical characteristic of a pattern constituent. For example, hydrophilic compounds can be confined to individual hydrophilic features by patterning "walls" between the adjacent features using hydrophobic materials. Similarly, positively or negatively charged compounds can be confined to features having "walls" made of compounds with charges similar to those of the confined compounds. Similar substrate configurations are also accessible through microprinting a layer with the desired characteristics directly onto the substrate. See, Mrkish, et al., *Ann. Rev. Biophys. Biomol. Struct.* 25:55-78 (1996).

In various exemplary embodiments, the substrate is a zeolite or zeolite-like material. In one embodiment, the complexes of the invention are attached to a substrate by the surface functionalization of ITQ-2-type layered and zeolitic materials. An exemplary attachment is effected via ammoniation of the substrate. The invention provides such functionalized materials covalently-bound to calixarenes. In an exemplary embodiment, the functionalized surfaces will are used to nucleate and grow metal colloids on the surface of the material.

Calixarene-related compounds can be immobilized onto silica or other substrates as mentioned above without the need for synthetic derivatization with flexible linker groups that contain carbon, sulfur, etc. The resulting immobilized calixarenes and related compounds possess lipophilic cavities that can be accessed with gas physisorption experiments at cryogenic temperatures, as well as with neutral organic molecules at room temperature. Phenol and nitrobenzene adsorb reversibly from aqueous solution within this class of materials.

The resulting immobilized calixarenes and related compounds can entrap moieties including small molecules, proteins and ions (both cations and anions), and thus may be used for a number of functions, including in membranes, as selective catalysts, in specific adsorption or trapping of a species in a gas stream, in high-pressure liquid chromatography or gas chromatographic columns, and in chemical sensing. See, Katz et al., Langmuir 22: 4004-4014 (2006).

In various embodiments, the invention provides a method for the immobilization of a calixarene or a calixarene-related compound to a substrate by one of two means: (a) by contacting the calixarene-related compound with a substrate that has been surface modified by reaction with a polyhalide or polyalkoxide as described below, or (b) by reaction of a substrate with a calixarene-related compound that has been previously modified or derivatized by reaction with such a polyhalide or polyalkoxide.

One exemplary embodiment of this invention is the use of a silicon halide or alkoxide to modify a silica substrate and immobilize the calixarene-related compound/moiety to the substrate via silica-oxygen bonds. However, as previously discussed, the substrate and/or the modifying agent may be an oxide, polyhalide or polyalkoxide of another element. The modifying agents may contain the same element as the primary element on the substrate (e.g. aluminum alkoxides used to modify an aluminum oxide substrate) or they may contain different elements (e.g. silicon tetrahalide used to modify an aluminum oxide substrate). When alkoxides are used in this invention, the substrate-modifying element of the alkoxide (silicon, another non-metal, or a metal) becomes bonded directly to phenolic oxygen atoms of the calixarene, and an alcohol corresponding to the alkoxide is split off. Preferred alkoxides used as substrate modifiers in this invention include methoxides, ethoxides and other alkoxides having up to four carbon atoms per alkoxide group.

In another preferred embodiment, a halide or alkoxide of a transition metal or a polyvalent non-metal other than silicon is used to immobilize a calixarene or a calixarene-related compound to a substrate. The metal or non-metal may be any that forms a stable aryloxide with the substrate, including but not limited to silicon, tungsten, niobium, titanium, zirconium, iron, manganese, vanadium, chromium, tantalum, aluminum, phosphorus, boron, rhodium, molybdenum, germanium, copper, platinum or iron.

Synthesis

The calixarene-related compounds, metal colloids and complexes thereof described herein can be synthesized by methods within the abilities of those of skill in the art. Exemplary syntheses are set forth herein, however, it will be apparent to those of skill that additional practical synthetic pathways exist and can be devised. Accordingly, the present invention is not limited to the use of a calixarene-related compound synthesized by any particular method.

Exemplary routes to calixarene-related compounds of the invention are set forth in Scheme 1 below.

The present invention provides compounds in which a calixarene-related compound is complexed to a metal colloid. It is well within the ability of those of skill in the art to choose a particular combination of coordinating atom on a linker and metal atom in a colloid to provide a coordinating atom that binds to the colloid.

The invention is exemplified by reference to colloids of Ir (e.g. $Ir_4$), Pt, Pd, Ni, Mo, W, and Co; bimetallic clusters and nickel/cobalt molybdenum/tungsten sulfide nanoparticulate catalysts. In various embodiments, the invention provides a complex formed based on $Ir_4(CO)_{12}$.

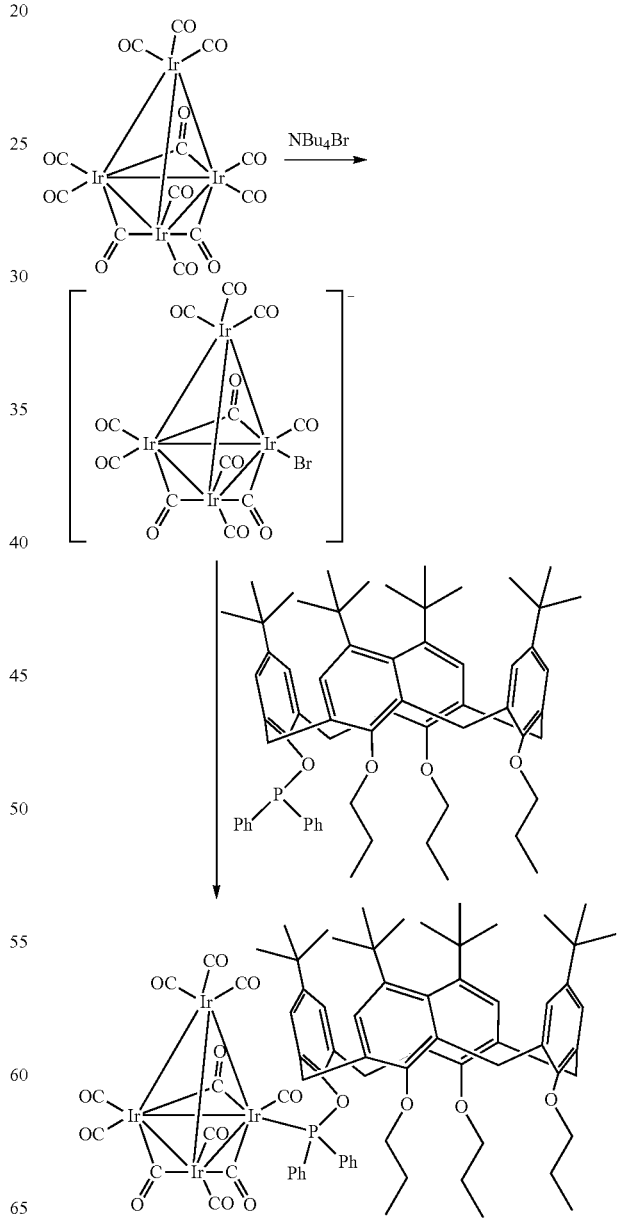

Scheme 1

Scheme 1 is directed to a complex in which the calixarene-related compound is monodentate. As will be appreciated, linkers having higher denticity are also of use. When a bidentate calixarene-related molecule is utilized as a ligand, the metal colloids of this compound and others can be prepared in one of several geometries. For example, diradial bridging, axial-radial bridging, diaxial bridging, axial-radial bridging:

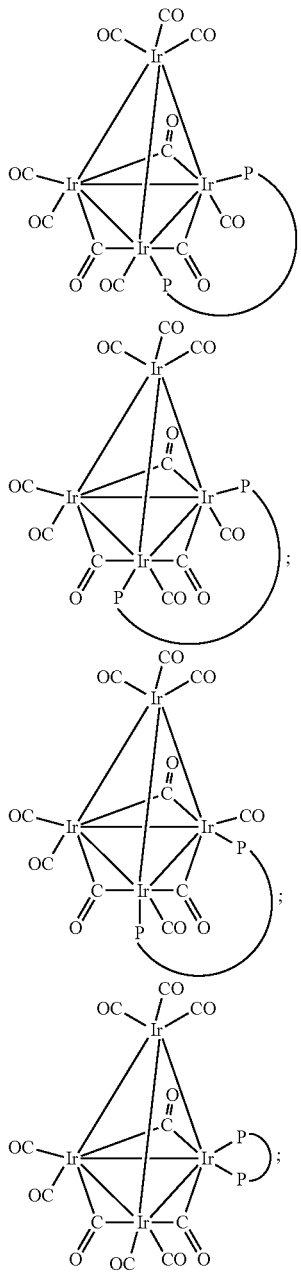

As will be appreciated by those of skill in the art, the invention also provides colloids of other systems including, but not limited to, Pt, Pd, Ni, Mo, W, Co, bimetallic clusters, and nickel/cobalt molybdenum/tungsten sulfide nanoparticulate catalysts.

In one aspect, the invention provides methods of synthesizing a calixarene-bound metal colloid. In one embodiment, a method of synthesizing a calixarene-bound metal colloid comprises contacting a calixarene-related compound with a colloidal metal bromide under conditions appropriate to cause bromide anion displacement from the colloidal metal bromide.

In some embodiments, the method further comprises, prior to the contacting step, activating a colloidal metal with a brominating agent under conditions sufficient to form the colloidal metal bromide. In some embodiments, the colloidal metal comprises a plurality of iridium atoms and the brominating agent brominates one or more of the plurality of iridium atoms. In some embodiment, the colloidal metal bromide comprises iridium, optionally wherein the iridium is bound to a single bromide ligand, and optionally wherein the iridium is in the form of $Ir_4$.

In some embodiments, the calixarene-related compound is selected from a calixarene phosphine, a calixarene phosphinite, a calixarene phosphonite, a calixarene phosphite and a calixarene phosphoramidite.

In some embodiments, the calixarene-related compound is a calixarene carbene.

In some embodiments, the calixarene-related compound is selected from a calixarene pyridine, a calixarene bipyridine, a calixarene terpyridine, a calixarene pyrazole, a calixarene phenanthroline, a calixarene isonitrile, a calixarene amide, a calixarene amine, a calixarene amine oxide, a calixarene nitroso, a calixarene nitro and a calixarene carbamate.

In some embodiments, the calixarene-related compound is selected from a calixarene carboxylate, a calixarene alkoxide, a calixarene peroxo, a calixarene phenoxide, a calixarene ester, a calixarene ether, a calixarene acetylacetonate and a calixarene carbonate.

In some embodiments, the calixarene-related compound is the calixarene-related compound of a complex described herein or a calixarene-related compound described herein.

Uses

In one aspect, the invention provides catalytic processes that utilize the metal colloids or metal complexes disclosed herein. Calixarene-related metal colloids and complexes disclosed herein can be used to catalyze processes including those known in the art to be catalyzed by metal-mediated processes, such as olefin rearrangements, hydroformylation of olefins, and cycloaddition of terminal alkanes, as well as other processes such as oxidation processes, hydrogenation processes, and acid-catalyzed reactions. In an exemplary embodiment, the composition of the invention is useful as a hydroprocessing catalyst. Other processes in which the compounds and complexes of the invention find use include propane hydrogenolysis, CO hydrogenation, toluene hydrogenation, methanation, intramolecular hydroamination, asymmetric isomerization of primary allylic alcohols, allylic amination, hydroamination, hydrothiolation, C—H bond arylation of heteroarenes using iodoarenes, [2+2+2] cycloadditions, and carbonylation, methane hydroxylation, and naphthenic ring opening (See U.S. Pat. No. 5,763,731). Still further processes include hydrogenation reactions, such as of α,β-unsaturated aldehydes; cyclization reactions, such as of terpenoids (e.g., transformation of citronellal to menthol); ring opening reactions, such as of cycloalkyls (e.g. conversion of methylcyclohexane to dimethylpentane, or naphthenic ring opening); steam catalytic reforming of NO and hydroconversion reactions, such as of cycloalkyls (e.g. cyclohexene). (See Vuori et al., Catal. Left., 2009, 131: 7-15 and U.S. Pat. No. 5,763,731) Generally useful reactions include oxidations and reductions performed on an organic molecule, e.g. alkyl, heteroalkyl, cycloalkyl, heterocycloalkyl, aryl or heteroaryl, any of which is optionally substituted.

Accordingly, in one embodiment, a catalytic process comprises reducing an organic molecule by contacting the organic molecule with (a) a complex or a metal colloid disclosed herein and (b) a reductant. In some embodiments, the organic molecule is an unsaturated molecule. In some embodiments, the organic molecule is a substituted or unsubstituted alkyl (for example, an unsaturated alkyl, such as an unsaturated $C_1$, $C_2$, $C_3$, $C_4$, $C_5$ or $C_6$ alkyl). In some embodiments, the reducing step comprises hydrogenation, for example, using $H_2$ as a reductant.

In one embodiment, a catalytic process comprises oxidizing an organic molecule by contacting the organic molecule with (a) a complex or a metal colloid disclosed herein and (b) an oxidant. In some embodiments, the oxidizing step comprises hydroxylation.

EXAMPLES

Example 1

Experimental

All compounds were handled using Schlenk techniques under dry nitrogen atmosphere. Anhydrous toluene, THF and DMF were purchased from Aldrich; starting p-tert-butylcalix[4]arene and all others reagents were of analytical grade and used as received. Calixarenes 1a, 1b, 4a, 4b, 5a and 7a were synthesized following a literature procedure. Diphenylphosphorylmethylenetosylate has been prepared according to literature procedures. $^1$H, $^{13}$C, and $^{31}$PNMR spectra were recorded in CDCl$_3$ (293K) either on a Bruker AV-300 (300 MHz) instrument or on a AVB-400 (400 MHz) instrument at the UC Berkeley NMR Facility. The $^1$H NMR data are referenced to residual CHCl$_3$ (7.260 ppm) and $^{31}$PNMR data are referenced relative to trimethyl phosphate. Analytical thin-layer chromatography was performed on precoated silica gel plates (0.25 mm, 60E-254, Selecto), and silica gel (Selecto 60) was used for column chromatography. FAB-MS spectra were recorded with using o-nitrophenyloctyl ether (NPOE) or m-nitrobenzyl alcohol (NBA) as matrix at the UC Berkeley Mass Spectrometry Facility. All melting points are uncorrected.

General Procedure for the Synthesis of Calixarene-Phosphinoxides 2a,b, 5b and 8a

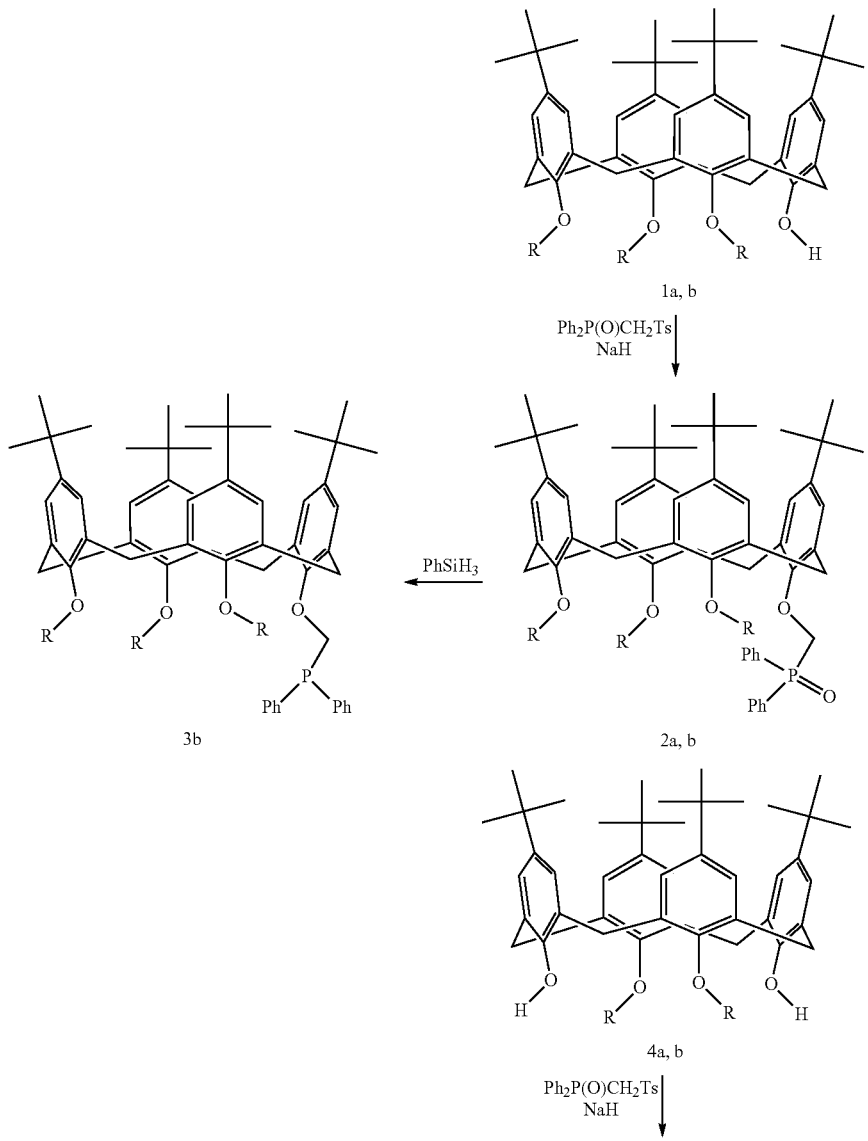

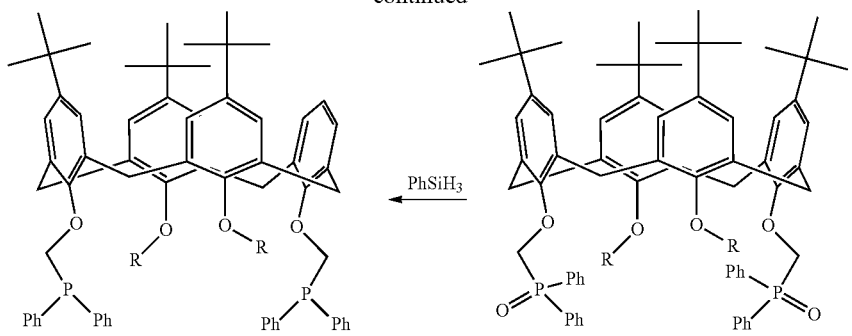
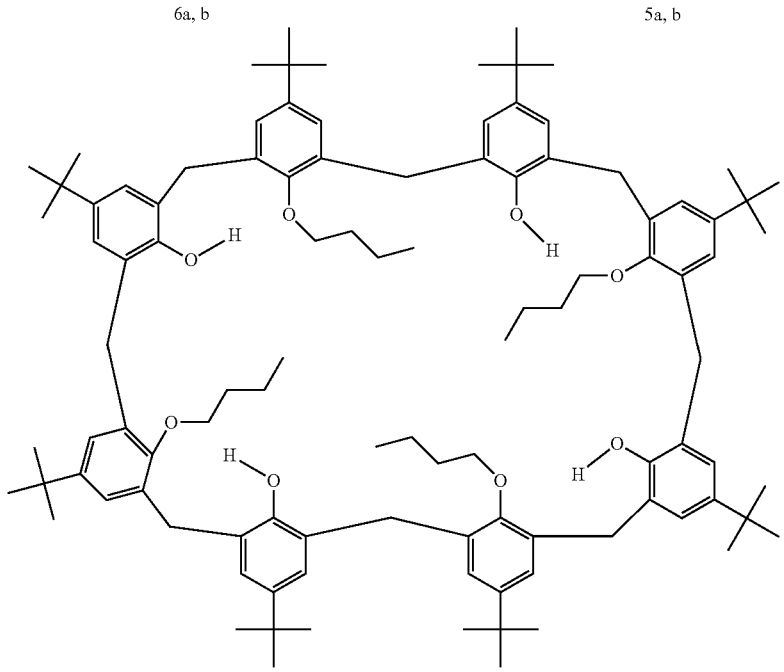
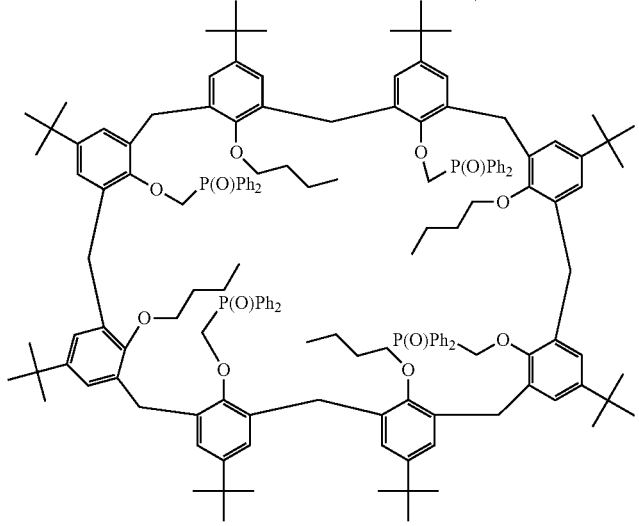
R = Me (a), n-Pr (b)

The mixture of calixarene 1a,b, 4a,b, 7a (0.35 mmol) and sodium hydride (0.39 mmol for 1a,b, 0.78 mmol for 4a,b, 1.56 mmol for 7a) in THF/DMF (10/1 v/v) was refluxed for 2 h. To the yellow solution formed, Ph$_2$P(O)CH$_2$OTs (0.39 mmol for 1a,b, 0.78 mmol for 4a,b, 1.56 mmol for 7a) was added. The reaction mixture was refluxed for 48 h. Excess of sodium hydride was quenched with ~1.0 ml of methanol and solvents were evaporated. The residue was dissolved in chloroform and washed twice with water. The organic phase was evaporated to dryness and subjected to purification.

5,11,17,23-Tetra-tert-butyl-25-diphenylphosphinoyl-methyleneoxy-26,27,28-trimethoxy-calix[4]arene (Mixture of Conformers) (2a)

Column chromatography with CH$_2$Cl$_2$/ethylacetate (1:0.2) afforded 62% yield of white powder, Rf 0.6: mp 108-115° C.; $^1$H NMR (400 MHz, CDCl$_3$) δ 7.89 (br m, 4H, C$_6$H$_5$PO), 7.45-7.49 (br m, 6H, C$_6$H$_5$PO), 7.01-7.14 (br m, 5H, ArH-m), 6.37-6.49 (br m, 3H, ArH-m), 4.62 (s, 2H, CH$_2$PO), 4.32 (br m, 2H, ArCH$_2$Ar), 3.92 (br m, 2H, ArCH$_2$Ar), 3.61-3.74 (br m, 2H+3H, ArCH$_2$Ar+OCH$_3$), 3.21 (m, 2H, ArCH$_2$Ar), 3.09 (br m, 3H, OCH$_3$), 2.94 (s, 3H, OCH$_3$), 1.33 (m, 21H, C(CH$_3$)$_3$), 0.70-1.10 (br m, 15H, C(CH$_3$)$_3$); $^{31}$P NMR δ 26.15, 25.44, 24.60, 24.41; MS FAB m/z 689 [M-CH$_2$PO(C$_6$H$_5$)$_2$+H$^+$], 703 [M-PO(C$_6$H$_5$)$_2$+H$^+$], 905 [M+H$^+$]

5,11,17,23-Tetra-tert-butyl-25-diphenylphosphinoyl-methyleneoxy-26,27,28-tripropoxy-calix[4]arene (Cone) (2b)

Column chromatography with CH$_2$Cl$_2$/ethylacetate (1:0.1) afforded 83% yield of white powder, Rf 0.7: mp 118-121° C.; $^1$HNMR (400 MHz, CDCl$_3$) δ 7.79-7.83 (m, 4H, C$_6$H$_5$PO), 7.45-7.51 (m, 6H, C$_6$H$_5$PO), 6.98 (s, 2H, ArH-m), 6.95 (s, 2H, ArH-m), 6.52 (s, 2H, ArH-m), 6.38 (s, 2H, ArH-m), 4.75 (s, 2H, CH$_2$PO), 4.38 (d, $^2$J=12.4 Hz, 2H, ArCH$_2$Ar), 4.36 (d, $^2$J=12.8 Hz, 2H, ArCH$_2$Ar), 3.80 (m, 2H, OCH$_2$), 3.71 (m, 2H, OCH$_2$), 3.63 (t, $^3$J=7.2 Hz, 2H, OCH$_2$), 3.07 (d, $^2$J=12.8 Hz, 2H, ArCH$_2$Ar), 3.02 (d, 2J=12.4 Hz, 2H, ArCH$_2$Ar), 1.93 (m, 6H, OCH$_2$CH$_2$), 1.24 (s, 18H, C(CH$_3$)$_3$), 1.00 (t, 3J=7.2 Hz, 3H, CH$_3$CH$_2$), 0.90 (s, 9H, C(CH$_3$)$_3$), 0.82 (m, 18H, C(CH$_3$)$_3$+CH$_3$CH$_2$); $^{13}$C NMR δ 154.41, 152.92, 144.69, 144.29, 143.83, 135.17, 134.82, 132.41 132.09, 131.84, 131.67, 131.25, 131.16, 128.57, 128.46, 125.30, 125.26, 124.82, 124.33, 33.92, 33.60, 31.63, 31.22, 31.17, 31.04, 23.47, 23.04, 10.56, 10.22; $^{31}$P NMR δ 24.44; MS FAB m/z 989 [M+H$^+$].

5,11,17,23-Tetra-tert-butyl-25,26-bis(diphenylphos-phinoylmethyleneoxy)-27,28-dipropoxy-calix[4]arene (Cone) (5b)

Column chromatography with CH$_2$Cl$_2$/ethylacetate (1:0.5) afforded 53% yield of white powder, Rf 0.4: mp 134-138° C.; $^1$HNMR (400 MHz, CDCl$_3$) δ 7.74-7.81 (m, 8H, C$_6$H$_5$PO), 7.40-7.46 (m, 6H, C$_6$H$_5$PO), 7.00 (s, 4H, ArH-m), 6.32 (s, 4H, ArH-m), 4.63, 4.64 (d, 4H, $^2$J$_{PH}$=2.4 Hz, CH$_2$P), 4.30 (d, $^2$J=12.8 Hz, 4H, ArCH$_2$Ar), 3.64 (m, 4H, OCH$_2$), 2.98 (d, $^2$J=12.8 Hz, 4H, ArCH$_2$Ar), 1.75 (m, 4H, CH$_2$CH$_3$), 1.29 (s, 18H, C(CH$_3$)$_3$), 0.79 (s, 18H, C(CH$_3$)$_3$), 0.72 (t, $^3$J=7.2 Hz, 6H, CH$_2$CH$_3$); $^{31}$P NMR δ 24.76.

O$^1$,O$^3$,O$^5$,O$^7$-Tetrakis(diphenylphosphorylmethyloxy)-tetrabutyloxy-p-tert-butyl-calix[8]arene (8a)

Flash chromatography with CH$_2$Cl$_2$/methanol (1:0.05 v/v), white powder, Rf 0.2; $^1$H NMR (CDCl$_3$) δ 8.06 (m, 16H, C$_6$H$_5$PO), 7.51-7.59 (m, 24H, C$_6$H$_5$PO), 7.07 (s, 8H ArH), 6.53 (s, 8H, ArH), 4.76 (d, 8H, $^3$J$_{PH}$=7.2 Hz, CH$_2$PO), 4.10 (br s, 8H), 3.40 (br s, 8H), 2.65 (br s, 8H), 1.42 (s, 9H), 1.27 (br s, 36H), 0.85 (br m, 12H), 0.76 (s, 36H), 0.35 (br s, 12H); $^{31}$PNMR (CDCl$_3$) δ 28.41, 26.33, 25.71.

General Procedure for the Synthesis of Calixarene-Phosphines 3b and 6a,b

A solution of calixarenes 2b, 5a,b (7.0 mmol) and PhSiH$_3$ (30 eq. excess for each POPh$_2$) in 15 ml of toluene was heated at 100° C. for 48 h. The progress of reaction was monitored with $^{31}$PNMR. The reaction mixture was evaporated to dryness and vacuumated for 4 h (0.05 mm) The oily residue was subjected to purification.

5,11,17,23-Tetra-tert-butyl-25-diphenylphosphinom-ethyleneoxy-26,27,28-tripropoxy-calix[4]arene (Cone) (3b)

Flash chromatography with CH$_2$Cl$_2$, afforded 54% yield of white powder, Rf 0.9: mp 113-117° C.; $^1$H NMR δ 7.40 (m, 4H, C$_6$H$_5$P), 7.30 (m, 6H, C$_6$H$_5$P), 6.88 (s, 2H, ArH), 6.86 (s, 2H, ArH), 6.64 (s, 2H, ArH), 6.58 (s, 2H, ArH), 4.83 (d, 2H, $^2$JPH 2.8 Hz, CH$_2$P), 4.39 (d, 4H, $^2$J=12.4 Hz, ArCH$_2$Ar), 3.70-3.83 (m, 6H, OCH$_2$), 3.09 (d, 2H, $^2$J=12.4 Hz, ArCH$_2$Ar), 3.06 (d, 2H, $^2$J=12.4 Hz, ArCH$_2$Ar), 1.95-2.03 (m, 6H, CH$_2$CH$_3$), 1.16 (s, 18H, C(CH$_3$)$_3$), 0.92 (s, 18H, C(CH$_3$)$_3$), 0.82 (m, 9H, CH$_2$CH$_3$); $^{31}$P NMR δ −21.82; FAB MS m/z 775 [M-CH$_2$P(C$_6$H$_5$)$_2$+H$^+$], 787 [M-P(C$_6$H$_5$)$_2$+H$^+$], 973 [M+H$^+$].

5,11,17,23-Tetra-tert-butyl-25,26-bis 1 diphe-nylphosphinomethyleneoxyl-27,28-dimethoxy-calix[4]arene (Mixture of Conformers) (6a)

Crystallization from ethanol/DCM (20/1) gave the white solid with 52% yield; mp 123-131° C.; $^1$H NMR δ 7.33-7.55 (m, 40H, C$_6$H$_5$P), 7.09 (s, 6H, ArH), 7.00 (s, 2H, ArH), 6.91 (s, 2H, ArH), 6.41 (s, 2H, ArH), 6.38 (s, 4H, ArH), 4.56 (m, 8H, OCH$_2$+ArCH$_2$Ar), 4.25 (d, 4H, $^2$J=13.6 Hz, ArCH$_2$Ar), 3.60-4.00 (m, 6H, ArCH$_2$Ar), 3.52 (s, 6H, OCH$_3$), 3.31 (s, 3H, OCH$_3$), 3.09 (d, 4H, $^2$J=13.6 Hz, ArCH$_2$Ar), 2.98 (m, 2H, ArCH$_2$Ar), 2.69 (s, 3H, OCH$_3$), 1.33, 1.02, 0.78 (three s, 72H, C(CH$_3$)$_3$); $^{31}$P NMR δ −21.12, −21.99.

5,11,17,23-Tetra-tert-butyl-25,26-bis(diphenylphos-phinomethyleneoxy)-27,28-dipropoxy-calix[4]arene (Cone) (6b)

Flash chromatography with CH$_2$Cl$_2$, afforded 41% yield of white powder, Rf 0.9; mp 128-132° C.; $^1$HNMR δ 7.47 (m, 8H, C$_6$H$_5$P), 7.32 (m, 12H, C$_6$H$_5$P), 7.00 (s, 4H, ArH), 6.49 (s, 4H, ArH), 4.70 (d, 4H, $^2J_{PH}$=2.4 Hz, CH$_2$P), 4.38 (d, 4H, $^2$J=12.4 Hz, ArCH$_2$Ar), 3.73 (m, 4H, OCH$_2$), 3.09 (d, 4H, $^2$J=12.4 Hz, ArCH$_2$Ar), 1.94 (m, 4H, CH$_2$CH$_3$), 1.27 (s, 18H, C(CH$_3$)$_3$), 0.89 (s, 18H, C(CH$_3$)$_3$), 0.75 (t, 6H, $^3$J=7.2 Hz, CH$_2$CH$_3$); $^{13}$CNMR δ 154.56, 153.59, 153.52, 144.43, 144.34, 136.95, 136.82, 135.11, 134.05, 133.18, 133.06, 132.87, 132.11, 128.66, 128.43, 128.36, 128.09, 125.25, 124.58, 33.95, 33.63, 31.65, 31.53, 32.20, 23.27, 10.06; $^{31}$PNMR δ −22.28.

REFERENCES

Iwamoto, K.; Fujimoto, K.; Matsuda, T.; Shinkai, S., Tetrahedron Letters, 1990, 31, 7169-7172.

Dijkstra, P. J.; Brunink, J. A. J.; Bugge, K. E.; Reinhoudt, D. N.; Harkema, S.; Ungaro, R.; Ugozzoli, F.; Ghidini, E. J.A.C.S., 1989, 111, 7567-7575.

Gutsche, C. D.; Bhavan, B.; Levine, J. A.; No, K. H.; Bauer, L. J., Tetrahedron, 1983, 38, 409-413.

Dieleman, C. B.; Matt, D.; Jones, P. G. J., Organometallic Chem., 1997, 545-546, 461-473.

Marmor, R. S.; Seyferth, D. J., Org. Chem., 1969, 34, 748-749.

Wegener, W. Zeitschrift fuer Chemie, 1971, 11, 262.

Neri, P., Battocolo, E., Cunsolo, F., Geraci, C., Piattelli, M., J. Org. Chem., 1994, 59, 3880-3889.

Dieleman, C.; Loeber, C.; Matt, D.; De Cian, A.; Fischer, J., Journal of the Chemical Society, Dalton Transactions: Inorganic Chemistry, 1995, 18, 3097-3100.

Example 2

Synthesis of Calixarene-Bound Iridium Clusters

Synthesis of I

Scheme 2

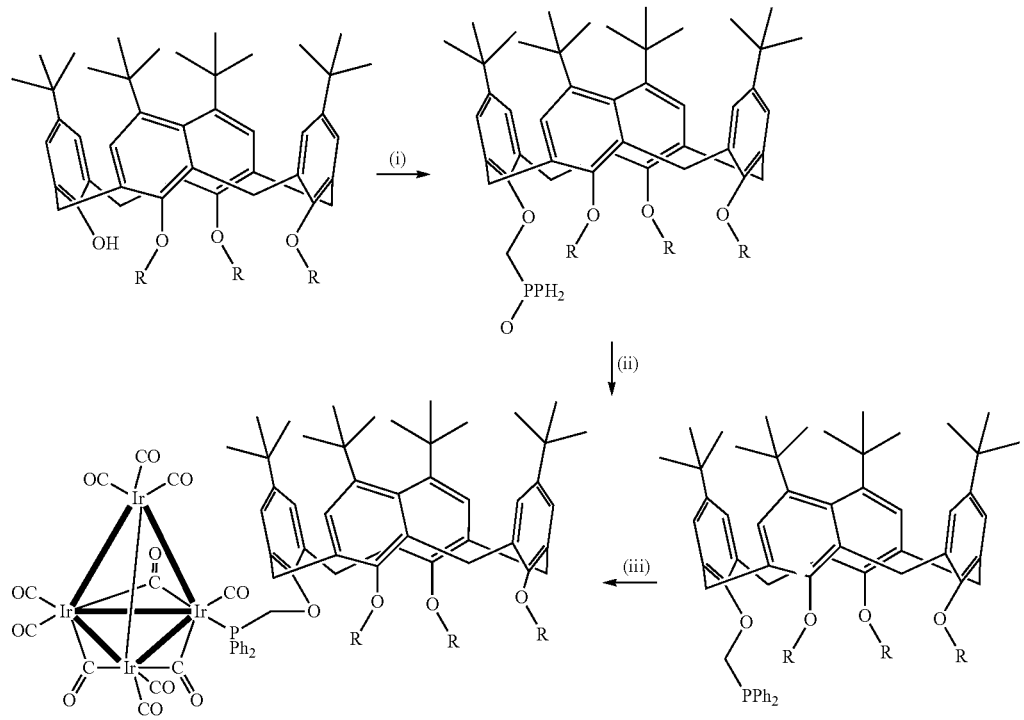

(i) Ph$_2$(O)CH$_2$OTs, NaH, THF/DMF, (ii) PhSiH$_3$, toluene, (iii) [Ir$_4$(CO)$_{11}$Br]Bu$_4$N, CH$_2$Cl$_2$ (R = C$_3$H$_7$-n)

Scheme 2 outlines the synthetic approach to tert-butyl-calix[4]arene(OPr)$_3$(OCH$_2$P(O)Ph$_2$) via known tert-butyl-calix[4]arene(OPr)$_3$(OH) and subsequent phosphine oxide reduction to yield new ligand tert-butyl-calix[4]arene(OPr)$_3$ (OCH$_2$PPh$_2$) in 54% yield. Selective substitution of known Ir$_4$(CO)$_{11}$Br using monophosphine 2 synthesizes 1 as a yellow crystalline solid in high yield via Br$^-$ anion displacement. The ESI mass spectrum of 1 contains the sodium adduct [1Na]$^+$ at m/z=2073.5 as the major peak along with the molecular cation of 1, [1]$^+$, at m/z=2050.5. Experimentally observed isotopic distribution for [1]$^+$ is in good agreement with simulation, and suggests formation of the calixarene arene cation radical species under ESI conditions. The presence of [1]$^+$ in the ESI spectrum is somewhat unusual since protonated or cationic species are typically observed during electrospray ionization. $^{31}$P NMR spectroscopy of 1 in CDCl$_3$ at room temperature exhibits a single resonance at −10.2 ppm, shifted significantly downfield relative to the resonance for free ligand 3 at −21.8 ppm. A sharp singlet remains as the only resonance in the $^{31}$P NMR spectrum of 1 even at low temperature; and, in contrast to systems that consist of a mixture of interconverting axial and equatorial isomers, proves the presence of a single isomer of 1 in solution.

In a typical reaction tert-butyl-calix[4]arene(OPr)$_3$(OCH$_2$PPh$_2$) 0.146 g (0.15 mmol) and [Ir$_4$(CO)$_{11}$Br][NBu$_4$] 0.21 g (0.15 mmol) was stirred in CH$_2$Cl$_2$ (25 mL) at room temperature for overnight. The product was isolated by evaporating the solvent followed by extraction with hexane, and purified by column chromatography to obtain 1 as a yellow crystalline solid. Single crystals were grown from slow evaporation of 1 from CHCl$_3$.

$^1$H NMR δ 7.67 (m, 4H, C$_6$H$_5$P), 7.45 (m, 6H, C$_6$H$_5$P), 7.06 (s, 2H, ArH), 6.96 (s, 2H, ArH), 6.40 (s, 2H, ArH), 6.07 (s, 2H, ArH), 4.54 (d, 2H, $^2$J$_{PH}$ 3.6 Hz, CH$_2$P), 4.30 (d, 2H, $^2$J=12.4 Hz, ArCH$_2$Ar), 3.79 (d, 2H, $^2$J=12.8 OCH$_2$), 3.72 (m, 4H, OCH$_2$) 3.55 (t, 2H, $^3$J=7.2 Hz, ArCH$_2$Ar), 3.05 (d, 2H, $^2$J=12.4 Hz, ArCH$_2$Ar), 2.67 (d, 2H, $^2$J=12.4 Hz, ArCH$_2$Ar), 1.79-1.88 (m, 6H, CH$_2$CH$_3$), 1.31 (s, 18H, C(CH$_3$)$_3$), 1.00 (t 6H $^3$J=7.2 Hz, CH$_2$CH$_3$) 0.92 (t, 3H $^3$J=7.2 Hz, CH$_2$CH$_3$) 0.82 (s, 9H, C(CH$_3$)$_3$), 0.70 (s, 9H, C(CH$_3$)$_3$); $^{31}$P NMR δ −10.2; ESI MS (+) m/z 2050 [M], 2073 [M+Na]; IR (cm$^{-1}$) in CH$_2$Cl$_2$, 2087, 2055, 2027, 1842, 1818.

Tert-butyl-calix[4]arene(OPr)$_2$(OCH$_2$Ph$_2$)$_2$(Ir$_4$(CO)$_{11}$)$_2$

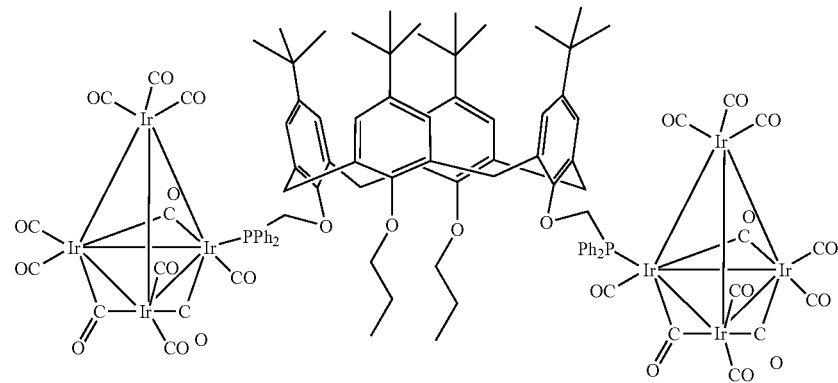

In a typical reaction tert-butyl-calix[4]arene(OPr)$_2$(OCH$_2$PPh$_2$)$_2$ 0.090 g (0.08 mmol) and [Ir$_4$(CO)$_{11}$Br][NBu$_4$] 0.225 g (0.16 mmol) were stirred in CH$_2$Cl$_2$ (25 mL) at room temperature overnight. The product was isolated by evaporating the solvent followed by extraction with hexane, and purified by column chromatography using dichloromethane as solvent. Single crystals were grown by using a layer diffusion method and a CH$_2$Cl$_2$/MeOH solvent system. $^{31}$P NMR δ −10.1; ESI MS (+) m/z 3282 [M], 3418 [M+Cs]. The structure of this cluster derived via single-crystal X-ray diffraction is included in the Figures.

Tert-butyl-calix[4]arene(OMe)$_2$(OCH$_2$PPh$_2$)$_2$(Ir$_4$(CO)$_{11}$)$_2$

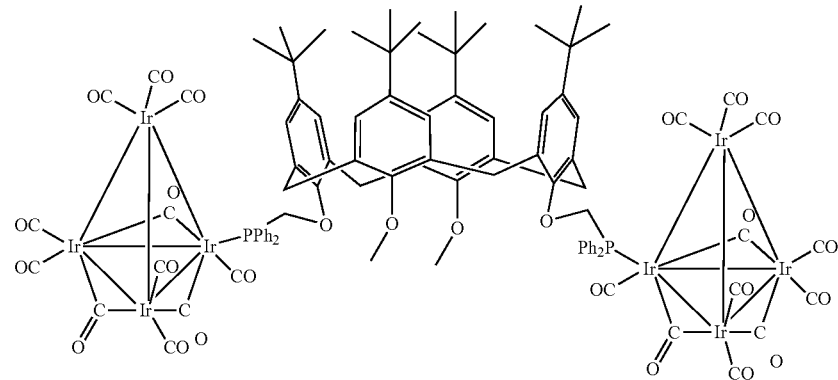

Reagent tert-butyl-calix[4]arene(OMe)$_2$(OCH$_2$PPh$_2$)$_2$ 0.080 g (0.075 mmol) and [Ir$_4$(CO)$_{11}$Br][NBu$_4$] 0.210 g (0.15 mmol) were stirred in CH$_2$Cl$_2$ (20 mL) at room temperature overnight. The product was isolated by evaporating the solvent followed by extraction with hexane, and purified by column chromatography using dichloromethane as solvent. 31P NMR δ −11.2; ESI MS (+) m/z 3359 [M+Cs]. The structure of this cluster derived via single-crystal X-ray diffraction is included in the Figures.

Tert-butyl-calix[4]arene(OPr)$_3$(OCH$_2$PPh$_2$)]$_2$Ir$_4$(CO)$_{10}$

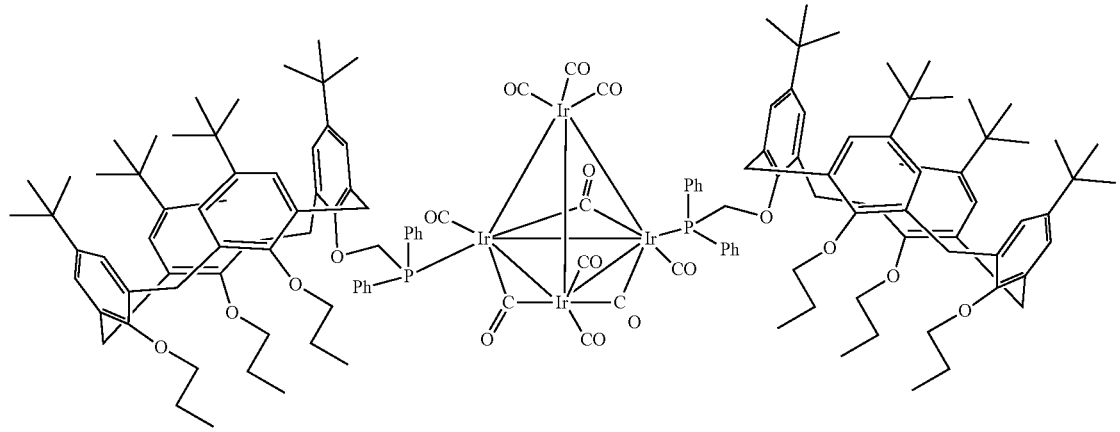

Reagent tert-butyl-calix[4]arene(OPr)$_3$(OCH$_2$PPh$_2$) 0.15 g (0.15 mmol) and [Ir$_4$(CO)$_{11}$Br][NBu$_4$] 0.105 g (0.075 mmol) were stirred in toluene (20 mL) at 80° C. overnight. The product was isolated by evaporating the solvent followed by extraction with hexane, and purified by column chromatography using dichloromethane as solvent. ESI MS (+) m/z 2994 [M−H].

Temperature Programmed Oxidative Decomposition (TPOD) Analysis

The effect of the calixphosphine ligand on bound CO ligand oxidation is ascertained by comparison with Ir$_4$(CO)$_{12}$ using temperature programmed oxidative decomposition (TPOD) followed by thermogravimetric analysis and mass spectroscopy, which is shown in the Figures. Oxidation of CO ligands in Ir$_4$(CO)$_{12}$ mixed with silica occurs in a narrow temperature range starting at 115° C. via mass spectroscopy. Under similar conditions, there is no detectable rate of CO ligand oxidation via mass spectroscopy until a temperature of 135° C. during TPOD in 1 mixed with silica. CO oxidation in 1 mixed with silica occurs almost concomitantly with phenyl loss and partial calixarene combustion over a broad temperature range.

Oxidation of CO in 1 and Ir$_4$CO$_{12}$ was characterized under oxidative conditions using temperature programmed oxidative decomposition (TPOD). In order to avoid sublimation, the compounds were physically mixed with a large excess of dehydroxylated silica (previously pretreated to (i) 600° C. in O2/He/Ar 5/92/3 for 4 h, (ii) followed by cooling to room temperature under inert atmosphere, (iii) heating to 600° C. in H2/He/Ar 15/82/3 for 4 h, (iv) cooling to room temperature under same gas composition as in (iii), and (v) stored in the glove box) to form a solid mixture. The following temperature program was used: isothermal at 40° C. for 60 min followed by constant temperature increase (1° C./min) to 350° C. under a 20% O$_2$/Ar flow of 74 mL/min. The gaseous effluent was analyzed on-stream using mass spectrometry and infrared spectroscopy with an integrated NetschSTA 309 PC Luxx TGA-Netsch 403C AëolosMS-Bruker Tensor 27 (coupled to TGA module and equipped with MCT detector) system. Thus, 6.48 mg of Ir$_4$CO$_{12}$ were mixed with 103.84 mg of dehydroxylated silica. 101.84 mg of this mixture was analyzed (corresponding to 5.98 mg of Ir$_4$CO$_{12}$). A 1.74 mg mass loss was observed via thermogravimetric analysis between 43° C. and 350° C. for the Ir$_4$(CO)$_{12}$ mixed with silica system in the Figures. This compares with a theoretical prediction of 1.82 mg of mass loss for complete decarbonylation in this system. For 1, 7.40 mg of 1 were mixed with 92.08 mg of dehydroxylated silica. 89.91 mg of this mixture was analyzed (corresponding to 6.69 mg of 1). Mass spectroscopy of amu 44 (assigned to CO$_2$) in the Figures shows a later onset of carbon dioxide formation in 1/silica relative to Ir$_4$CO$_{12}$/silica. The MS trace of CO$_2$ in the Figures occurs for 1/silica as a small shoulder at 165° C., and two larger peaks at 176° C. and 229° C. This small shoulder is coincident with the maximum of the signal corresponding to amu 78 (assigned to phenyl fragment) for 1/silica. A 4.14 mg mass loss was observed via thermogravimetric analysis between 43° C. and 350° C. for the 1 mixed with silica system in the Figures. This compares with a theoretical prediction of 4.19 mg of mass loss for complete decarbonylation and calixarene combustion in this system.

IR Spectroscopy

The role of the calixphosphine ligand as electron donor is also apparent in an infrared spectroscopic comparison with Ir$_4$(CO)$_{11}$PPh$_3$. The infrared spectrum of 1 in CH$_2$Cl$_2$ exhibits bands in the v(CO) region at 2087, 2055, 2017, 1842, and 1818 cm$^{-1}$, with latter three stretching frequencies representing bridging CO groups. All of these bands are slightly red shifted compared with corresponding bands previously reported for Ir$_4$(CO)$_{11}$PPh$_3$ at 2088, 2056, 2020, 1887, 1847 and 1825 cm$^{-1}$. This data demonstrates higher electron density of Ir centers in 1 relative to Ir$_4$(CO)$_{11}$PPh$_3$, which gives rise to greater degrees of π back donation onto CO ligands.

Single Crystal Crystallography

The structure of 1 is further clarified using single-crystal X-ray diffraction as shown in the Figures. The calixphosphine ligand occupies an axial position, and the Ir—P bond forms an angle of 63.26(2°) below the basal plane of the tetrahedron, consisting of three bridging CO ligands. Ir—Ir bond lengths range from 2.70(6) to 2.78(6)Å and are in close agreement with bond distances in other phosphine-substituted Ir$_4$ tetrahedral cores with 60-valence electron count. 8 The two largest Ir—Ir distances in 1 occur in the two basal edges that are connected to the substituted Ir atom. The tilt angles formed between the basal plane and equatorial CO groups are 28.36 (4°), 30.17(6°), 30.97(0°), and their similarity implies minor steric interference of the calixphosphine ligand on $Ir_4$ cluster structure.

The effect of the calixphosphine ligand on electron density in the $Ir_4$ core in 1 can be indirectly investigated by examining asymmetry in the Ir—C bond distances involving bridging CO ligands. Previous studies correlate the presence of donor ligands in monosubstituted $Ir_4$ clusters to higher electron density on the substituted Ir atom. In these systems, there is asymmetry observed in the Ir—C bond distances of bridging CO ligands attached to the substituted Ir atom, wherein the Ir—C bond to the substituted Ir atom is shorter than the corresponding bond to the unsubstituted center 0.4 In 1, Ir—C bonds for the two bridging CO ligands attached to the substituted Ir center reveal similar asymmetry, which shortens Ir—C bond lengths involving the substituted Ir atom by 0.09(1) Å and 0.15(1) Å for the bridging CO between Ir(4) and Ir(2), and Ir(4) and Ir(3), respectively. This asymmetry is in stark contrast to Ir—C bond distances for the remaining, third, bridging CO ligand, which do not differ within experimental uncertainty, and demonstrates higher electron density on the substituted Ir atom in 1 as a result of the calixphosphine ligand.

TABLE 1

Selected Bond lengths [Å] for Structure of 1

| Bonding | Length (Å) |
|---|---|
| C(1)—O(1) | 1.136(12) |
| C(1)—Ir(1) | 1.927(12) |
| C(2)—O(2) | 1.128(12) |
| C(2)—Ir(1) | 1.914(12) |
| C(3)—O(3) | 1.142(11) |
| C(3)—Ir(1) | 1.909(11) |
| C(4)—O(4) | 1.134(11) |
| C(4)—Ir(2) | 1.889(11) |
| C(5)—O(5) | 1.140(12) |
| C(5)—Ir(2) | 1.875(12) |

TABLE 1-continued

Selected Bond lengths [Å] for Structure of 1

| Bonding | Length (Å) |
|---|---|
| C(6)—O(6) | 1.147(12) |
| C(6)—Ir(2) | 2.076(10) |
| C(6)—Ir(3) | 2.081(11) |
| C(7)—O(7) | 1.121(12) |
| C(7)—Ir(3) | 1.905(11) |
| C(8)—O(8) | 1.106(12) |
| C(8)—Ir(3) | 1.920(13) |
| C(9)—O(9) | 1.163(11) |
| C(9)—Ir(4) | 2.041(10) |
| C(9)—Ir(2) | 2.133(11) |
| C(10)—O(10) | 1.170(11) |
| C(10)—Ir(4) | 2.011(10) |
| C(10)—Ir(3) | 2.165(11) |
| C(11)—O(11) | 1.133(11) |
| C(11)—Ir(4) | 1.879(11) |

TABLE 2

Selected Bond angles [°] for Structure of 1

| Bond angle | Angle [°] |
|---|---|
| O(1)—C(1)—Ir(1) | 177.4(10) |
| O(2)—C(2)—Ir(1) | 178.0(11) |
| O(3)—C(3)—Ir(1) | 178.1(11) |
| O(4)—C(4)—Ir(2) | 177.9(10) |
| O(5)—C(5)—Ir(2) | 177.1(10) |
| O(6)—C(6)—Ir(2) | 137.8(9) |
| O(6)—C(6)—Ir(3) | 140.9(9) |
| Ir(2)—C(6)—Ir(3) | 81.3(4) |
| O(7)—C(7)—Ir(3) | 176.6(10) |
| O(8)—C(8)—Ir(3) | 173.4(11) |
| O(9)—C(9)—Ir(4) | 142.8(8) |
| O(9)—C(9)—Ir(2) | 134.7(8) |
| Ir(4)—C(9)—Ir(2) | 82.5(4) |
| O(10)—C(10)—Ir(4) | 143.2(8) |
| O(10)—C(10)—Ir(3) | 132.9(8) |
| Ir(4)—C(10)—Ir(3) | 83.6(4) |
| O(11)—C(11)—Ir(4) | 173.7(10) |

TABLE 3

Crystal data and structure refinement for 1

| | |
|---|---|
| Empirical formula | C77 H85 Ir4 O15 P |
| Formula weight | 2050.22 |
| Temperature | 135(2) K |
| Wavelength | 0.71073 Å |
| Crystal system | Triclinic |
| Space group | P-1 |
| Unit cell dimensions | a = 14.9086(9) Å   = 75.0170(10)°.° |
|  | b = 15.6994(9) Å   = 69.9510(10)°.° |
|  | c = 17.5646(10) Å   = 80.2370(10)°.° |
| Volume | 3715.8(4) Å$_3$ |
| Z | 2 |
| Density (calculated) | 1.832 Mg/m$_3$ |
| Absorption coefficient | 7.225 mm$_{-1}$ |
| F(000) | 1980 |
| Crystal size | 0.18 × 0.12 × 0.08 mm$_3$ |
| Crystal color/habit | yellow block |
| Theta range for data collection | 1.82 to 25.48°. |
| Index ranges | −17 <= h <= 17, −18 <= k <= 18, −21 <= l <= 21 |
| Reflections collected | 38890 |
| Independent reflections | 13541 [R(int) = 0.0741] |
| Completeness to theta = 25.00° | 99.3% |
| Absorption correction | Semi-empirical from equivalents |
| Max. and min. transmission | 0.561 and 0.336 |
| Refinement method | Full-matrix least-squares on F$_2$ |
| Data/restraints/parameters | 13541/2/888 |
| Goodness-of-fit on F$_2$ | 1.017 |

TABLE 3-continued

Crystal data and structure refinement for 1

| | |
|---|---|
| Final R indices [I > 2sigma(I)] | R1 = 0.0481, wR2 = 0.0960 |
| R indices (all data) | R1 = 0.0872, wR2 = 0.1116 |
| Largest diff. peak and hole | 1.861 and −1.259 e.$\text{Å}^{-3}$ |

TABLE 4

Crystal data and structure refinement for tert-butyl-calix[4]arene-(OPr)$_2$(OCH$_2$PPh$_2$)$_2$(Ir$_4$(CO)$_{11}$)$_2$

| | |
|---|---|
| X-ray ID | katz04 |
| Sample/notebook ID | 258X |
| Empirical formula | C98 H90 Ir8 O26 P2 |
| Formula weight | 3283.41 |
| Temperature | 150(2) K |
| Wavelength | 0.77490 Å |
| Crystal system | Monoclinic |
| Space group | C2/c |
| Unit cell dimensions | a = 31.338(3) Å   α = 90°. |
| | b = 13.7003(14) Å   β = 98.4900(10)°. |
| | c = 48.862(5) Å   γ = 90°. |
| Volume | 20748(4) Å$^3$ |
| Z | 8 |
| Density (calculated) | 2.102 Mg/m$^3$ |
| Absorption coefficient | 12.838 mm$^{-1}$ |
| F(000) | 12256 |
| Crystal size | 0.06 × 0.05 × 0.03 mm$^3$ |
| Crystal color/habit | yellow plate |
| Theta range for data collection | 2.88 to 27.85°. |
| Index ranges | −37 <= h <= 37, −16 <= k <= 16, −58 <= l <= 58 |
| Reflections collected | 101442 |
| Independent reflections | 19008 [R(int) = 0.0690] |
| Completeness to theta = 27.85° | 99.8% |
| Absorption correction | Semi-empirical from equivalents |
| Max. and min. transmission | 0.6994 and 0.5130 |
| Refinement method | Full-matrix least-squares on F$^2$ |
| Data/restraints/parameters | 19008/18/1258 |
| Goodness-of-fit on F$^2$ | 1.033 |
| Final R indices [I > 2sigma(I)] | R1 = 0.0544, wR2 = 0.1377 |
| R indices (all data) | R1 = 0.0602, wR2 = 0.1418 |
| Largest diff. peak and hole | 7.395 and −2.789 e.$\text{Å}^{-3}$ |

TABLE 5

Crystal data and structure refinement for tert-butyl-calix[4]arene-(OMe)$_2$(OCH$_2$PPh$_2$)$_2$(Ir$_4$(CO)$_{11}$)2

| | |
|---|---|
| X-ray ID | katz05 |
| Sample/notebook ID | 276X |
| Empirical formula | C94 H82 Ir8 O26 P2 |
| Formula weight | 3227.14 |
| Temperature | 133(2) K |
| Wavelength | 0.71073 Å |
| Crystal system | Monoclinic |
| Space group | P2(1)/c |
| Unit cell dimensions | a = 17.843(3) Å   α = 90°. |
| | b = 11.8513(19) Å   β = 99.136(2)°. |
| | c = 46.433(8) Å   γ = 90°. |
| Volume | 9694(3) Å$^3$ |
| Z | 4 |
| Density (calculated) | 2.211 Mg/m$^3$ |
| Absorption coefficient | 11.042 mm$^{-1}$ |
| F(000) | 6000 |
| Crystal size | 0.18 × 0.12 × 0.08 mm$^3$ |
| Crystal color/habit | yellow plate |
| Theta range for data collection | 0.89 to 25.47°. |
| Index ranges | −21 <= h <= 21, −14 <= k <= 14, −56 <= l <= 56 |
| Reflections collected | 143969 |
| Independent reflections | 17840 [R(int) = 0.0526] |
| Completeness to theta = 25.00° | 100.0% |

TABLE 5-continued

Crystal data and structure refinement for tert-butyl-
calix[4]arene-(OMe)$_2$(OCH$_2$PPh$_2$)$_2$(Ir$_4$(CO)$_{11}$)2

| | |
|---|---|
| Absorption correction | Semi-empirical from equivalents |
| Max. and min. transmission | 0.4720 and 0.2412 |
| Refinement method | Full-matrix least-squares on F$^2$ |
| Data/restraints/parameters | 17840/0/1222 |
| Goodness-of-fit on F$^2$ | 1.103 |
| Final R indices [I > 2sigma(I)] | R1 = 0.0334, wR2 = 0.0729 |
| R indices (all data) | R1 = 0.0405, wR2 = 0.0755 |
| Largest diff. peak and hole | 3.304 and −1.485 e.Å$^{-3}$ |

Example 3

Preparation and Characterization of Catalysts

Ir/γ-Al$_2$O$_3$ Catalyst: 5 wt % Ir

H$_2$IrCl$_6$ (hexachloroiridate) is dissolved in 30 ml DI water. Typical concentration of the solution is 9.13 mM for 5 wt % Ir loading. 1 g of γ-Al$_2$O$_3$ (Strem, 95 m$^2$/g) is added to aqueous solution of hexachloroiridate. The solution is stirred for 24 hours. Excess water is subsequently removed from samples by rotary evaporation at 50° C., and samples are dried in oven at 110° C. overnight. Samples are then calcined in O$_2$ flow (5% O$_2$, He balanced, 20 ml/min) at 400° C. for 1 hr. During calcination, the temperature increases at a rate of 10° C./min up to 400° C. Samples are evacuated at room temperature and held there for 1 hr. Samples are subsequently heated to 200° C. at a rate of 10° C./min and reduced in H$_2$ flow (15% H$_2$, He balanced, 30 ml/min) at 400° C. for 4 hrs.

Ir/γ-Al$_2$O$_3$ Synthetic Summary

The Figures demonstrate that Ir colloids that are approximately 0.7 nm in diameter can be synthesized at 5 wt % surface density on a γ-Al$_2$O$_3$ support, and that supports from Degussa and Strem produce similar particle size distributions that are within experimental error of each other. These colloids are considerably smaller than those previously reported for Ir/γ-Al$_2$O$_3$, which have been previously synthesized as in the diameter range of 2-3 nm, and have also been previously synthesized in the range of 4-8 nm.

Ir/TiO$_2$ Catalyst

H$_2$IrCl$_6$ (hexachloroiridate) is dissolved in 30 ml DI water. The typical concentration of the solution is 3.66 mM H$_2$IrCl$_6$ for 2 wt % Ir loading. 1 g of TiO$_2$ (Degussa P25 at 53 m$^2$/g) is added to the aqueous hexachloroiridate solution. The solution is then stirred for 24 hours at room temperature. Excess water is subsequently removed via rotary evaporation at 50° C., and samples are then dried in an oven at 110° C. overnight. Samples are subsequently calcined in O$_2$ flow (5% O$_2$, He balanced, 20 ml/min) at 400° C. for 4 hr. During calcination, the temperature increases at a rate of 10° C./min up to 400° C. Samples are cooled to room temperature under He purge and are then purged with He an additional 1 hr. Samples are reduced in H$_2$ flow (15% H$_2$, He balanced, 30 ml/min) at 200° C. for 2 hrs.

Ir/TiO$_2$ Synthetic Summary

The Figures demonstrate the observed average Ir particle size was 1.2±0.4 nm. Most Ir colloids synthesized by the procedure above are in the size range of less than 1 nm diameter, but a few Ir nanoparticles are larger than 2 nm. This colloid size distribution is considerably smaller than that previously reported in the literature for Ir supported on TiO$_2$, which is in the diameter range of 2.8 nm-4 nm.

Ir/MgO Catalyst

H$_2$IrCl$_6$ (hexachloroiridate) is dissolved in 30 ml DI water. The typical concentration of the solution is 3.66 mM H$_2$IrCl$_6$ for 2 wt % Ir loading. 1 g of MgO (Aldrich, 130 m$^2$/g) is added to the solution under vigorous stirring. The solution is subsequently stirred for 24 hours. Excess water is subsequently removed via rotary evaporation at 50° C., and samples are dried in oven at 110° C. overnight. Samples are then calcined in O$_2$ flow (5% O$_2$, He balanced, 20 ml/min) at 400° C. for 4 hr. During calcination, the temperature increases at a rate of 10° C./min up to 400° C. Samples are then cooled to room temperature under He purge, and are purged with He for an additional 1 hr. Samples are reduced in H$_2$ flow (15% H$_2$, He balanced, 30 ml/min) at 400° C. for 2 hrs.

Example 4

Below is a summary of reactions for coordinating a calixarene molecule to an Ir$_4$ metal core, which failed to work. In general, ligand substitution reactions of the tetrahedral cluster Ir$_4$(CO)$_{12}$ have been investigated with a focus on phosphine substituted derivatives of the type Ir$_4$(CO)$_{12-x}$(P)$_x$ (x=1-4). Such cluster compounds have been typically synthesized by a combined procedure that involves the activation of Ir$_4$(CO)$_{12}$ by thermolysis (Watson et al., *J. Organomet. Chem.* 693:1439-1448 (2008)) or using a reagent that promotes oxidative-decarbonylation, followed by direct reaction with the corresponding phosphine, which leads to formal replacement of COs by phosphine ligands (Watson et al., *J. Organomet. Chem.* 693: 1439-1448 (2008)).

We have carried out reactions for calixphosphine substitution in Ir$_4$(CO)$_{12}$ using both the approaches above. In the thermolysis approach, Ir$_4$(CO)$_{12}$ was directly reacted with corresponding calixphosphine ligands at high temperatures (90 C) for overnight. This failed to coordinate calixarene to iridium metal core. Also tried was the use of NMe$_3$O reagent to coordinatively unsaturated Ir$_4$(CO)$_{12}$ species in the presence of the calixphosphine ligands. However in both these approaches the $^{31}$P NMR spectrum shows a complex pattern suggesting multiple species and/or multiple products. The key here is that these approaches are not suitable for selective synthesis as it may lead to multiple substituted species. More selective mono-phosphine substitution could be achieved by the displacement of Br$^-$ from Ir$_4$(CO)$_{11}$Br$^-$ anions by a substituted phosphine ligands, as described above.

Example 5

Synthesis and Characterization of Calixarene-Bound Ir$_4$ Clusters: Systematic Variation of Number of Calixarene Phosphine Ligands Per Cluster The synthesis and characterization of Ir$_4$(CO)$_{12-x}$(L)$_x$, where x=2-5 and ligand L=tert-butylcalix[4]arene(OPr)$_3$ (OCH$_2$PPh$_2$) is described. The increasing temperature required for synthesis in proceeding along the series from 2 (70° C./12 h) to 4 (110° C./24 h) speaks to the increasing steric protection surrounding the metal cluster—one of the critical design goals of these syntheses. The other critical aspect—electronic control of the active site—is demonstrated by the series of FTIR spectra in FIG. 30. These spectra demonstrate that for $Ir_4$-based cores with greater amounts of phosphine substitution (x increasing in the series $Ir_4(CO)_{12-x}(L)_x$), the bound phosphine ligands increase the electron density within the $Ir_4$ cluster core to a larger extent. As a consequence, the Ir—C bond back donation is increased, causing a decrease in the C—O bond strength. This results in a significant red shift of the CO stretching frequencies (i.e. $CO_{terminal}$ peaks in 3: 2037; 1999; 1988 $cm^{-1}$ whereas $CO_{terminal}$ peaks in 2: 2065; 2039; 2004 $cm^{-1}$).

Synthesis and Characterization of $Ir_4(CO)_{10}L_2$ 2

Complex $Ir_4(CO)_{10}L_2$ (2) is synthesized by displacement of $Br^-$ and one CO ligand in $[Ir_4(CO)_{11}Br]^-$ by two equivalents of L. Treatment of $[Bu_4N][Ir_4(CO)_{11}Br]$ with two equivalents of L leads to a mixture of clusters 2 and $Ir_4(CO)_9L_3$ (3). Subsequent purification by column chromatography yields pure 2 (ca 30%). The presence of cluster 2 is verified by high-resolution mass spectrometry, which shows peaks corresponding to the cationic cesium adduct $[2Cs]^+$ (m/z=3128.95 (calculated); m/z=3129.17 (observed)). $^{31}P\{^1H\}NMR$ shows two singlet signals at 17.2 ppm and –11.13 ppm with equal intensitys (1.00:0.97). The lower field resonance is assigned to an axial binding phosphine ligand, and the higher field resonance is assigned to an equatorial binding ligand. The presence of a basal plane created by bridging CO ligands is verified via IR spectroscopy, which shows bands in the regions for both terminal and bridging ligands. The strongest IR band is observed at 2039 $cm^{-1}$. Compared to the IR spectrum of 1 (strongest IR band is observed at 2055 $cm^{-1}$), a red shift is clearly observed and indicates a weaker C—O bond, and, therefore, a stronger Ir—C bond. The latter is consistent with more electron rich Ir due to the two calixarene ligands in 2 relative to 1. Single crystal structure data is in progress via X-ray diffraction.

Synthesis and Characterization of $Ir_4(CO)_9L_3$ 3

Treatment of $[Ir_4(CO)_{11}Br]^-$ with three equivalents of ligand L at 70° C. leads to the formation of 3 as a yellow powder (yield: >90%). The complex is purified via column chromatography and crystallized by layering a chloroform solution with isopropyl alcohol. The high-resolution ESI mass spectrum of 3 shows peaks corresponding to the cationic radical complex $[3]^{+\cdot}$ (m/z=3940.87 (observed); m/z=3940.67 (calculated)). $^{31}P\{^1H\}NMR$ spectroscopic data show two peaks at 18.39 ppm and –11.30 ppm with relative intensity ratios of 1.97 to 1.00. This implies that in 3, two of the three phosphine ligands occupy equivalent positions. The lower-field resonance is assigned to one ligand occupying an axial position, while the higher-field resonance is a result of two phosphine ligands binding both in equatorial positions.

Figure 30:
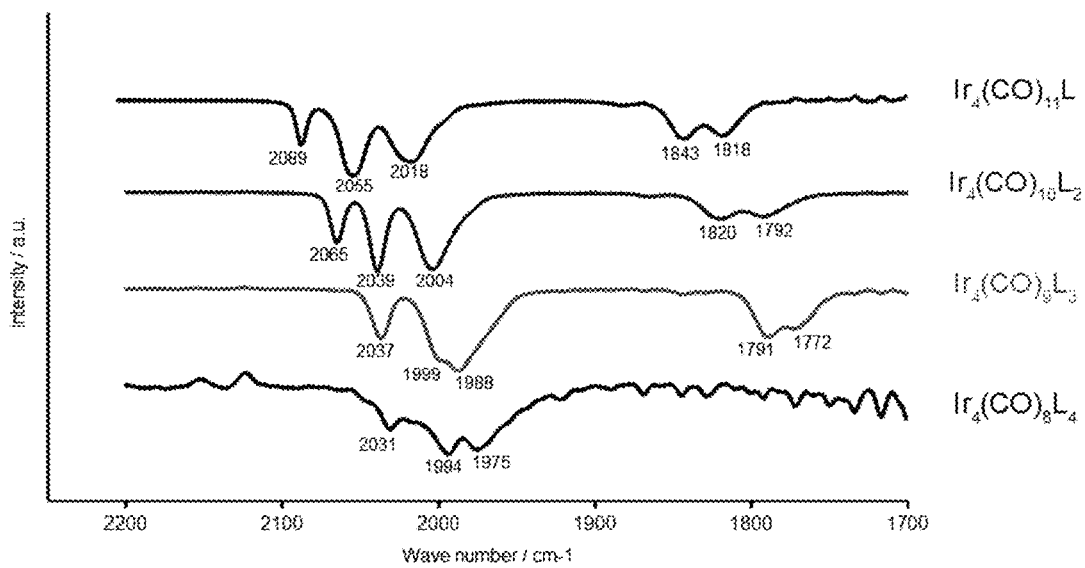
FIG. 30 shows IR data for metal clusters synthesized having the general formula Ir$_4$(CO)$_{12-x}$L$_x$, where x=1, 2, 3, 4.
Figure 31:
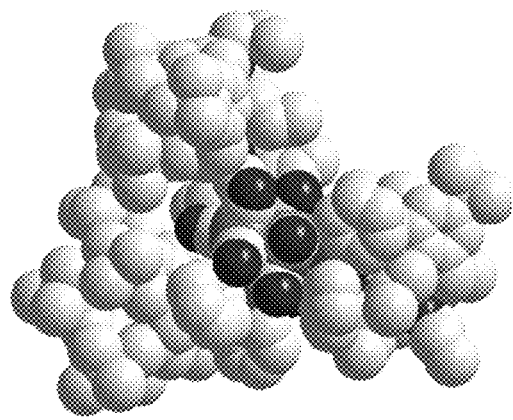
FIG. 31 shows (a) space filling view of the structure of Ir$_4$(CO)$_9$L$_3$ 3, with accessible cluster binding sites in view, and (b) less accessible cluster sites in view.
Figure 31:
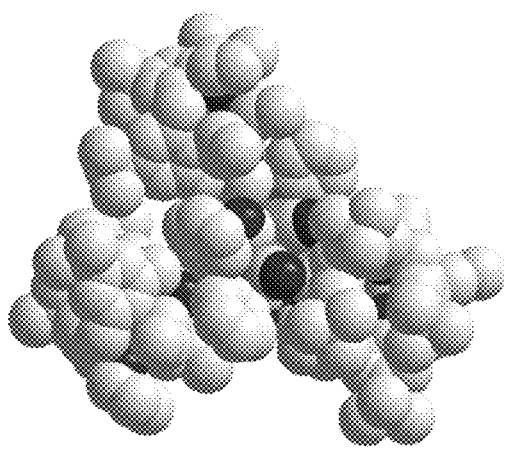
Figure 32:
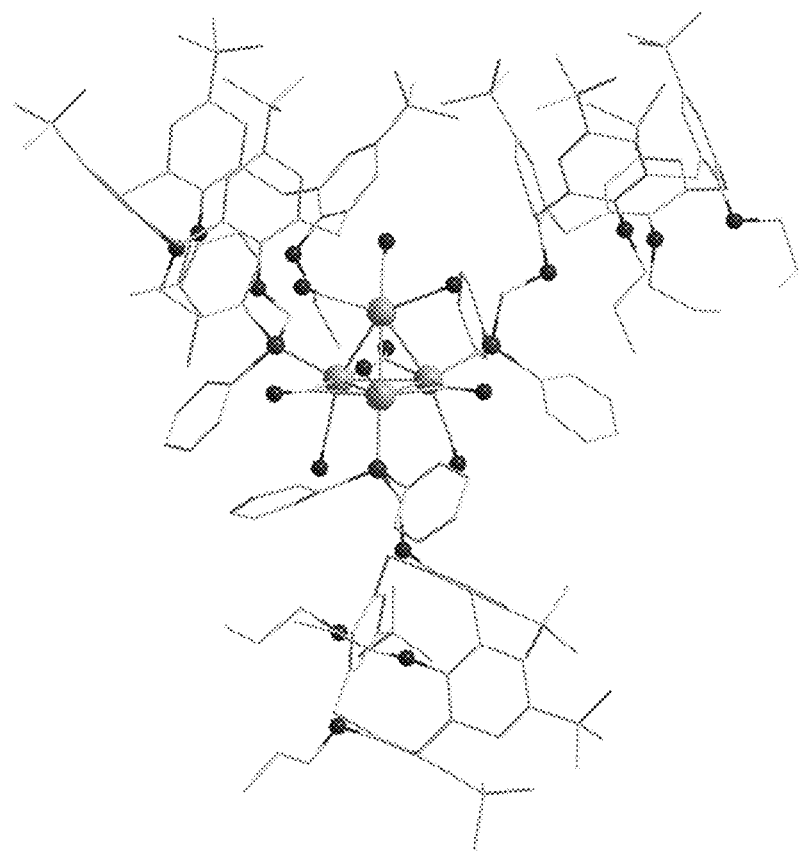
FIG. 32 shows bond angles and lengths within the basal plane, derived from the crystal structure of Ir$_4$(CO)$_9$L$_3$ via X-ray diffraction (top).
Figure 32:
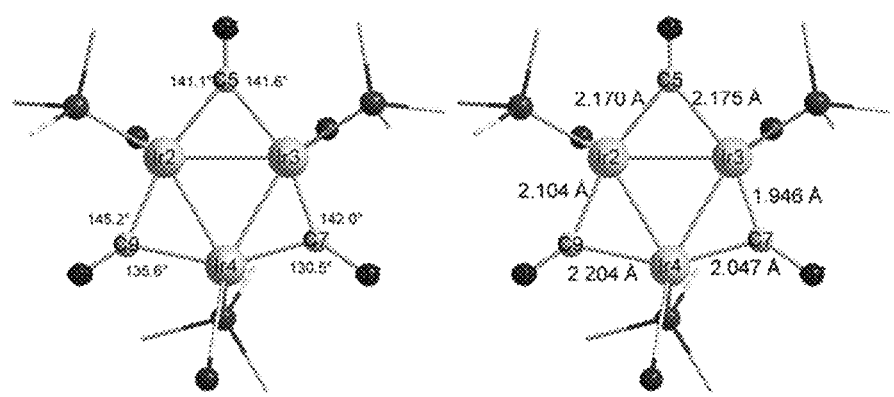

Single crystal structure data via X-ray diffraction is shown in FIGS. 31 and 32 below and show the $Ir_4$ cluster core bound to three ligands L. Two of the phosphine ligands L occupy equivalent equatorial positions while the third ligand L is axial bound. To gain insight into the accessibility of 3 for reactants as well as for placing additional calixarene ligands into the structure (as in 4 and a proposed x=5 version), a molecular model based on a space-filling representation is shown in FIG. 30. This model demonstrates that while much of the $Ir_4$ metal core is protected, one face of the cluster is rather exposed and accessible (see FIG. 31(a)). Based on this model, additional calixarene ligand in 4 would be bound to the apical Ir position (verification via single-crystal X-ray diffraction of 4 is pending). As in 1, the bulky phospine ligands L in 3 influence both terminal and bridging ligands. The two equatorial-bound phosphine ligands cause a higher distortion of the bridging CO ligands than the single axial-bound phosphine ligand. Therefore, the Ir(2)-C(9)-O(9) angle of 145.2° and the Ir(3)-C(7)-O(7) angle of 142.0° are larger than corresponding values for the Ir(4)-C(9)-O(9) angle of 135.6° and Ir(4)-C(7)-O(7) angle of 130.5°.

The central phenomenon driving the differences in bond angles involving Ir(2)/Ir(3) and Ir(4) above is a slight asymmetry, which interrupts what would otherwise be a perfect three-fold symmetry, in the basal plane of 3. This asymmetry arises because of the axial-bound phosphine ligand: the Ir(4)-bound terminal CO-ligand prefers a position that is staggered with respect to the phenyl groups of the axial-bound phosphine ligand. This asymmetry is also manifested in the Ir—$CO_{bridging}$ distances. The Ir(4)-C(9) and the Ir(2)-C(9) bond lengths (2.204 Å and 2.104 Å) are both larger than the corresponding Ir(4)-C(7) and the Ir(3)-C(7) bond lengths (2.047 Å and 1.946 Å). A control between two iridium atoms bound to equatorial ligands is that the Ir(2)-C(5) and the Ir(3)-C(5) bond lengths are almost equal (2.170 Å and 2.175 Å). The Ir—$CO_{terminal}$ bond lengths vary from 1.850 Å to 1.960 Å and show no significant dependence of the nature of the bound Ir atom. All Ir—Ir distances are within 2.697 Å and 2.757 Å.

Synthesis and Characterization of $Ir_4(CO)_8L_4$ 4

Treatment of $[Ir_4(CO)_{11}Br]$ with four equivalents of L at 110° C. leads to the formation of a dark brown solution. According to high-resolution ESI mass spectrometry, the solution contains the $Ir_4(CO)_8L_4$ cluster ($[4]^{+\cdot}$; m/z=4887.01 (observed); m/z=4887.30 (calculated)). The $^{31}P\{^1H\}NMR$ spectroscopic data of the as-made solution show very weak signals and one sharp singlet at 24.4 ppm. After column purification, the $^{31}P\{^1H\}NMR$ spectrum contains only weak signals, which have yet to be assigned. The same solution shows a clear red shift of the CO stretching frequencies relative to 3 in the FTIR spectrum (4: 2031; 1994; 1975 $cm^{-1}$; 3: 2037; 1999; 1988 $cm^{-1}$), consistent with the trend expected for tetra substitution.

Synthesis and Characterization of $Ir_4(CO)_7L_5$ 5

A single example in the literature was found regarding the only known pentasubstituted $Ir_4$ cluster $Ir_4(CO)_7L'_5$ (L'=Triaza-phospha-adamantane) (see Darensbourg, D. J.; Beckford, F. A.; Reibenspies, J. H. *Journal of Cluster Science* 2000, 11, 95-107). This is obtained by the reaction of $Ir_4(CO)_{12}$ and the ligand in refluxing toluene. The synthesis of this pentasubstituted $Ir_4(CO)_7L_5$ is planned via treatment of $Ir_4(CO)_8L_4$ with a single equivalent of L. What should help this synthesis is the fact that, due to its electron richness, the metal core becomes more susceptible to additional ligand L substitution. Sterically, of course, this substitution becomes more difficult with added number of ligands.

Example 6

Catalysis with Supported Calixarene-Bound $Ir_a$ Clusters: Support Effect and Role of Calixarene as Stabilizing Ligand During Ligand Exchange Processes Accompanying Catalysis

Synthesis of Supported $Ir_4(CO)_{12}$ on MgO: Control Catalyst Based on Literature MgO was first pretreated in U-tube quartz reactor under dry 20% $O_2/N_2$ flow (0.8 cm$^3$ s$^{-1}$ g$^{-1}$) at 400° C. for a period of 4 hours. Subsequently, the flow was changed to He (0.8 cm$^3$ s$^{-1}$ g$^{-1}$), and the sample was calcined at this temperature for 10 hours. Reactor was cooled down to room temperature under flow of He and transferred to a glovebox without contacting either air or moisture. $Ir_4(CO)_{12}$ and MgO were mixed under Ar atmosphere in a glovebox in a Schlenk flask in amount to give 1 wt % Ir material. Hexane was added and the resulting slurry was stirred for 1 h. A similar procedure was implemented to anchor a monocalixarene-bound $Ir_4$ clusters for the TEM study below. The solvent was evaporated in vacuo, and the residue was dried under vacuum at room temperature overnight, and then was kept under inert atmosphere. The required amount of catalyst precursor was transferred to a glass reactor without exposure to air/moisture. These conditions were chosen based on experimental procedures developed by the research group of supported cluster catalysis pioneer Bruce Gates, with a slight variation in conditions for pretreatment (calcination time and conditions, namely calcination under vacuum by Gates' procedure with total duration of 16 h versus calcination under He flow by Katz group procedure with total duration of 18 h). S. D. Maloney, F. B. M. Van Zon, M. J. Kelley D. C. Koningsberger, B. C. Gates, *Catal. Lett.* 1990, 5, 161-168; F. B. M. Van Zon, S. D. Maloney, B. C. Gates, and D. C. Koningsberger, *J. Am. Chem. Soc.* 1993, 115, 10317-10326; N. D. Triantafillou and B. C. Gates, *J. Phys. Chem.* 1994, 98, 8431-8441; 0. S. Alexeev, D.-W. Kim, B. C. Gates, *J. Mol. Catal. A: Chem.* 2000, 162, 67-82.

Synthesis of Supported Calixarene-Bound $Ir_4$ Clusters on $SiO_2$-500

Figure 33:
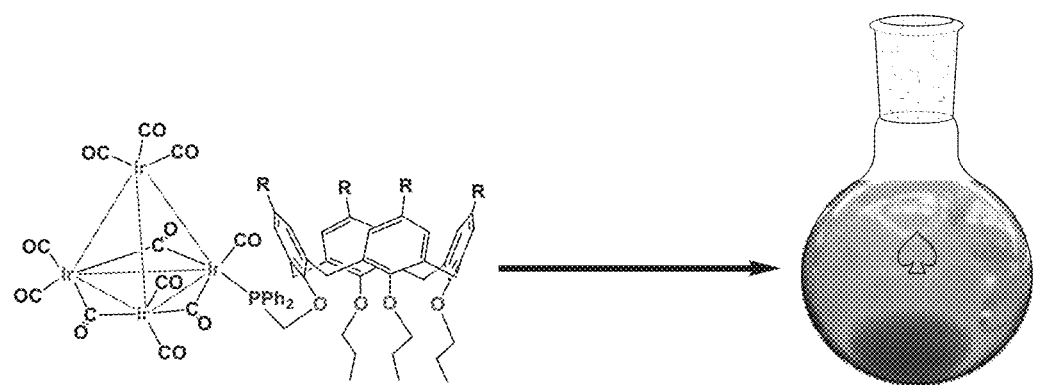
FIG. 33 shows a schematic of synthesis of immobilized calixarene-bound 11'$_4$ clusters on a silica support is illustrated above for the Ir$_4$(CO)$_{11}$L 1 cluster. The treatment of the dissolved cluster in hexane with silica at room temperature leads to the immobilization of the cluster, even without solvent evaporation, and the yellow solid shown on the right. A typical supported iridium density on the surface of silica is 20-25 nm$^2$ per Ir$_4$-calixarene on the surface.

$SiO_2$ (Aerosil 200) was first calcined under dry 20% $O_2/N_2$ flow (1.2 cm$^3$ s$^{-1}$ g$^{-1}$) at 500° C. for 4 hours followed by He (0.9 cm$^3$ s$^{-1}$ g$^{-1}$) at 500° C. for 10 hours. Thereafter, the sample was transferred to a glovebox without contact to air/moisture. $Ir_4$ carbonyl cluster with phosphine ligand was mixed with silica in a glovebox to give a 1 wt % Ir material. Hexane was added under inert atmosphere. Dissolution of cluster was observed during the first minute which was evident by bright yellow color of the liquid over the silica. Immobilization of catalyst precursor occurred in 10-15 minutes which was evident by discoloration of the solution and formation of yellow solid (FIG. 33). The resulting material was stirred for 1 hour to ensure the total immobilization of the cluster. After evaporation of solvent the remaining solid was dried at room temperature under vacuum overnight, and then kept under inert atmosphere. The required amount of catalyst was transferred to a quartz reactor air-free, and the dead volume consisting of volume leading up to reactor valves was replaced by He, and the reaction started without additional pretreatment. A similar procedure was also implemented for the immobilization of calixarene-bound $Ir_4$ clusters on TMS-capped $SiO_2$-500. Silica capping for these materials was accomplished using excess hexamethyldisilazane based on literature precedent.

Figure 34:
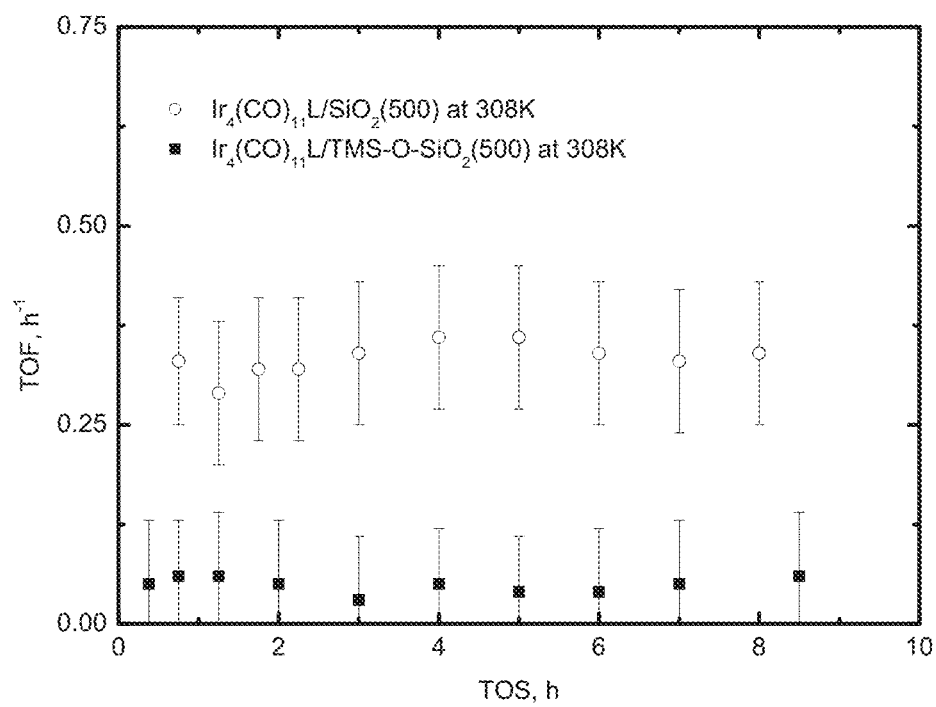
FIG. 34 shows hydrogenation of ethylene over iridium carbonyl catalysts at 308K: 15% H$_2$, 5% C$_2$H$_4$ balanced with He; total flow rate at STP: 4.6 cm$^3$ s$^{-1}$ g$^{-1}$; no pretreatment. The data clearly show a significant effect of SiOH defect sites on catalysis rate.

Ethylene Hydrogenation Catalysis at 308 K Using Supported $Ir_4(CO)_{11}L$ 1 as Catalyst: A Comparative Study of the Effect of Support SiOH Versus SiOTMS Groups on Catalysis Use of $Ir_4(CO)_{11}L$ 1 supported on uncapped (silica surface rich with native silanols) $SiO_2$-500 leads to an active and stable gas-phase ethylene hydrogenation catalyst at 35° C. as shown by open symbols in FIG. 34. $^{31}P$ CP/MAS NMR spectra (not shown here) of materials before and after catalysis at 308 K confirm integrity of the supported cluster $Ir_4(CO)_{11}L$ 1 by the absence of a downfield-shifted resonance characteristic of aggregated $Ir_x$ entities. Comparison with the same cluster 1 supported on TMS-capped $SiO_2$-500 is shown by dark symbols in FIG. 34: ethylene hydrogenation catalysis is inactive upon TMS capping of the surface. This result is in stark contrast to observations with supported platinum catalysts, and suggests that SiOH groups are required for catalysis. This forms the basis of ongoing studies with other supported clusters consisting of $Ir_4(CO)_9L_3$ 3, which are performed at higher temperatures, so as to increase catalyst activity and differentiate more between active and inactive catalysts when comparing TMS-capped and uncapped $SiO_2$-500 support surfaces.

Figure 35:
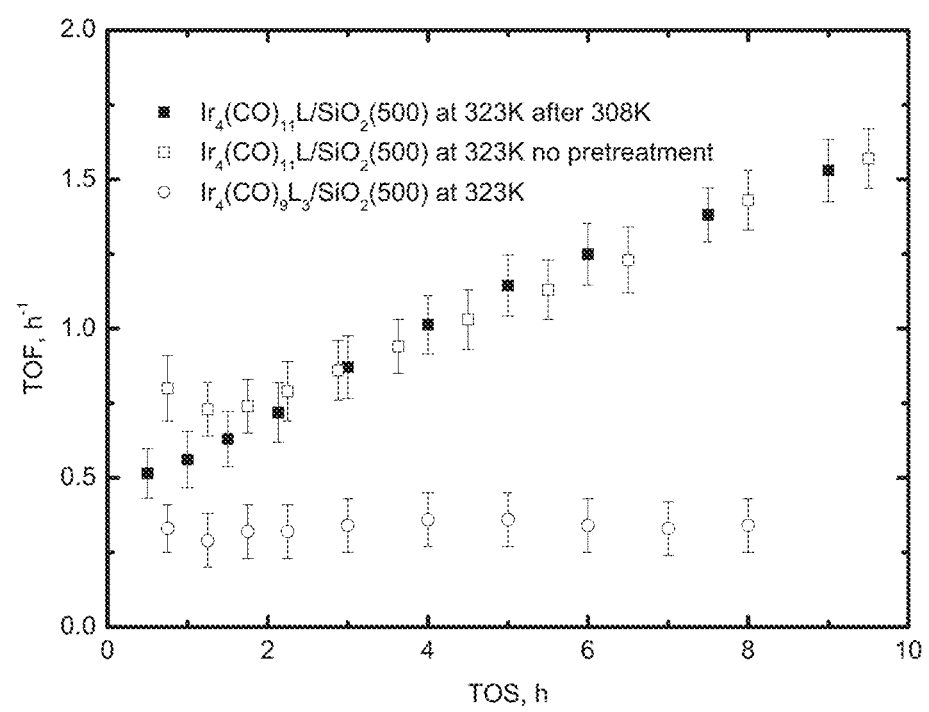
FIG. 35 shows hydrogenation of ethylene over iridium carbonyl catalysts: 15% H$_2$, 5% C$_2$H$_4$ balanced with He; total flow rate at STP: 4.6 cm$^3$ s$^{-1}$ g$^{-1}$; pretreatment 26 and 9.5 h (for ■ Ir$_4$(CO)$_{11}$L/SiO$_2$ and ○ Ir$_4$(CO)$_9$L$_3$/SiO$_2$, respectively) on stream of reactive gases at 308K, and no pretreatment for □ Ir$_4$(CO)$_{11}$L/SiO$_2$.
Figure 36:
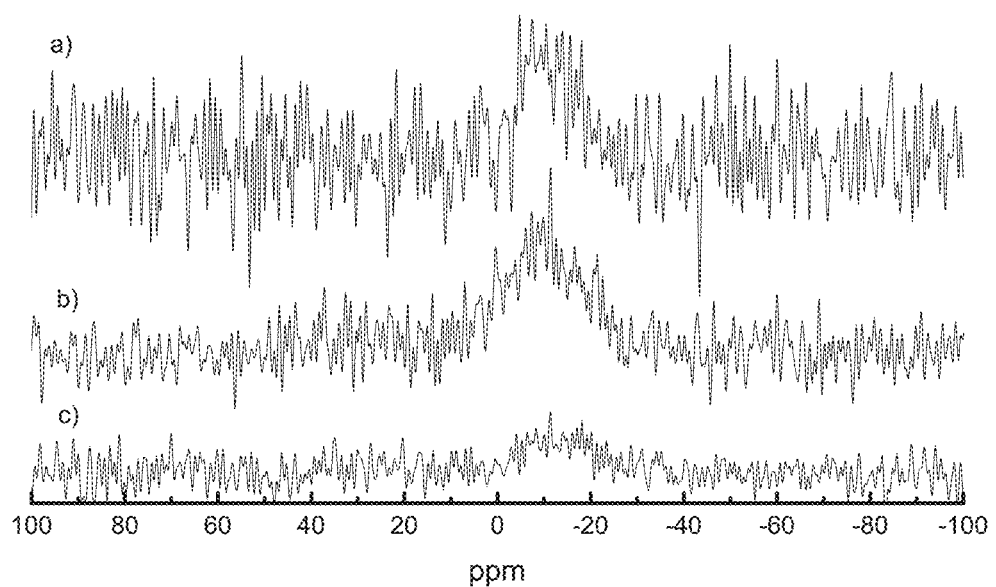
FIG. 36 shows $^{31}P$ CP/MAS solid state NMR spectra of Ir$_4$(CO)$_{11}$L/SiO$_2$(500) a) before the catalysis; b) after 10 h on stream at 308K; c) after 110 h on stream at 323K. Reactive gas stream composition: 5% ethylene, 15% hydrogen, balanced with helium.

Ethylene Hydrogenation Catalysis at 323 K Using $SiO_2$-500-Supported $Ir_4(CO)_{11}L$ 1 and $Ir_4(CO)_{11}L_3$ 3 as Catalysts: A Comparative Study of the Effect of Additional Calixarene Ligands on Cluster Stability During Catalysis Compared to FIG. 34, which demonstrates a steady-state rate of ethylene hydrogenation catalysis at 308 K, increasing the reaction temperature to 323 K when using $Ir_4(CO)_{11}L$ 1 supported on $SiO_2$-500 as catalyst leads to the lack of a steady-state rate of catalysis, as shown in FIG. 35. $^{31}P$ CP/MAS NMR spectroscopy confirms the presence of extended aggregation of iridium metal in the 1 supported on $SiO_2$-500 sample after catalysis at 323 K via presence of a characteristic downfield resonance. Visual inspection of the used catalyst 1 supported on $SiO_2$-500 sample after catalysis at 323 K shows a metallic grey discoloration that is consistent with aggregation (formation of bulk iridium metal) and is significantly different from the bright yellow color of the catalyst prior to reaction. The lack of decomposition of the $Ir_4(CO)_{11}L$ 1 supported on $SiO_2$-500 after catalysis at 308 K as well as its decomposition after catalysis at 323 K can be ascertained via $^{31}P$ CP/MAS NMR spectroscopy, which is shown in FIG. 36. The resonance corresponding to bound phosphine is retained after catalysis at 308 K in FIG. 36b; however, this resonance disappears almost completely after catalysis at 323 K in FIG. 36c.

However, unlike $Ir_4(CO)_{11}L$ 1 supported on $SiO_2$-500, use of $Ir_4(CO)_9L_3$ 3 supported on $SiO_2$-500 leads to a stable catalyst at 323 K, which achieves a well-defined steady-state rate of ethylene hydrogenation, as shown in FIG. 36. This demonstrates the added steric protection of the $Ir_4$ core against aggregation, which three calixarenes provide over a single calixarene ligand. This steric protection can be viewed via a space-filling model of the structure of 3 derived from single-crystal X-ray diffraction in FIG. 31, and is only possible with multiple calixarenes in 3, which envelop the metal core, as opposed to a single calixarene bound to the Ir$_4$ cluster in 1.

Figure 37:
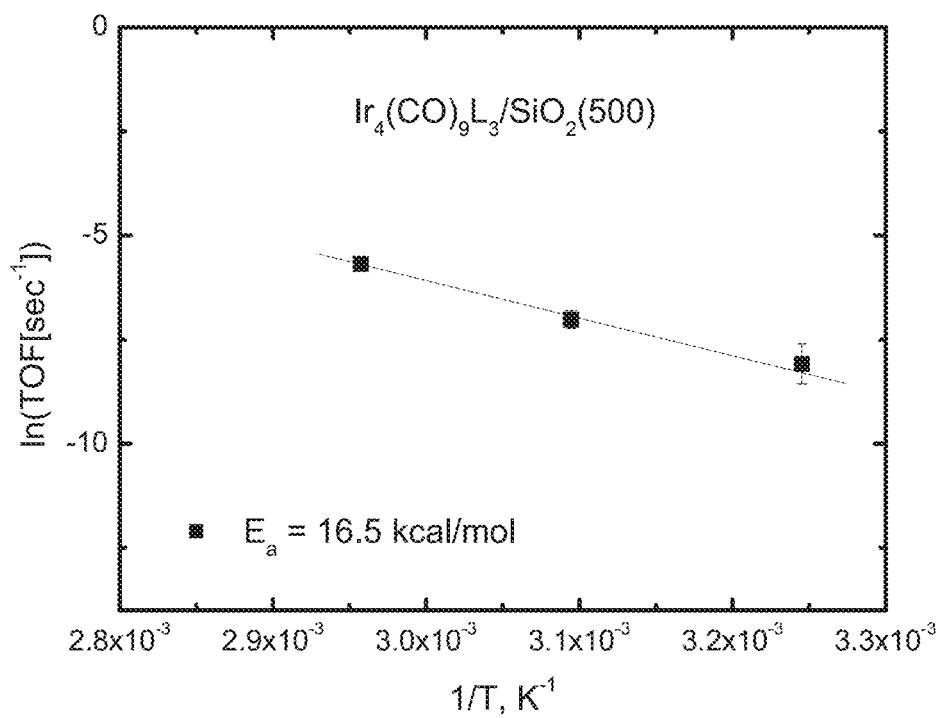
FIG. 37 shows an Arrhenius plot for the determination of activation energy for ethylene hydrogenation using catalyst 3 on SiO$_2$-500 after storage for the hydrogenation of ethylene. Hydrogenation of ethylene over Ir$_4$(CO)$_9$L$_3$/SiO$_2$ catalyst: 15% H$_2$, 5% C$_2$H$_4$ balanced with He; total flow rate at STP: 4.6 cm$^3$ s$^{-1}$ g$^{-1}$; pretreatment: 15% H$_2$, 5% C$_2$H$_4$ balanced with He; total flow rate at STP: 4.6 cm$^3$ s$^{-1}$ g$^{-1}$; for 9.5 h at 308 K followed by 8 h at 323 K followed by 3 days in closed reactor sealed over Ar flow at room temp.

The Ir$_4$(CO)$_9$L$_3$ 3 supported on SiO$_2$-500 showed stable steady-state approaches at temperatures up to 65° C., which was the highest temperature investigated. This allowed the calculation of an activation energy for the catalyzed reaction of 69 kJ/mol (16.5 kcal/mol) for 3 supported on SiO$_2$-500 after storage catalyst, using data in FIG. 37.

Stability Comparison with Ir$_4$(CO)$_{12}$ on MgO

Figure 38:
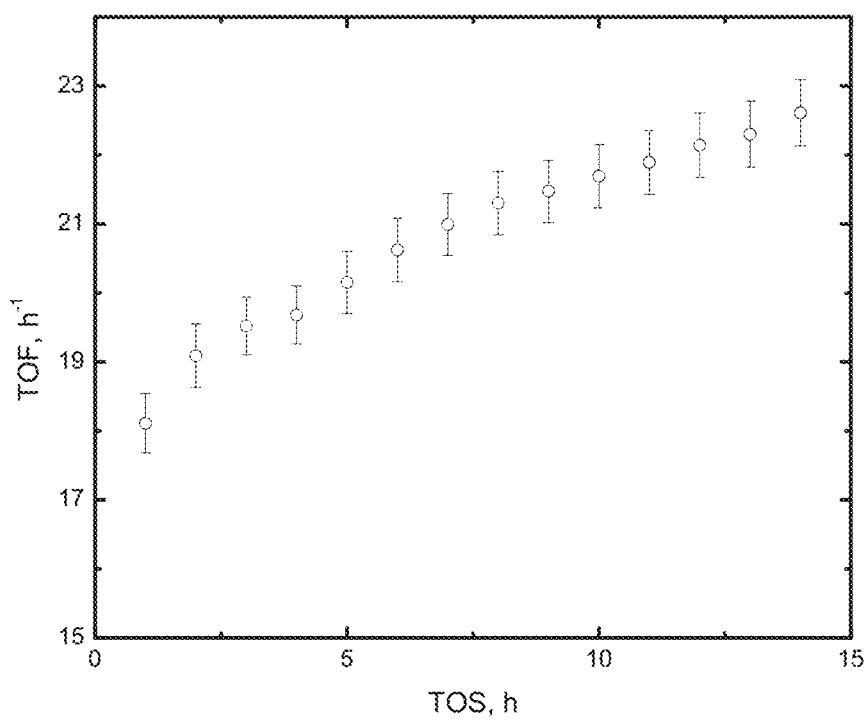
FIG. 38 shows hydrogenation of ethylene over Ir$_4$(CO)$_{12}$/MgO(400) catalyst: 15% H$_2$, 5% C$_2$H$_4$ balanced with He; total flow rate at STP: 6.7 cm$^3$ s$^{-1}$ g$^{-1}$; at 323 K; pretreatment 20 h under flow of 15% H$_2$, 5% C$_2$H$_4$ balanced with He at 308K.

Comparison with Ir$_4$(CO)$_{12}$ on MgO is appropriate because this catalyst is known to have strong metal cluster-support interactions, which should disfavor aggregation and increase robustness of the supported Ir$_4$ core. Ir$_4$(CO)$_{12}$ was anchored on MgO as described above, and was pretreated on stream with flowing reactants for ethylene hydrogenation at 308 K using 15% H$_2$, 5% C$_2$H$_4$ balanced with He; total flow rate at STP: 6.7 cm$^3$ s$^{-1}$ g$^{-1}$ for a period of 20 hours. Afterwards, catalysis was continued at the same flowrate except at a higher temperature of 323K. Results shown in FIG. 38 demonstrate a lack of stable catalyst during the course of 15 hours on stream at 323K, consistent with a degradation of the supported catalyst under these conditions. This degradation is also supported by a visual color change of the catalyst after reaction, which was slightly different from the original catalyst prior to reaction. This suggests degradation of the iridium cluster during catalysis, and demonstrates the importance of the calixarene ligand (i.e. in comparison with results when using Ir$_4$(CO)$_9$L$_3$ on silica) in retaining stability of the metal cluster core during ligand exchange processes accompanying catalysis. This is all the more telling because MgO is known to have a strong interaction as ligand with the Ir$_4$ core, (A. M. Argo, J. F. Odzak, F. S. Lai, and B. C. Gates, Nature 2002, 415, 623; Z. Xu, F.-S. Xiao, S. K. Purnell, O. Alexeev, S. Kawi, S. E. Deutsch, and B. C. Gates, Nature 1994, 372, 346) and suggests that the steric protection offered by the three calixarene ligands in Ir$_4$(CO)$_9$L$_3$ on silica is greater than that of a strongly interacting inorganic oxide support such as MgO.

Stability Comparison with Ir$_4$(CO)$_{11}$PPh$_2$Me on SiO$_2$-500

Figure 39:
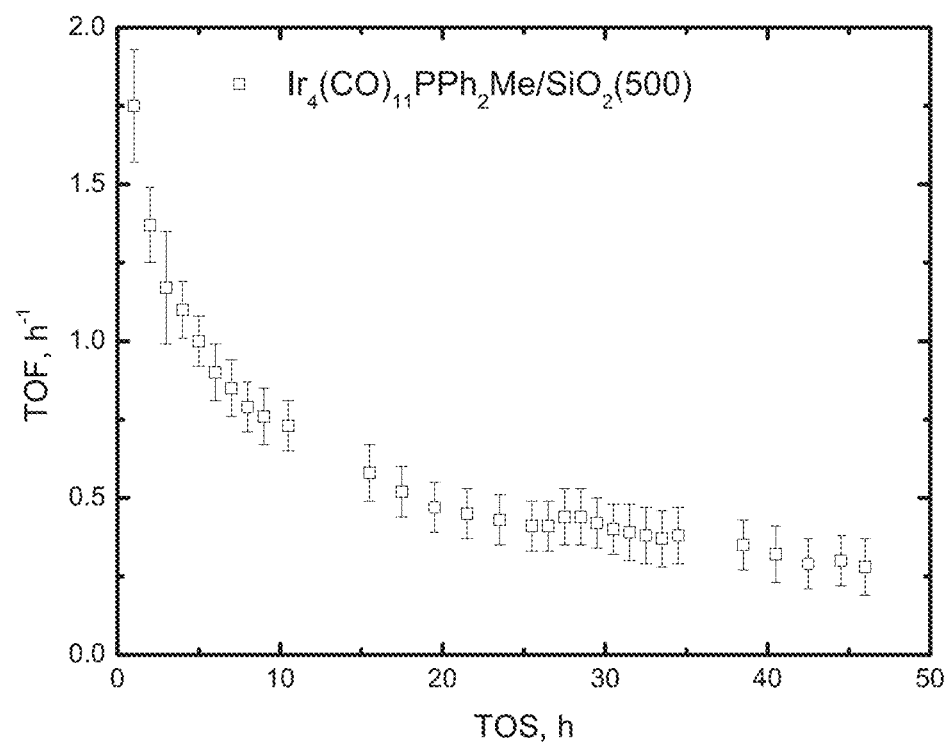
FIG. 39 shows hydrogenation of ethylene over Ir$_4$(CO)$_{11}$PPh$_2$Me/SiO$_2$(500) catalyst: 15% H$_2$, 5% C$_2$H$_4$ balanced with He; total flow rate at STP: 4.65 cm$^3$ s$^{-1}$ g$^{-1}$; no pretreatment

Comparison using Ir$_4$(CO)$_{11}$PPh$_2$Me is appropriate because this phosphine-bound Ir$_4$ cluster lacks a calixarene ligand but still contains a methyl diphenylphosphine ligand. Ir$_4$(CO)$_{11}$PPh$_2$Me was synthesized in the same fashion as Ir$_4$(CO)$_{11}$L, except instead of adding calixarene phosphine, commercially available PPh2Me was used. Ir$_4$(CO)$_{11}$PPh$_2$Me was subsequently anchored on silica using identical procedures to those described for Ir$_4$(CO)$_{11}$L, and was evaluated without pretreatment as a catalyst for ethylene hydrogenation at 308 K using 15% H$_2$, 5% C$_2$H$_4$ balanced with He; total flow rate at STP: 4.65 cm$^3$ s$^{-1}$ g$^{-1}$. Results shown in FIG. 39 demonstrate a lack of stable catalyst during the course of 45 hours on stream, consistent with a degradation of the supported catalyst under these conditions. This degradation is also supported by a visual color change of the catalyst after reaction (i.e. after 45 hours on stream), which shows the presence of a metallic grey luster that was not present in the pale yellow original catalyst prior to reaction. This suggests aggregation of the iridium cluster during catalysis, and demonstrates the importance of the calixarene ligand (i.e. in comparison with results when using both Ir$_4$(CO)$_{11}$L as well as Ir$_4$(CO)$_9$L$_3$ on silica) in retaining stability of the metal cluster core during ligand exchange processes accompanying catalysis.

Example 7

Diversification of Functional Groups that Bind to Metal Clusters: P-Containing Substituents Synthesis of Calix[4]arene Phosphite

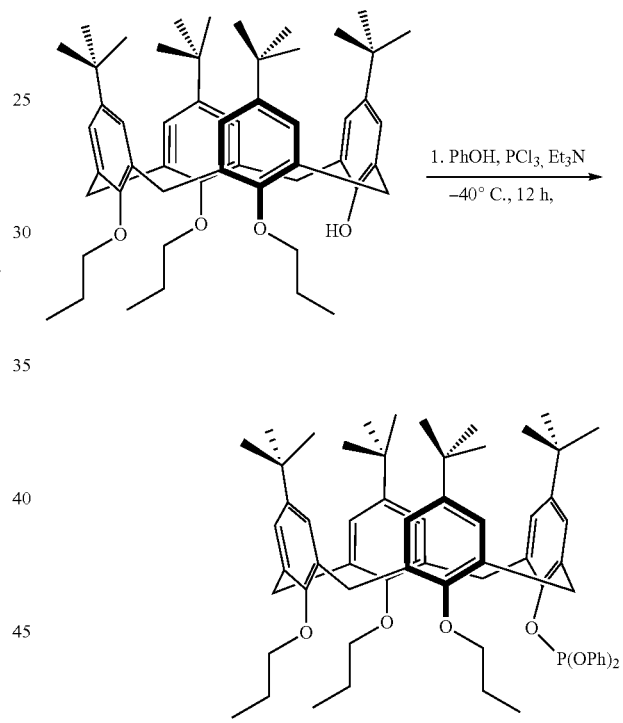

In a 250 mL rb flask equipped with magnetic stirrer tris-propoxy-4-t-butyl-calix[4]arene (775 mg, 1 mmol, 1 equiv.) was added. This was dissolved in 100 mL of anhydrous toluene (freshly distilled over sodium). To this flask 10 mL of Et$_3$N (freshly distilled over CaH$_2$) was added. To this flask cooled to −40° C. in a cryobath PhOH (185 mg, 2 mmol, 1 equiv) was added in a 2 mL solution in toluene. The reaction mixture was stirred for 30 minutes followed by addition of 515 μL of 2(M) PCl$_3$ in CH$_2$Cl$_2$ (140 mg, 1.03 mmol, 1.03 equiv) over 30 minutes. The reaction was kept stirring at −40° C. for overnight and then warmed up to room temperature. The crude reaction mixture indicated exclusive formation of calix[4]arene phosphite by $^{31}$P NMR (128 ppm).

Synthesis of Calix[4]arene Phosphinite

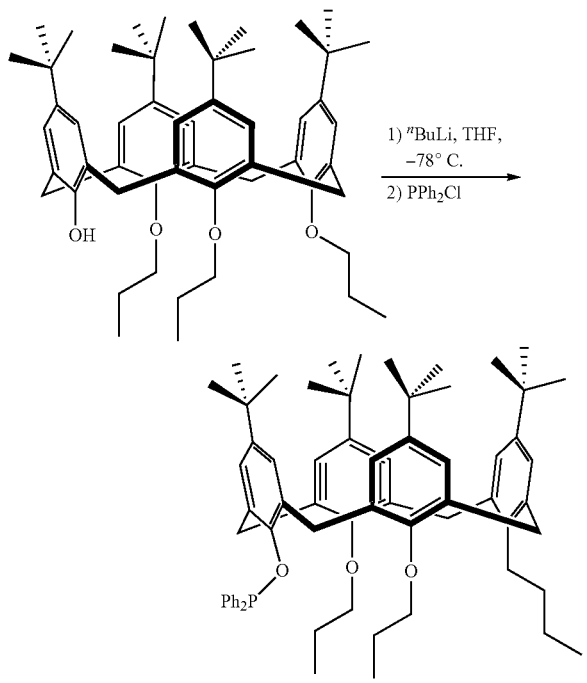

In a 100 mL round bottom flask equipped with magnetic stirrer, trispropoxy t-butyl calix[4]arene (387 mg, 0.5 mmol, 1 equiv) was dissolved in 30 mL anhydrous THF and was cooled to −78° C. in a dry ice bath with vigorous stirring for 10 minutes. To this flask, 1.6(M) "BuLi (400 μL, 0.64 mmol, 1.28 equiv) in hexane was added slowly during the course of five minutes. The reaction flask turned pale orange from colorless soon after addition, indicating formation of phenolate. After 1 hour, chloro diphenyl phosphine (100 μL, 123 mg, 0.56 mmol, 1.12 equiv) was added via gas-tight syringe. The reaction was allowed to warm to room temperature and was stirred for overnight. The solvent was removed under rotary evaporation, and the crude residue was subjected to flash chromatography on silica gel with anhydrous toluene as eluent ($R_f$=0.88). A colorless, viscous oily residue was isolated upon removal of solvent, weighing 350 mg (74% yield). $^1$H NMR (400 MHz, in $C_6D_6$, δ in ppm): 7.9 (m, 4H), 7.3-7.6 (m, 8H), 7.2 (s, 2H), 7.0 (s, 4H), 4.35 (t, 4H, 13.2 Hz), 3.8 (m, 2H), 3.7 (m, 4H), 3.2 (d, 2H, 13 Hz), 3.1 (d, 2H, 13 Hz), 2.3 (m, 4H), 1.9 (m, 4H), 1.3 (s, 18H), 1.1 (t, 6H, 7 Hz), 0.9 (t+s, 12H, 7 Hz), 0.65 (s, 9H). $^{13}$C NMR (100.6 MHz, in $C_6D_6$, δ in ppm): 155.2, 154.1, 144.0, 144.2, 137.5, 136.2, 135.8, 132.3, 131.6, 129.6, 129.0, 127.6, 125.8, 125.3, 125.0, 124.6 (Ar), 77.7, 77.5, 76.1 (α $CH_2$ of "Pr), 34.0, 32.2 (br $CH_2$), 31.8, 31.6, 31.3 ($^t$Bu), 23.5, 23.1, 21.2 (β $CH_2$ of "Pr), 10.7, 10.6, 9.8 ($CH_3$ of "Pr). $^{31}$P NMR: 122.8 ppm (in THF).

Synthesis and Characterization of the Compound $Ir_4(CO)_{11}L$ (L=tert-butylcalix[4]arene($OPr_3$)($OPPh_2$) 1.1

Figure 40:
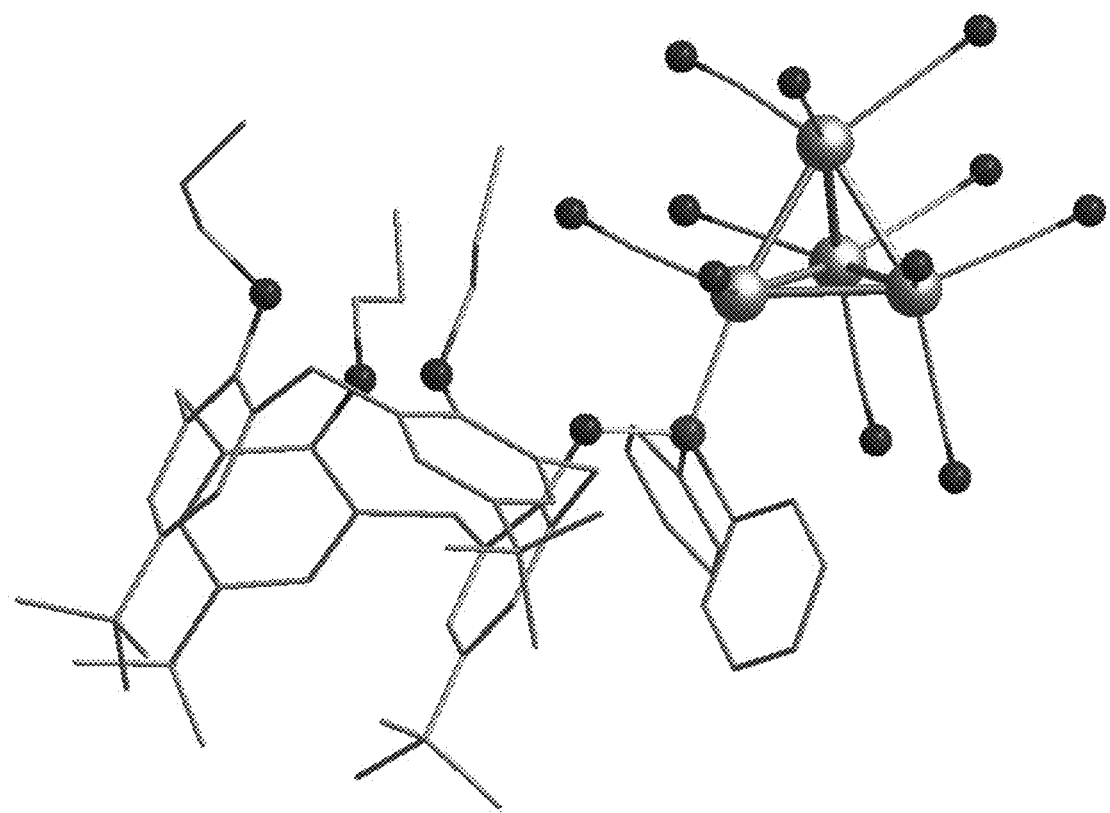
FIG. 40 shows the crystal structure of 1.1 showing absence of bridging CO ligands.
Figure 41:
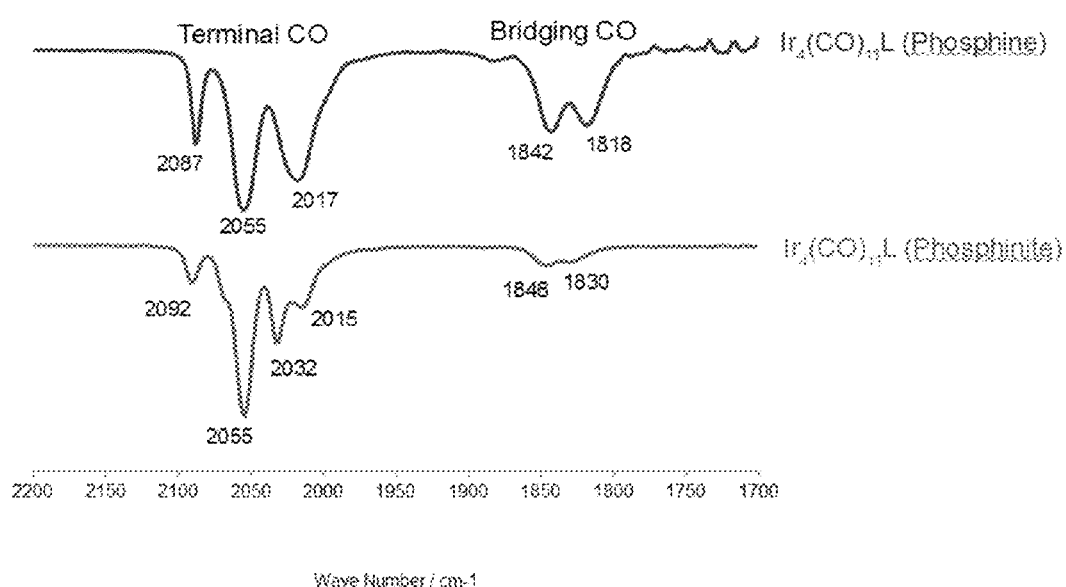
FIG. 41 shows a comparison of the IR spectra of Ir$_4$(CO)$_{11}$L with L=phosphine (top) and L=phosphinite (bottom).

The title compound is synthesized by treatment of $[Ir_4(CO)_{11}Br]^-$ with one equivalent of the ligand L (t-butylcalix[4]arene($OPr_3$)($OPPh_2$) at room temperature. Column chromatography yields pure complex 1.1 (>90%). Scheme 3 summarizes the synthesis conditions. The high-resolution ESI mass spectrum shows the pattern of $[1.1]^{\cdot+}$ (observed: m/z=2036.6; calculated: m/z=2036.4). The $^{31}$P{$^1$H}NMR spectrum contains one singlet peak at a high field (91 ppm). This indicates that the phosphinite ligand occupies only one position. Compared to the corresponding phosphine complex 1, the phosphorus signal is shifted towards higher field. The crystal structure of 1.1 in FIG. 40 shows the $Ir_4$ cluster core with one phosphinite ligand bound in an axial position. As in 1, the bulky phosphinite ligand causes a distortion of the Ir bound CO ligands. The bond angle Ir—C—O is smaller (177.7° and 176.7°) for the phosphinite bound Ir atom compared to the unsubstituted Ir atoms (average: 178.4°). In the crystal structure, no bridging CO ligands are present, while the FTIR data in FIG. 41 clearly shows some band intensity in the bridging CO stretching range. Compared to the FTIR data of the corresponding phosphine complex 1, the intensity of these peaks is significantly lower. This implies that the compound 1.1 contains two fractions: a major fraction without bridging COs and a minor fraction with bridging COs. The bands are blueshifted compared to 1 (2092; 2055; 2032 $cm^{-1}$ vs. 2089; 2055; 2018 $cm^{-1}$), consistent with the phosphinite bound $Ir_4$ core is less electron rich than the phospine complex.

Scheme 3: Synthesis of 1.1, the first calixarene phosphinite-bound metal cluster.

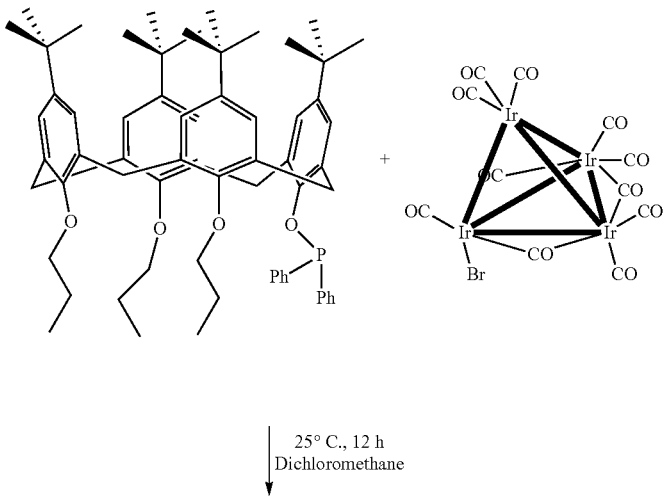

25° C., 12 h
Dichloromethane

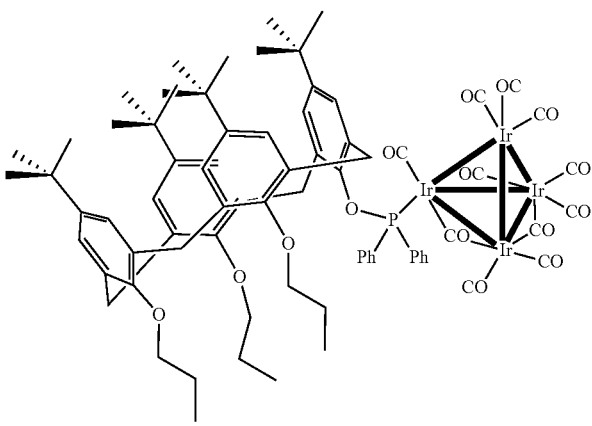

Example 8

Diversification of Functional Groups that Bind to Metal Clusers: C-Containing Substituents

Synthesis of Calix[4]arene Carbene

An Arduengo carbene is a relatively stable species despite being an intermediate with unpaired electrons on carbon. Such a carbene can be considered as a phosphine analogue in metal binding, having electron donor properties similar to those of a phosphine, such as that used in clusters 1-5 above. The electron pair on the carbon atom of the Arduengo carbene is stabilized by two adjacent nitrogens within the heterocyclic ring.

Calixarene-based carbenes could be used as ligands for iridium-carbonyl binding. Building on our synthesis and characterization of complexes of lower-rim phosphine with Ir clusters, we aim to replace the phosphine substituent with a N-heterocyclic carbene substituent. Remarkably, few examples of upper-rim imidazolium calixarene salts are known, which are capable of serving as precursors to a N-heterocyclic carbene. We plan to extend the number of potential ligands by incorporating N-heterocyclic carbenes on the lower (narrow) macrocyclic calixarene ring.

The lower-rim mono functionalization of the lower rim of parent tert-butylcalixarene-tetrol 6 has been performed via Mitsunobu type reaction with N-methyl-imidazolmethanol in the presence DEAD/TPP. The product 7 was isolated with moderate yield. This reaction is represented in Scheme 4. Unfortunately, the resulting monocalixarene-imidazolium salt 7 dimerizes according to ES MS data, which show the presence of a strong dimer peak. In order to avoid dimerization, the tripropyl analogue of the monoimidazolium salt was synthesized. Two approaches (Approach A and Approach B) were used to synthesize the target monoimidazololcalix[4]arene salt.

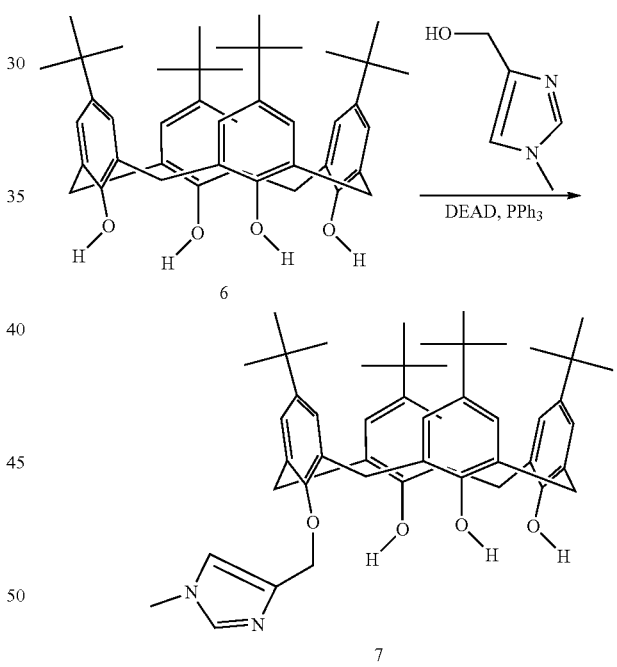

Scheme 4. Specific monofunctionalization of the calixarene lower rim with a N-methyl-imidazolmethanol substituent.

Approach A

Tripropoxycalix[4]arene (cone) 8 was exhaustively alkylated with 1,2-dibromoethane in the presence of NaH. The compound 9 was synthesized exclusively in the cone conformer in a yield of 48%. Attempts to obtain the target monoimidazolium salt of the calixarene via quaternization of 1-phenylimidazole with bromocalixarene 9 failed as shown in Scheme 5. Even exhaustive refluxing bromocalixarene 9 with a large excess of 1-phenylimidazole for a period of three days in chloroform gave only a mixture containing initial starting compounds, according to $^1$H NMR spectroscopy and thin layer chromatography.

Scheme 5. Failed synthetic approach for the synthesis of calixarene consisting of a substituent that is a carbine precursor.

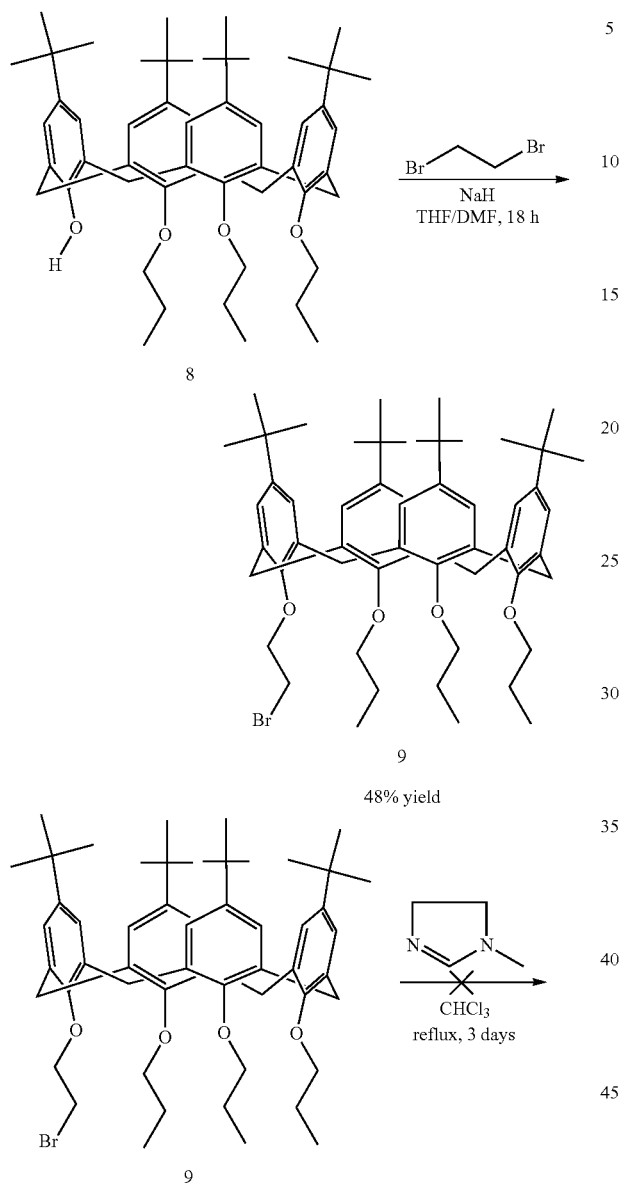

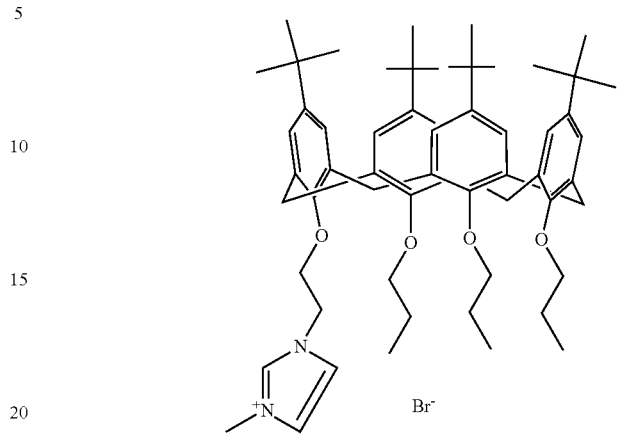

Approach B

Chlormethylimidazole 10 was synthesized by the reaction of hydroxymethylimidazolhydrochloride with thionyl chloride. The next synthetic step consists of reaction of monosodium salt of tripropoxycalixarene 11, which is generated in-situ using 10 equivalents of NaH, with 5 eqs. MeImCH$_2$Cl, as shown in Scheme 6. After stirring at room temperature in DMF, the target calixarene imidazole 12 was synthesized in good yield. The compound 12 exists as cone conformer which is demonstrated by the presence of an AB spin system consisting of equatorial and axial methylene hydrogens in the $^1$H NMR spectrum.

Formation of imidazol-2-ylidene-calix[4]arene via deprotonation of imidazolium salt with potassium-tert-butoxide, could be performed as shown in Scheme 5. The desired carbene will be synthesized in situ and will subsequently be immediately complexed to an Ir$_4$ cluster as shown in Scheme 5.

Scheme 6. Successful approach for the synthesis of target calixarene 12, which can serve as a carbine precursor.

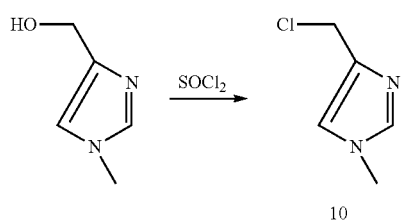

-continued
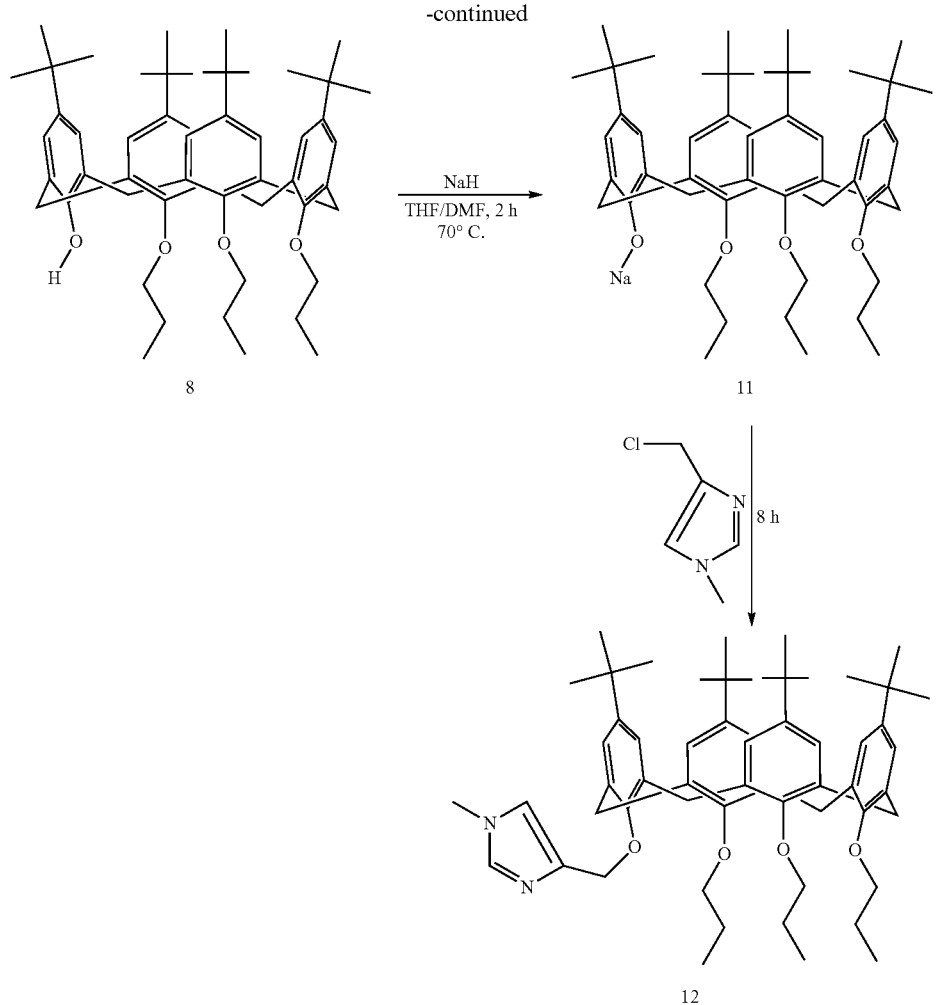
Scheme 7. Proposed path for the synthsis of a calixarene carbene ligand, and its complexation to an Ir₄ metal cluster.
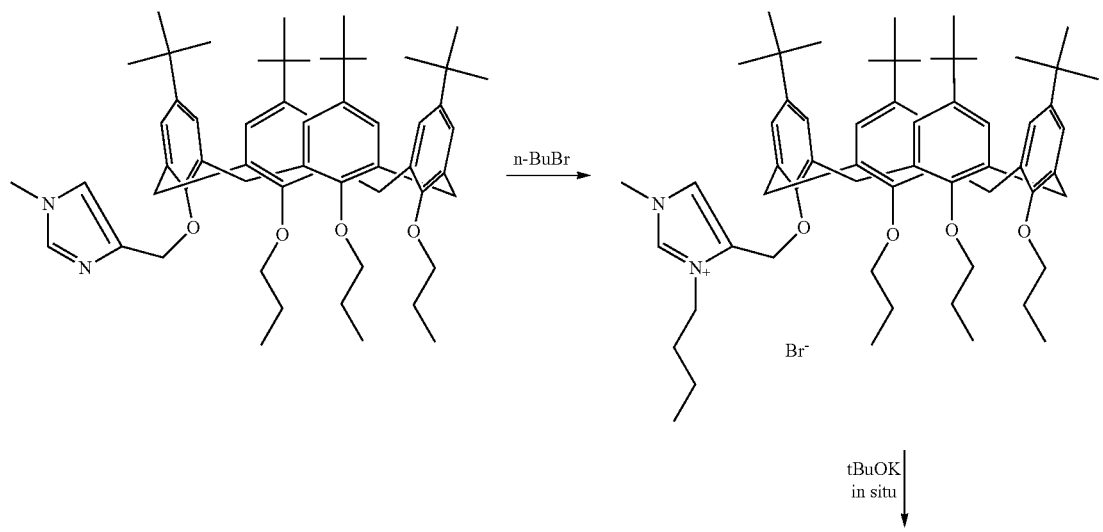

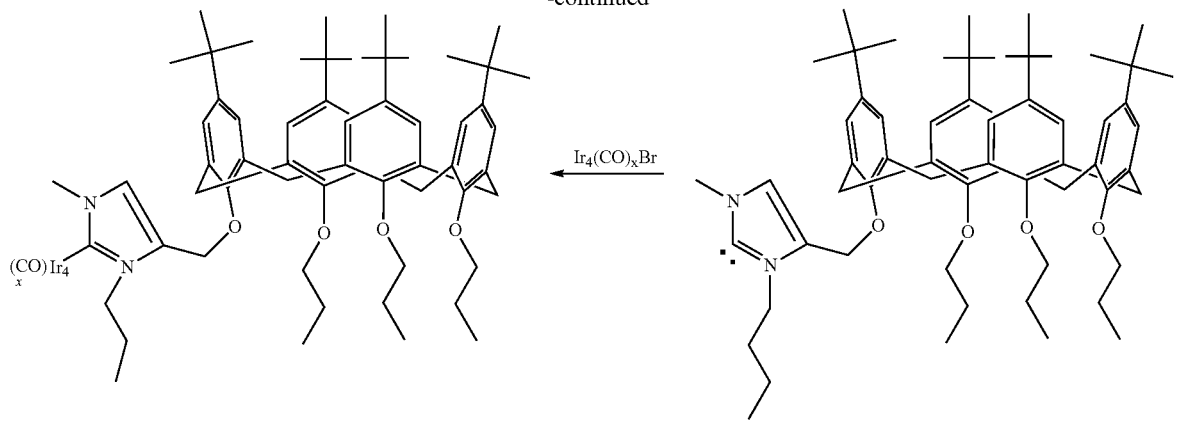

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

We claim:

1. A metal colloid formed by a process comprising performing a reaction on a complex comprising:
   (a) a metal colloid comprising a plurality of iridium atoms; and
   (b) a calixarene-related compound comprising a linker, wherein the linker comprises a coordinating atom coordinated to one of the plurality of iridium atoms; wherein the reaction is selected from pyrolysis, thermal decomposition, oxidative decomposition and a combination thereof.

2. A catalytic process comprising reducing an organic molecule by contacting the organic molecule with (a) a complex or the metal colloid of claim 1 and (b) a reductant; wherein the complex comprises:
   (i) a metal colloid comprising a plurality of iridium atoms; and
   (ii) a calixarene-related compound comprising a linker, wherein the linker comprises a coordinating atom coordinated to one of the plurality of iridium atoms.

3. The catalytic process of claim 2 wherein the organic molecule is a substituted or unsubstituted alkyl.

4. The catalytic process of claim 2 wherein the reducing step comprises hydrogenation.

* * * * *